US011111275B2

(12) United States Patent
Morrison

(10) Patent No.: US 11,111,275 B2
(45) Date of Patent: Sep. 7, 2021

(54) COMPOSITIONS AND METHODS FOR MAKING AND USING VIRUS-LIKE PARTICLES (VLPS)

(71) Applicant: University of Massachusetts, Boston, MA (US)

(72) Inventor: Trudy Gilkerson Morrison, Northborough, MA (US)

(73) Assignee: The University of Massachusetts, Boston, MA (US)

( * ) Notice: Subject to any disclaimer, the term of this patent is extended or adjusted under 35 U.S.C. 154(b) by 9 days.

(21) Appl. No.: 16/575,784

(22) Filed: Sep. 19, 2019

(65) Prior Publication Data

US 2020/0109176 A1    Apr. 9, 2020

Related U.S. Application Data

(60) Provisional application No. 62/806,526, filed on Feb. 15, 2019, provisional application No. 62/735,503, filed on Sep. 24, 2018.

(51) Int. Cl.
| C07K 14/005 | (2006.01) |
| A61K 39/155 | (2006.01) |
| C12N 7/00 | (2006.01) |
| A61K 39/00 | (2006.01) |

(52) U.S. Cl.
CPC .......... *C07K 14/005* (2013.01); *A61K 39/155* (2013.01); *C12N 7/00* (2013.01); *A61K 2039/545* (2013.01); *A61K 2039/55* (2013.01); *A61K 2039/58* (2013.01); *C07K 2319/00* (2013.01); *C12N 2760/18123* (2013.01); *C12N 2760/18143* (2013.01); *C12N 2760/18522* (2013.01); *C12N 2760/18534* (2013.01)

(58) Field of Classification Search
CPC .............. C07K 14/005; C07K 2319/00; C07K 2319/735; A61K 39/155; A61K 2039/58; A61K 2039/55; A61K 2039/545; A61K 39/12; A61K 2039/5258; C12N 7/00; C12N 2760/18143; C12N 2760/18522; C12N 2760/18123; C12N 2760/18534
See application file for complete search history.

(56) References Cited

U.S. PATENT DOCUMENTS

| 7,951,384 B2 | 5/2011 | Morrison et al. | .......... 424/214.1 |
| 8,974,797 B2 | 3/2015 | Morrison | .................... 424/193.1 |
| 9,216,212 B2 | 12/2015 | Morrison | .................... 424/199.1 |
| 9,399,059 B2 | 7/2016 | Morrison | .................... 424/199.1 |

OTHER PUBLICATIONS

Schmidt MR, McGinnes-Cullen LW, Kenward SA, Willems KN, Woodland RT, Morrison TG. Modification of the respiratory syncytial virus f protein in virus-like particles impacts generation of B cell memory. J Virol. Sep. 1, 2014;88(17):10165-76. Epub Jun. 25, 2014.*
Blanco JCG, Pletneva LM, McGinnes-Cullen L, Otoa RO, Patel MC, Fernando LR, Boukhvalova MS, Morrison TG. Efficacy of a respiratory syncytial virus vaccine candidate in a maternal immunization model. Nat Commun. May 15, 2018;9(1):1904.*
Bachmann, M. F. et al. (2010) "Vaccine delivery: a matter of size, geometry, kinetics and molecular patterns," *Nature Reviews Immunology* 10(11), 787-796.
Blanco, M. et al. (2018) "Positive and negative regulation of carbon nanotube catalysts through encapsulation within macrocycles," *Nature Communications* 9(1), 2671-2671.
Boyce, F. M. et al. (1996) "Baculovirus-mediated gene transfer into mammalian cells," *Proceedings of the National Academy of Sciences* 93(6), 2348.
Condreay, J. P. et al. (1999) "Transient and stable gene expression in mammalian cells transduced with a recombinant baculovirus vector," *Proceedings of the National Academy of Sciences of the United States of America* 96(1), 127-132.
Cullen, L. M. et al. (2015) "Cotton rat immune responses to virus-like particles containing the pre-fusion form of respiratory syncytial virus fusion protein," *Journal of Translational Medicine* 13, 350-350.
Cullen, L. M. et al. (2017) "The importance of RSV F protein conformation in VLPs in stimulation of neutralizing antibody titers in mice previously infected with RSV," *Human Vaccines & Immunotherapeutics* 13(12), 2814-2823.
Falloon, J. et al. (2017) "An Adjuvanted, Postfusion F Protein-Based Vaccine Did Not Prevent Respiratory Syncytial Virus Illness in Older Adults," *Journal of Infectious Diseases* 216(11), 1362-1370.
Falsey, A. R. et al. (2005) "Respiratory Syncytial Virus Infection in Elderly and High-Risk Adults," *New England Journal of Medicine* 352(17), 1749-1759.
Falsey, A. R. et al. (2000) "Respiratory Syncytial Virus Infection in Adults," *Clinical Microbiology Reviews* 13(3), 371.
Fields, B. N. et al. (2007) *Fields virology*, Wolters Kluwer Health/Lippincott Williams & Wilkins, Philadelphia.
Flynn, J. M. et al. (2016) "Evidence and Role for Bacterial Mucin Degradation in Cystic Fibrosis Airway Disease," *PLoS Pathogens* 12(8), e1005846.
Fornwald, J. A. et al. (2016) "Gene Expression in Mammalian Cells Using BacMam, a Modified Baculovirus System," *Methods in Molecular Biology* 1350, 95-116.
Galasinski, S. K. et al. (2000) "Acetyl coenzyme A stimulates RNA polymerase II transcription and promoter binding by transcription factor IID in the absence of histones," *Molecular and Cellular Biology* 20(6), 1923-1930.
GE, J. et al. (2015) "Construction of Recombinant Baculoviruses Expressing Infectious Bursal Disease Virus Main Protective Antigen and Their Immune Effects on Chickens," *PLoS One* 10(7), e0132993-e0132993.

(Continued)

*Primary Examiner* — Rachel B Gill
(74) *Attorney, Agent, or Firm* — Medlen & Carroll, LLP

(57) ABSTRACT

The present invention provides compositions and methods for using prophylactic and/or therapeutic vaccines to immunize subjects, and offspring of immunized female subjects, against respiratory syncytial virus (RSV). The invention also provides compositions and methods for producing increased yields of recombinant virus-like particles (VLPs).

19 Claims, 29 Drawing Sheets

Specification includes a Sequence Listing.

(56) References Cited

OTHER PUBLICATIONS

Gilman, M. S. A. et al. (2015) "Characterization of a Prefusion-Specific Antibody That Recognizes a Quaternary, Cleavage-Dependent Epitope on the RSV Fusion Glycoprotein," *PLoS Pathogens* 11(7), e1005035.
Graham, B. S. et al. (2015) "Novel antigens for RSV vaccines," *Current Opinion in Immunology* 35, 30-38.
Grunstein, M. (1997) "Histone acetylation in chromatin structure and transcription," *Nature* 389(6649), 349-352.
Hall, C. B. (2001) "Respiratory Syncytial Virus and Parainfluenza Virus," *New England Journal of Medicine* 344(25), 1917-1928.
Han, L. L. et al. (1999) "Respiratory Syncytial Virus Pneumonia among the Elderly: an Assessment of Disease Burden," *Journal of Infectious Diseases* 179(1), 25-30.
Ison, M. G. (2009) "Respiratory syncytial virus and other respiratory viruses in the setting of bone marrow transplantation," *Current Opinion in Oncology* 21(2), 171-176.
Jardetzky, T. S. et al. (2004) "A class act," *Nature* 427(6972), 307-308.
Kost, T. A. et al. (2005) "Baculovirus as versatile vectors for protein expression in insect and mammalian cells," *Nature Biotechnology* 23(5), 567-575.
Krarup, A. et al. (2015) "A highly stable prefusion RSV F vaccine derived from structural analysis of the fusion mechanism," *Nature Communications* 6, 8143.
Lee, H.-P. et al. (2007) "Chapter 15: Expression in mammalian cells using BacMam virus," in *Expression Systems* (Dyson, M. R., et al., Eds.), pp. 261-276, Scion Publishing Limited.
Lee, W.-J. et al. (2012) "Complete Genome Sequence of Human Respiratory Syncytial Virus Genotype A with a 72-Nucleotide Duplication in the Attachment Protein G Gene," *Journal of Virology* 86(24), 13810.
Liang, B. et al. (2017) "Improved Prefusion Stability, Optimized Codon Usage, and Augmented Virion Packaging Enhance the Immunogenicity of Respiratory Syncytial Virus Fusion Protein in a Vectored-Vaccine Candidate," *Journal of Virology* 91(15), e00189-00117.
McGinnes Cullen, L. et al. (2015) "Murine Immune Responses to Virus-Like Particle-Associated Pre- and Postfusion Forms of the Respiratory Syncytial Virus F Protein," *Journal of Virology* 89(13), 6835.
McGinnes, L. W. et al. (2011) "Assembly and Immunological Properties of Newcastle Disease Virus-Like Particles Containing the Respiratory Syncytial Virus F and G Proteins," *Journal of Virology* 85(1), 366.
McGinnes, L. W. et al. (2010) "Assembly and Biological and Immunological Properties of Newcastle Disease Virus-Like Particles," *Journal of Virology* 84(9), 4513.
McLellan, J. S. et al. (2013) "Structure-Based Design of a Fusion Glycoprotein Vaccine for Respiratory Syncytial Virus," *Science* 342(6158), 592.
McLellan, J. S. et al. (2010) "Structural basis of respiratory syncytial virus neutralization by motavizumab," *Nature Structural & Molecular Biology* 17(2), 248-250.
McLellan, J. S. et al. (2013) "Structure of RSV Fusion Glycoprotein Trimer Bound to a Prefusion-Specific Neutralizing Antibody," *Science* 340(6136), 1113.
Monti, B. et al. (2009) "Biochemical, Molecular and Epigenetic Mechanisms of Valproic Acid Neuroprotection," *Current Molecular Pharmacology* 2(1), 95-109.
Mousa, J. J. et al. (2016) "Structural basis for nonneutralizing antibody competition at antigenic site II of the respiratory syncytial virus fusion protein," *Proceedings of the National Academy of Sciences* 113(44), E6849.
Murawski, M. R. et al. (2010) "Newcastle Disease Virus-Like Particles Containing Respiratory Syncytial Virus G Protein Induced Protection in BALB/c Mice, with No Evidence of Immunopathology," *Journal of Virology* 84(2), 1110-1123.
Neumann, D. M. et al. (2007) "In Vivo Changes in the Patterns of Chromatin Structure Associated with the Latent Herpes Simplex Virus Type 1 Genome in Mouse Trigeminal Ganglia Can Be Detected at Early Times after Butyrate Treatment," *Journal of Virology* 81(23), 13248.
Neuzil, K. M. (2016) "Progress toward a Respiratory Syncytial Virus Vaccine," *Clinical and Vaccine Immunology* 23(3), 186-188.
Ngwuta, J. O. et al. (2015) "Prefusion F-specific antibodies determine the magnitude of RSV neutralizing activity in human sera," *Science Translational Medicine* 7(309), 309ra162.
Palomo, C. et al. (2016) "Influence of Respiratory Syncytial Virus F Glycoprotein Conformation on Induction of Protective Immune Responses," *Journal of Virology* 90(11), 5485-5498.
Pantua, H. D. et al. (2006) "Requirements for the Assembly and Release of Newcastle Disease Virus-Like Particles," *Journal of Virology* 80(22), 11062-11073.
Ping, W. et al. (2006) "Baculovirus-mediated gene expression in chicken primary cells," *Avian Diseases* 50(1), 59-63.
Raboni, S. M. et al. (2003) "Respiratory tract viral infections in bone marrow transplant patients," *Transplantation* 76(1), 142-146.
Russell, C. J. et al. (2018) "Vaccines for the Paramyxoviruses and Pneumoviruses: Successes, Candidates, and Hurdles," *Viral Immunology* 31(2), 133-141.
Shah, J. N. et al. (2011) "Management of RSV infections in adult recipients of hematopoietic stem cell transplantation," *Blood* 117(10), 2755-2763.
Shi, T. et al. (2017) "Global, regional, and national disease burden estimates of acute lower respiratory infections due to respiratory syncytial virus in young children in 2015: a systematic review and modelling study," *Lancet* 390(10098), 946-958.
Swanson, K. A. et al. (2014) "A Monomeric Uncleaved Respiratory Syncytial Virus F Antigen Retains Prefusion-Specific Neutralizing Epitopes," *Journal of Virology* 88(20), 11802.
Swanson, K. A. et al. (2011) "Structural basis for immunization with postfusion respiratory syncytial virus fusion F glycoprotein (RSV F) to elicit high neutralizing antibody titers," *Proceedings of the National Academy of Sciences* 108(23), 9619.
Thompson, W. W. et al. (2003) "Mortality Associated With Influenza and Respiratory Syncytial Virus in the United States," *JAMA* 289(2), 179-186.
Wu, H. et al. (2005) "Ultra-potent Antibodies Against Respiratory Syncytial Virus: Effects of Binding Kinetics and Binding Valence on Viral Neutralization," *Journal of Molecular Biology* 350(1), 126-144.

* cited by examiner

Cell Extracts

F/Fs: DS-Cav1, Post-F/F, PR-DM, PR-TM, SC-DM, SC-TM
F/Fs + H/G: DS-Cav1, Post-F/F, PR-DM, PR-TM, SC-DM, SC-TM Cell Surfaces $F_0$
$F_1$ 120
100
80
60
50
40
30

$F_0$
$F_1$

Anti-RSV HR2

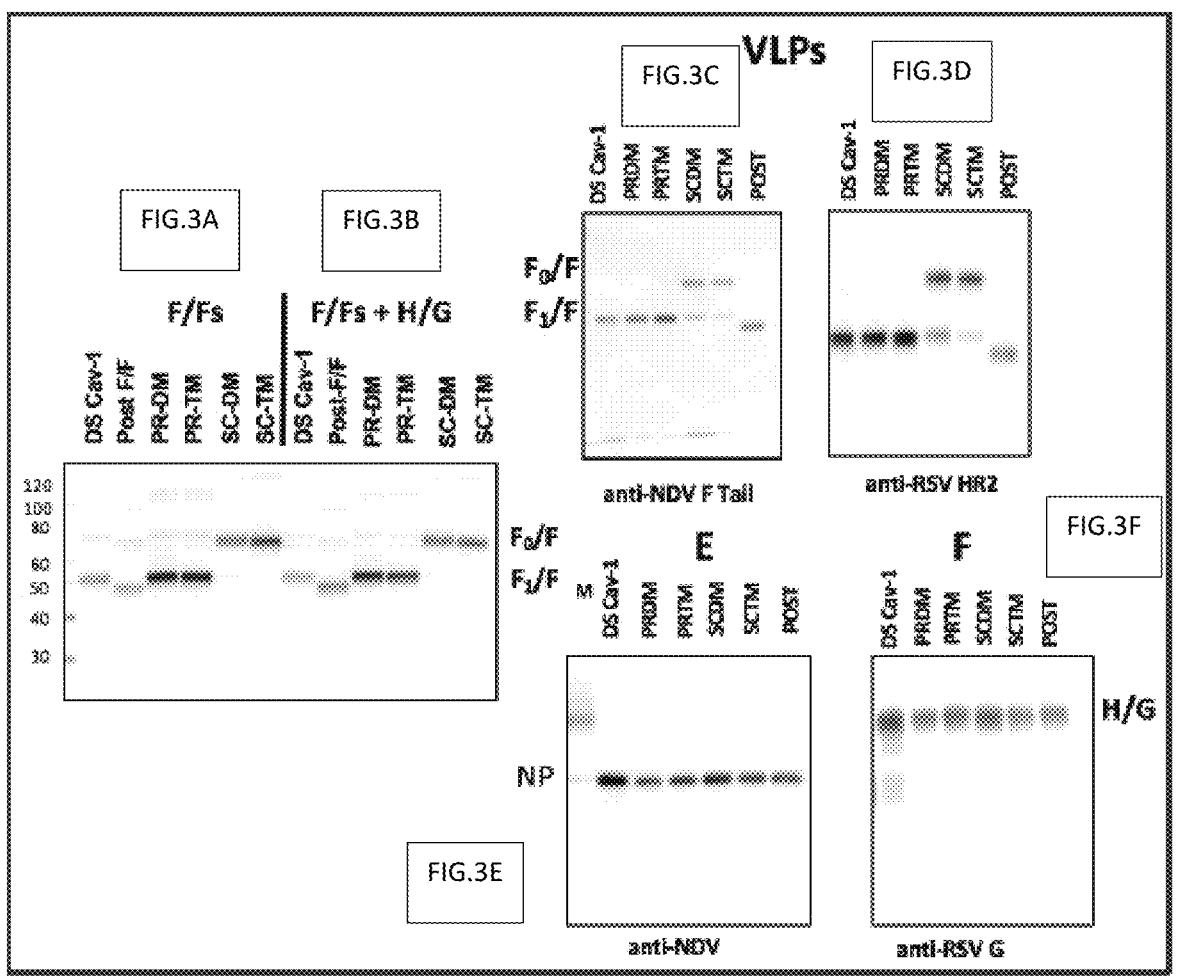

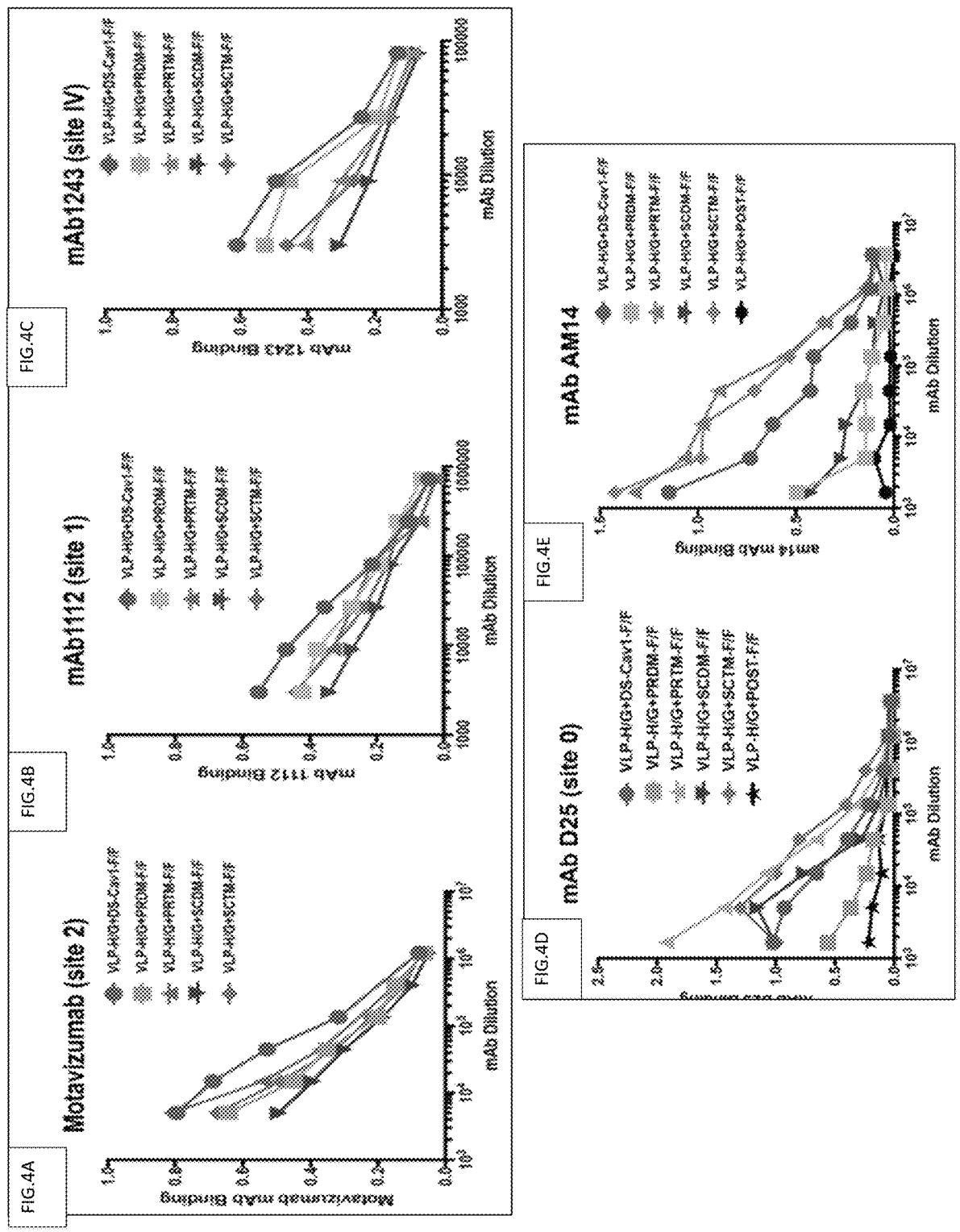

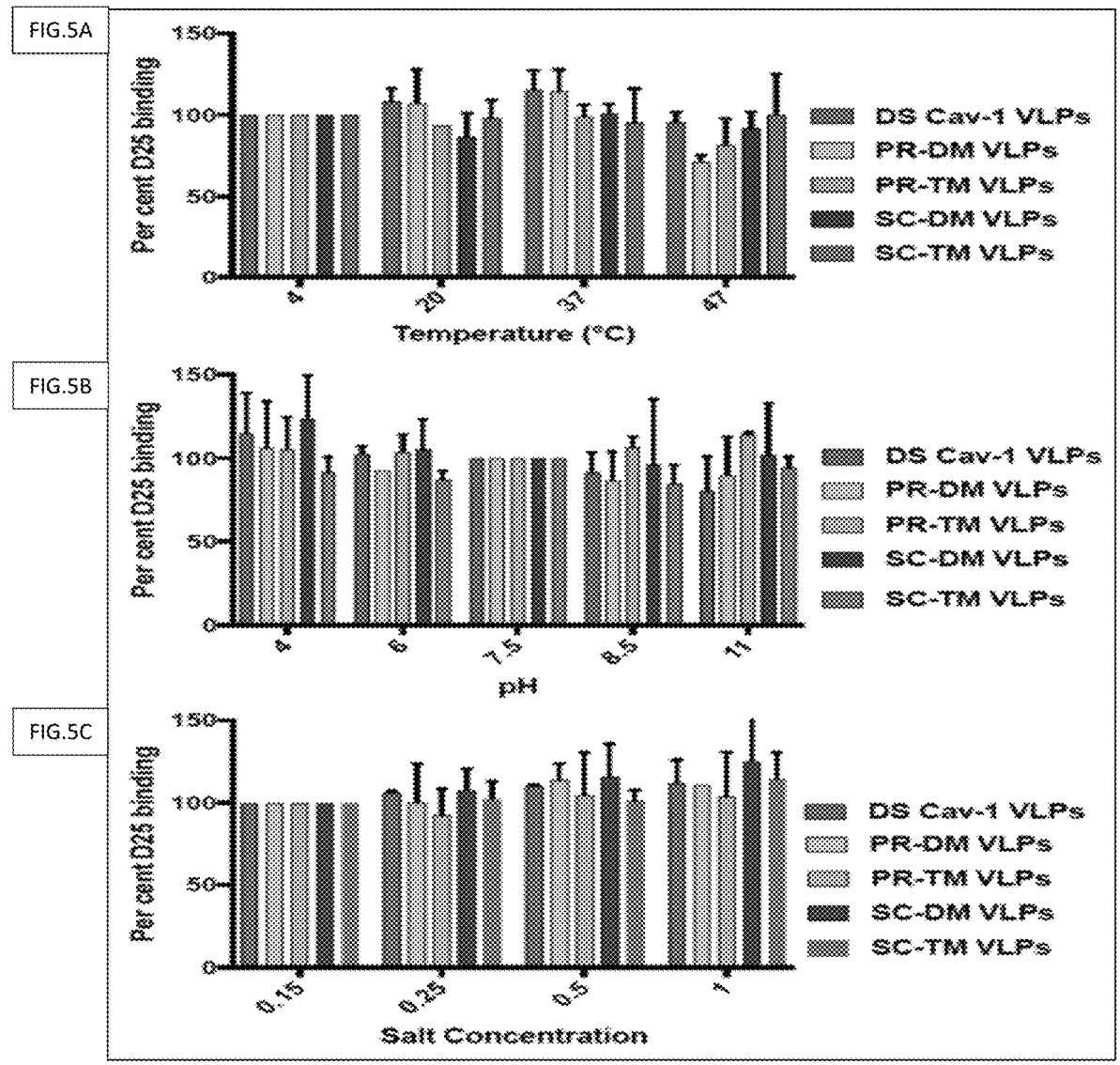

A) FIGURE 14A Post-fusion F/F DNA Sequence (SEQ ID NO:01)

ATGGAGCTTCTTATTCTCAAAGCCAATGCTATTACTACCATCCTGACAGCCGTGACATTTTGCTTCGCCAG
TGGACAGAATATCACTGAGGAATTCTATCAGAGCACCTGTTCCGCTGTATCAAAAGGGTATCTCTCCGCA
TTACGAACCGGATGGTACACTTCAGTCATCACAATTGAACTTTCTAACATTAAAGAGAATAAGTGTAACG
GGACTGACGCTAAAGTGAAGTTGATAAAGCAGGAGCTAGACAAATATAAGAATGCAGTAACTGAACTT
CAGTTGCTTATGCAGTCCACACCTGCTACTAACAATAGAGCACGCCGTGAACTGCCTAGATTCATGAACT
ATACTCTTAATAACGCAAAAAAGACTAATGTTACCCTTTCCAAGAAACAGAAACAGCAAGCTATTGCTTC
AGGAGTAGCAGTAAGTAAGGTATTACATTTGGAAGGCGAAGTGAACAAAATTAAATCAGCACTGCTTTC
CACTAACAAGGCAGTAGTGAGTCTGTCTAATGGTGTTAGCGTTTTAACTTCTAAAGTGCTGGATTTAAAG
AACTACATCGATAAACAGCTGCTCCCCATCGTAAACAAGCAGAGTTGCCGTATCAGCAACATAGAGACA
GTGATAGAGTTTCAGCAGAAGAACAATAGGCTGCTTGAAATAACTCGCGAATTTAGCGTTAACGCAGGC
GTGACTACCCCAGTGTCCACTTATATGCTGACAAACTCAGAGTTACTTTCTCTGATCAACGACATGCCAAT
AACTAATGATCAGAAGAAATTAATGTCTAATAACGTGCAGATAGTTCGGCAGCAGTCCTACAGTATCAT
GAGCATTATCAAGGAAGAGGTATTGGCCTATGTCGTTCAGTTACCTTTATACGGTGTTATCGATACCCCA
TGTTGGAAGCTCCATACCAGCCCCTTGTGTACTACCAATACTAAAGAGGGGAGCAATATTTGTCTAACTA
GGACCGATAGGGGCTGGTACTGCGACAACGCAGGGAGTGTTTCTTTCTTTCCTCAGGCAGAAACATGCA
AGGTGCAGAGCAACAGAGTGTTTTGCGATACTATGAATAGCCTGACTCTGCCATCCGAAGTTAATCTGT
GTAACGTCGATATATTTAATCCAAAATACGATTGCAAAATCATGACTTCAAAAACAGACGTGAGCAGTTC
AGTCATAACTTCTCTAGGTGCCATTGTTTCATGCTACGGAAAAACTAAGTGTACCGCTAGCAACAAAAAC
AGAGGTATTATCAAGACTTTCTCCAATGGCTGCGATTACGTTTCCAACAAGGGTGTCGATACAGTCTCAG
TCGGGAATACCTTATATTACGTTAATAAACAGGAGGGGAAGTCTCTGTATGTGAAAGGTGAGCCAATAA
TTAATTTTTATGATCCTTTAGTATTTCCATCTGACGAGTTTGACGCATCCATTTCTCAGGTTAACGAAAAG
ATCAACCAGAGCTTGGCTTTTATAAGGAAGAGTGACGAGCTCCTCCATAACGTCAACGCCGGGAAAAGT
ACTACTAAT**CTCATTACCTATATCGCTTTAACTGCCATATCTCTTGTTTGCGGTATACTTAGTCTGGTTCT
AGCATGCTACCTAATGTACAAGCAAAAGGCGCAACAAAAGACCTTGTTATGGCTTGGGAATAATACCC
TGGGTCAGATGAGAGCCACTACAAAAATGTGA**

B) FIGURE 14B Post-fusion F/F DNA Sequence (SEQ ID NO:02)

MELLILKANAITTILTAVTFCFASGQNITEEFYQSTCSAVSKGYLSALRTGWYTSVITIELSNIKENKCNGTDAKV
KLIKQELDKYKNAVTELQLLMQSTPATNNRARRELPRFMNYTLNNAKKTNVTLSKKQKQQAIASGVAVSKVL
HLEGEVNKIKSALLSTNKAVVSLSNGVSVLTSKVLDLKNYIDKQLLPIVNKQSCRISNIETVIEFQQKNNRLLEITR
EFSVNAGVTTPVSTYMLTNSELLSLINDMPITNDQKKLMSNNVQIVRQQSYSIMSIIKEEVLAYVVQLPLYGVI
DTPCWKLHTSPLCTTNTKEGSNICLTRTDRGWYCDNAGSVSFFPQAETCKVQSNRVFCDTMNSLTLPSEVNL
CNVDIFNPKYDCKIMTSKTDVSSSVITSLGAIVSCYGKTKCTASNKNRGIIKTFSNGCDYVSNKGVDTVSVGNT
LYYVNKQEGKSLYVKGEPIINFYDPLVFPSDEFDASISQVNEKINQSLAFIRKSDELLHNVNAGKSTTN**LITYIALT
AISLVCGILSLVLACYLMYKQKAQQKTLLWLGNNTLGQMRATTKM***

FIG. 15A 1DS-CAV1 F/F DNA Sequence (i.e., Pre-fusion F/F DNA Sequence) (SEQ ID NO:03)

ATGGAGCTGCTGATCCTGAAGGCCAACGCCATTACCACCATTCTGACAGCCGTGACATTCTGCTTCGCCT
CCGGACAGAACATCACAGAGGAGTTCTATCAGAGCACCTGTTCCGCCGTCTCCAAAGGATATCTGAGCG
CCCTGAGGACCGGCTGGTATACCTCCGTGATCACCATCGAGCTTAGCAACATCAAGGAGAACAAGTGCA
ATGGCACCGACGCCAAGGTCAAGCTCATCAAGCAAGAGCTTGACAAGTACAAAAACGCCGTCACCGAG
CTTCAGCTGCTGATGCAGTCCACACCAGCTACCAACAACAGAGCCAGGAGAGAGCTTCCCAGATTCATG
AACTACACCCTGAACAACGCCAAGAAGACCAACGTGACCCTGTCCAAGAAAAGGAAAAGGAGGTTCCT
GGGCTTCCTCCTGGGAGTGGGATCCGCCATCGCTAGCGGCGTGGCCGTCTGTAAAGTCCTCCATCTGGA
AGGCGAGGTCAACAAGATCAAAAGCGCCCTGCTGTCCACAAACAAAGCTGTGGTCTCCCTGAGCAACG
GCGTCAGCGTCCTGACCTTCAAGGTGCTCGACCTCAAGAACTACATCGACAAGCAACTGCTCCCCATC**CT
C**AACAAGCAGAGCTGCAGGATCAGCAACATTGAAACCGTGATCGAGTTCCAGCAGAAGAATAACAGGC
TCCTGGAGATCACCAGGGAGTTCAGCGTGAATGCTGGCGTGACAACCCCCGTCTCCACCTACATGCTGA
CCAACAGCGAACTCCTGAGCCTGATCAACGATATGCCCATCACCAACGACCAGAAGAAGCTCATGAGCA
ACAACGTCCAGATCGTGAGGCAGCAGAGCTACAGCATCATGTGCATTATCAAAGAGGAGGTCCTGGCTT
ACGTGGTCCAGCTGCCCCTGTATGGAGTCATTGACACCCCCTGCTGGAAACTCCATACCAGCCCACTGTG
TACAACCAACACCAAGGAGGGCAGCAACATCTGCCTCACCAGAACCGATAGGGGCTGGTACTGCGACA
ACGCCGGATCCGTGAGCTTCTTCCCCCAGGCCGAGACCTGCAAGGTCCAGAGCAACAGGGTCTTCTGCG
ATACCATGAACAGCCTCACCCTGCCCTCCGAGGTGAATCTCTGTAATGTCGACATCTTCAATCCAAAGTA
CGACTGTAAGATCATGACCAGCAAGACCGACGTCAGCAGCAGCGTGATTACCAGCCTCGGAGCCATCGT
GAGCTGTTACGGCAAGACCAAGTGCACCGCCAGCAACAAGAACAGAGGAATTATCAAGACCTTCAGCA
ACGGATGCGACTACGTCTCCAACAAAGGCGTGGATACCGTCTCCGTGGGCAACACCCTGTACTACGTCA
ACAAGCAGGAAGGCAAAAGCCTGTACGTCAAGGGCGAGCCAATCATCAACTTTTACGATCCCCTCGTCT
TCCCCATCCGATGAGTTCGACGCCAGCATCTCCCAAGTCAACGAGAAGATCAACCAGTCCCTGGCCTTCAT
CAGAAAGTCCGACGAGCTCCTCCATAACGTCAACGCCGGGAAA*GGATATATCCCCGAAGCTCCTCGGG
ATGGTCAGGCCTACGTTCGCAAGGATGGAGAGTGGGTACTGCTGTCTACTTTCCTGAGTACTACTAAT*C
TCATTACCTAT<u>ATCGCTTTTAACTGCCATATCTCTTGTTTGCGGTATACTTAGTCTGGTTCTAGCATGCTAC
CTAATGTACAAGCAAAAGGCGCAACAAAAGACCTTGTTATGGCTTGGGAATAATACCCTGGGTCAGA
TGAGAGCCACTACAAAAATGTGA</u>

FIG. 15B DS-CAV1 F/F Protein Sequence (i.e., Pre-fusion F/F DNA Sequence) (SEQ ID NO:04)

MELLILKANAITTILTAVTFCFASGQNITEEFYQSTCSAVSKGYLSALRTGWYTSVITIELSNIKENKCNGTDAKV
KLIKQELDKYKNAVTELQLLMQSTPATNNRARRELPRFMNYTLNNAKKTNVTLSKKRKRRFLGFLLGVSAIA
SGVAVCKVLHLEGEVNKIKSALLSTNKAVVSLSNGVSVLTFKVLDLKNYIDKQLLPILNKQSCRISNIETVIEFQQ
KNNRLLEITREFSVNAGVTTPVSTYMLTNSELLSLINDMPITNDQKKLMSNNVQIVRQQSYSIMCIIKEEVLAY
VVQLPLYGVIDTPCWKLHTSPLCTTNTKEGSNICLTRTDRGWYCDNAGSVSFFPQAETCKVQSNRVFCDTM
NSLTLPSEVNLCNVDIFNPKYDCKIMTSKTDVSSSVITSLGAIVSCYGKTKCTASNKNRGIIKTFSNGCDYVSNK
GVDTVSVGNTLYYVNKQEGKSLYVKGEPIINFYDPLVFPSDEFDASISQVNEKINQSLAFIRKSDELLHNVNAG
K*GYIPEAPRDGQAYVRKDGEWVLLSTFL*STTN<u>LITYIALTAISLVCGILSLVLACYLMYKQKAQQKTLLWLGN
NTLGQMRATTKM*</u>

FIG. 16A PR-DM F/F DNA Sequence (SEQ ID NO:05)

ATGGAGCTGCTGATCCTGAAGGCCAACGCCATCACCACCATCCTGACCGCCGTGACCTTCTGCTTCGCCA
GCGGCCAGAACATTACCGAGGAGTTCTACCAGAGCACCTGCAGCGCCGTGAGCAAGGGCTACCTGAGC
GCCCTGAGAACCGGCTGGTACACCAGCGTGATCACCATCGAGCTGAGCAACATCAAGGAG<u>ATT</u>AAGTG
CAACGGCACCGACGCCAAGGTGAAGCTGATCAAGCAGGAGCTGGACAAGTACAAGAACGCCGTGACC
GAGCTGCAGCTGCTGATGCAGAGCACCCCCGCCACCAACAACAGGGCCAGGAGGGAGCTGCCCAGGTT
CATGAACTACACCCTGAACAACGCCAAGAAGACCAACGTGACCCTGAGCAAGAAGAGGAAGAGGAGGT
TCCTGGGCTTCCTGCTGGGAGTGGGCTCCGCCATCGCTTCCGGAGTGGCCGTGAGCAAGGTCCTGCACC
TGGAGGGCGAGGTCAATAAGATCAAGTCCGCCCTCCTGAGCACCAATAAGGCCGTCGTGAGCCTCAGC
AATGGCGTGAGCGTGCTGACATCCAAGGTCCTCGACCTGAAGAACTACATCGACAAGCAGCTGCTCCCT
ATCGTGAACAAACAGAGCTGCAGGATC<u>CCC</u>AACATCGAGACCGTGATCGAGTTCCAGCAGAAGAACAA
CAGGCTGCTGGAGATCACCAGGGAATTTAGCGTGAACGCCGGAGTGACCACCCCCGTGAGCACCTATAT
GCTGACAAACAGCGAGCTGCTGTCCCTGATCAACGACATGCCCATCACCAACGACCAGAAGAAGCTGAT
GAGCAATAACGTGCAGATCGTGAGGCAGCAGAGCTACAGCATCATGTCCATCATCAAGGAGGAGGTCC
TGGCTTACGTGGTCCAACTGCCTCTGTACGGCGTGATCGACACCCCTTGCTGGAAGCTGCACACAAGCCC
CCTGTGTACCACCAATACCAAGGAGGGCAGCAACATCTGCCTGACAAGGACCGACAGAGGCTGGTACT
GCGACAATGCCGGCTCCGTGTCCTTCTTTCCCCAGGCTGAGACCTGCAAGGTCCAGAGCAACAGGGTGT
TCTGCGACACCATGAACTCCCTGACCCTCCCCAGCGAGGTGAACCTGTGCAACGTCGACATCTTCAACCC
CAAGTACGATTGTAAGATCATGACCAGCAAAACCGACGTGAGCAGCAGCGTGATCACCTCCCTGGGCGC
CATCGTGAGCTGCTACGGCAAGACCAAGTGTACCGCCTCCAACAAGAATAGGGGAATCATTAAGACCTT
CTCCAACGGCTGCGACTACGTCTCCAACAAGGGCGTGGACACAGTGTCCGTGGGCAACACCCTGTACTA
CGTGAATAAGCAGGAGGGCAAGAGCCTGTACGTGAAGGGAGAGCCTATCATCAACTTTTACGACCCCCT
GGTGTTCCCTAGCGACGAGTTCGACGCCAGCATCAGCCAGGTGAACGAGAAGATCAACCAGAGCCTGG
CCTTCATCAGAAAGTCCGACGAGCTCCTCCATAACGTCAACGCCGGGAAA*GGATATATCCCCGAAGCTC*
*CTCGGGATGGTCAGGCCTACGTTCGCAAGGATGGAGAGTGGGTACTGCTGTCTACTTTCCTG*AGTACTA
CTAAT<u>CTCATTACCTATATCGCTTTAACTGCCATATCTCTTGTTTGCGGTATACTTAGTCTGGTTCTAGCA
TGCTACCTAATGTACAAGCAAAAGGCGCAACAAAAGACCTTGTTATGGCTTGGGAATAATACCCTGGG
TCAGATGAGAGCCACTACAAAAATGTGA</u>

FIG. 16B PR-DM F/F Protein Sequence (SEQ ID NO:06)

MELLILKANAITTILTAVTFCFASGQNITEEFYQSTCSAVSKGYLSALRTGWYTSVITIELSNIKE<u>I</u>KCNGTDAKVK
LIKQELDKYKNAVTELQLLMQSTPATNNRARRELPRFMNYTLNNAKKTNVTLSKKRKRRFLGFLLGVGSAIAS
GVAVSKVLHLEGEVNKIKSALLSTNKAVVSLSNGVSVLTSKVLDLKNYIDKQLLPIVNKQSCRI<u>P</u>NIETVIEFQQK
NNRLLEITREFSVNAGVTTPVSTYMLTNSELLSLINDMPITNDQKKLMSNNVQIVRQQSYSIMSIIKEEVLAYV
VQLPLYGVIDTPCWKLHTSPLCTTNTKEGSNICLTRTDRGWYCDNAGSVSFFPQAETCKVQSNRVFCDTMN
SLTLPSEVNLCNVDIFNPKYDCKIMTSKTDVSSSVITSLGAIVSCYGKTKCTASNKNRGIIKTFSNGCDYVSNKG
VDTVSVGNTLYYVNKQEGKSLYVKGEPIINFYDPLVFPSDEFDASISQVNEKINQSLAFIRKSDELLHNVNAGK
*GYIPEAPRDGQAYVRKDGEWVLLSTFL*STTN<u>LITYIALTAISLVCGILSLVLACYLMYKQKAQQKTLLWLGNN
TLGQMRATTKM</u>*

FIG. 17A PR-TM F/F DNA Sequence (SEQ ID NO:07)

ATGGAGCTGCTGATCCTGAAGGCCAACGCCATCACCACCATCCTGACCGCCGTGACCTTCTGCTTCGCCA
GCGGCCAGAACATTACCGAGGAGTTCTACCAGAGCACCTGCAGCGCCGTGAGCAAGGGCTACCTGAGC
GCCCTGAGAACCGGCTGGTACACCAGCGTGATCACCATCGAGCTGAGCAACATCAAGGAG<u>ATT</u>AAGTG
CAACGGCACCGACGCCAAGGTGAAGCTGATCAAGCAGGAGCTGGACAAGTACAAGAACGCCGTGACC
GAGCTGCAGCTGCTGATGCAGAGCACCCCCGCCACCAACAACAGGGCCAGGAGGGAGCTGCCCAGGTT
CATGAACTACACCCTGAACAACGCCAAGAAGACCAACGTGACCCTGAGCAAGAAGAGGAAGAGGAGGT
TCCTGGGCTTCCTGCTGGGAGTGGGCTCCGCCATCGCTTCCGGAGTGGCCGTGAGCAAGGTCCTGCACC
TGGAGGGCGAGGTCAATAAGATCAAGTCCGCCCTCCTGAGCACCAATAAGGCCGTCGTGAGCCTCAGC
AATGGCGTGAGCGTGCTGACATCCAAGGTCCTCGACCTGAAGAACTACATCGACAAGCAGCTGCTCCCT
ATCGTGAACAAACAGAGCTGCAGGATC<u>CCC</u>AACATCGAGACCGTGATCGAGTTCCAGCAGAAGAACAA
CAGGCTGCTGGAGATCACCAGGGAATTTAGCGTGAACGCCGGAGTGACCACCCCCGTGAGCACCTATAT
GCTGACAAACAGCGAGCTGCTGTCCCTGATCAACGACATGCCCATCACCAACGACCAGAAGAAGCTGAT
GAGCAATAACGTGCAGATCGTGAGGCAGCAGAGCTACAGCATCATGTCCATCATCAAGGAGGAGGTCC
TGGCTTACGTGGTCCAACTGCCTCTGTACGGCGTGATCGACACCCCTTGCTGGAAGCTGCACACAAGCCC
CCTGTGTACCACCAATACCAAGGAGGGCAGCAACATCTGCCTGACAAGGACCGACAGAGGCTGGTACT
GCGACAATGCCGGCTCCGTGTCCTTCTTTCCCCAGGCTGAGACCTGCAAGGTCCAGAGCAACAGGGTGT
TCTGCGACACCATGAACTCCCTGACCCTCCCCAGCGAGGTGAACCTGTGCAACGTCGACATCTTCAACCC
CAAGTACGATTGTAAGATCATGACCAGCAAAACCGACGTGAGCAGCAGCGTGATCACCTCCCTGGGCGC
CATCGTGAGCTGCTACGGCAAGACCAAGTGTACCGCCTCCAACAAGAATAGGGGAATCATTAAGACCTT
CTCCAACGGCTGCGACTACGTCTCCAACAAGGGCGTGGACACAGTGTCCGTGGGCAACACCCTGTACTA
CGTGAATAAGCAGGAGGGCAAGAGCCTGTACGTGAAGGGAGAGCCTATCATCAACTTTTACGACCCCCT
GGTGTTCCCTAGC<u>AAC</u>GAGTTCGACGCCAGCATCAGCCAGGTGAACGAGAAGATCAACCAGAGCCTGG
CCTTCATCAGAAAGTCCGACGAGCTCCTCCATAACGTCAACGCCGGGAAA*GGATATATCCCCGAAGCTC*
*CTCGGGATGGTCAGGCCTACGTTCGCAAGGATGGAGAGTGGGTACTGCTGTCTACTTTCCTG*AGTACTA
CTAAT<u>CTCATTACCTATATCGCTTTAACTGCCATATCTCTTGTTTGCGGTATACTTAGTCTGGTTCTAGCA
TGCTACCTAATGTACAAGCAAAAGGCGCAACAAAAGACCTTGTTATGGCTTGGGAATAATACCCTGGG
TCAGATGAGAGCCACTACAAAAATGTGA</u>

FIG. 17B PR-TM F/F Protein Sequence (SEQ ID NO:08)

MELLILKANAITTILTAVTFCFASGQNITEEFYQSTCSAVSKGYLSALRTGWYTSVITIELSNIKE<u>I</u>KCNGTDAKVK
LIKQELDKYKNAVTELQLLMQSTPATNNRARRELPRFMNYTLNNAKKTNVTLSKKRKRRFLGFLLGVGSAIAS
GVAVSKVLHLEGEVNKIKSALLSTNKAVVSLSNGVSVLTSKVLDLKNYIDKQLLPIVNKQSCRI<u>P</u>NIETVIEFQQK
NNRLLEITREFSVNAGVTTPVSTYMLTNSELLSLINDMPITNDQKKLMSNNVQIVRQQSYSIMSIIKEEVLAYV
VQLPLYGVIDTPCWKLHTSPLCTTNTKEGSNICLTRTDRGWYCDNAGSVSFFPQAETCKVQSNRVFCDTMN
SLTLPSEVNLCNVDIFNPKYDCKIMTSKTDVSSSVITSLGAIVSCYGKTKCTASNKNRGIIKTFSNGCDYVSNKG
VDTVSVGNTLYYVNKQEGKSLYVKGEPIINFYDPLVFPS<u>N</u>EFDASISQVNEKINQSLAFIRKSDELLHNVNAGK
*GYIPEAPRDGQAYVRKDGEWVLLSTFL*STTN<u>LITYIALTAISLVCGILSLVLACYLMYKQKAQQKTLLWLGNN
TLGQMRATTKM</u>*

FIG. 18A SC-DM F/F DNA Sequence (SEQ ID NO:09)

ATGGAGCTGCTGATCCTGAAGGCCAACGCCATCACCACCATCCTGACCGCCGTGACCTTCTGCTTCGCCA
GCGGCCAGAACATTACCGAGGAGTTCTACCAGAGCACCTGCAGCGCCGTGAGCAAGGGCTACCTGAGC
GCCCTGAGAACCGGCTGGTACACCAGCGTGATCACCATCGAGCTGAGCAACATCAAGGAG*ATT*AAGTG
CAACGGCACCGACGCCAAGGTGAAGCTGATCAAGCAGGAGCTGGACAAGTACAAGAACGCCGTGACC
GAGCTGCAGCTGCTGATGCAGAGCACCCCCGCCACCAACAAC*CAG*GCCAGG*GGGTCAGGGTCAGGA*A
GG*TCC*CTGGGCTTCCTGCTGGGAGTGGGCTCCGCCATCGCTTCCGGAGTGGCCGTGAGCAAGGTCCTGC
ACCTGGAGGGCGAGGTCAATAAGATCAAGTCCGCCCTCCTGAGCACCAATAAGGCCGTCGTGAGCCTCA
GCAATGGCGTGAGCGTGCTGACATCCAAGGTCCTCGACCTGAAGAACTACATCGACAAGCAGCTGCTCC
CTATCGTGAACAAACAGAGCTGCAGGATC*CCC*AACATCGAGACCGTGATCGAGTTCCAGCAGAAGAACA
ACAGGCTGCTGGAGATCACCAGGGAATTTAGCGTGAACGCCGGAGTGACCACCCCCGTGAGCACCTAT
ATGCTGACAAACAGCGAGCTGCTGTCCCTGATCAACGACATGCCCATCACCAACGACCAGAAGAAGCTG
ATGAGCAATAACGTGCAGATCGTGAGGCAGCAGAGCTACAGCATCATGTCCATCATCAAGGAGGAGGT
CCTGGCTTACGTGGTCCAACTGCCTCTGTACGGCGTGATCGACACCCCTTGCTGGAAGCTGCACACAAGC
CCCCTGTGTACCACCAATACCAAGGAGGGCAGCAACATCTGCCTGACAAGGACCGACAGAGGCTGGTA
CTGCGACAATGCCGGCTCCGTGTCCTTCTTTCCCCAGGCTGAGACCTGCAAGGTCCAGAGCAACAGGGT
GTTCTGCGACACCATGAACTCCCTGACCCTCCCCAGCGAGGTGAACCTGTGCAACGTCGACATCTTCAAC
CCCAAGTACGATTGTAAGATCATGACCAGCAAAACCGACGTGAGCAGCAGCGTGATCACCTCCCTGGGC
GCCATCGTGAGCTGCTACGGCAAGACCAAGTGTACCGCCTCCAACAAGAATAGGGGAATCATTAAGACC
TTCTCCAACGGCTGCGACTACGTCTCCAACAAGGGCGTGGACACAGTGTCCGTGGGCAACACCCTGTAC
TACGTGAATAAGCAGGAGGGCAAGAGCCTGTACGTGAAGGGAGAGCCTATCATCAACTTTTACGACCC
CCTGGTGTTCCCTAGCGACGAGTTCGACGCCAGCATCAGCCAGGTGAACGAGAAGATCAACCAGAGCCT
GGCCTTCATCAGAAAGTCCGACGAGCTCCTCCATAACGTCAACGCCGGGAAA*GGATATATCCCCGAAGC*
*TCCTCGGGATGGTCAGGCCTACGTTCGCAAGGATGGAGAGTGGGTACTGCTGTCTACTTTCCTG*AGTAC
TACTAAT<u>CTCATTACCTATATCGCTTTAACTGCCATATCTCTTGTTTGCGGTATACTTAGTCTGGTTCTAG</u>
<u>CATGCTACCTAATGTACAAGCAAAAGGCGCAACAAAAGACCTTGTTATGGCTTGGGAATAATACCCTG</u>
<u>GGTCAGATGAGAGCCACTACAAAAATGTGA</u>

FIG. 18B SC-DM F/F Protein Sequence (SEQ ID NO:10)

MELLILKANAITTILTAVTFCFASGQNITEEFYQSTCSAVSKGYLSALRTGWYTSVITIELSNIKE<u>I</u>KCNGTDAKVK
LIKQELDKYKNAVTELQLLMQSTPATNN<u>Q</u>AR*GSGSGR*<u>S</u>LGFLLGVGSAIASGVAVSKVLHLEGEVNKIKSALLS
TNKAVVSLSNGVSVLTSKVLDLKNYIDKQLLPIVNKQSCRI<u>P</u>NIETVIEFQQKNNRLLEITREFSVNAGVTTPVST
YMLTNSELLSLINDMPITNDQKKLMSNNVQIVRQQSYSIMSIIKEEVLAYVVQLPLYGVIDTPCWKLHTSPLCT
TNTKEGSNICLTRTDRGWYCDNAGSVSFFPQAETCKVQSNRVFCDTMNSLTLPSEVNLCNVDIFNPKYDCKI
MTSKTDVSSSVITSLGAIVSCYGKTKCTASNKNRGIIKTFSNGCDYVSNKGVDTVSVGNTLYYVNKQEGKSLYV
KGEPIINFYDPLVFPSDEFDASISQVNEKINQSLAFIRKSDELLHNVNAGK*GYIPEAPRDGQAYVRKDGEWVL*
*LSTFL*STTN<u>LITYIALTAISLVCGILSLVLACYLMYKQKAQQKTLLWLGNNTLGQMRATTKM</u>*

FIG. 19A SC-TM F/F DNA Sequence (SEQ ID NO:11)

ATGGAGCTGCTGATCCTGAAGGCCAACGCCATCACCACCATCCTGACCGCCGTGACCTTCTGCTTCGCCA
GCGGCCAGAACATTACCGAGGAGTTCTACCAGAGCACCTGCAGCGCCGTGAGCAAGGGCTACCTGAGC
GCCCTGAGAACCGGCTGGTACACCAGCGTGATCACCATCGAGCTGAGCAACATCAAGGAG<u>ATT</u>AAGTG
CAACGGCACCGACGCCAAGGTGAAGCTGATCAAGCAGGAGCTGGACAAGTACAAGAACGCCGTGACC
GAGCTGCAGCTGCTGATGCAGAGCACCCCCGCCACCAACAAC*CAG*GCCAGG*GGGTCAGGGTCAGGA*A
GG*TCC*CTGGGCTTCCTGCTGGGAGTGGGCTCCGCCATCGCTTCCGGAGTGGCCGTGAGCAAGGTCCTGC
ACCTGGAGGGCGAGGTCAATAAGATCAAGTCCGCCCTCCTGAGCACCAATAAGGCCGTCGTGAGCCTCA
GCAATGGCGTGAGCGTGCTGACATCCAAGGTCCTCGACCTGAAGAACTACATCGACAAGCAGCTGCTCC
CTATCGTGAACAAACAGAGCTGCAGGATC<u>CCC</u>AACATCGAGACCGTGATCGAGTTCCAGCAGAAGAACA
ACAGGCTGCTGGAGATCACCAGGGAATTTAGCGTGAACGCCGGAGTGACCACCCCCGTGAGCACCTAT
ATGCTGACAAACAGCGAGCTGCTGTCCCTGATCAACGACATGCCCATCACCAACGACCAGAAGAAGCTG
ATGAGCAATAACGTGCAGATCGTGAGGCAGCAGAGCTACAGCATCATGTCCATCATCAAGGAGGAGGT
CCTGGCTTACGTGGTCCAACTGCCTCTGTACGGCGTGATCGACACCCCTTGCTGGAAGCTGCACACAAGC
CCCCTGTGTACCACCAATACCAAGGAGGGCAGCAACATCTGCCTGACAAGGACCGACAGAGGCTGGTA
CTGCGACAATGCCGGCTCCGTGTCCTTCTTTCCCCAGGCTGAGACCTGCAAGGTCCAGAGCAACAGGGT
GTTCTGCGACACCATGAACTCCCTGACCCTCCCCAGCGAGGTGAACCTGTGCAACGTCGACATCTTCAAC
CCCAAGTACGATTGTAAGATCATGACCAGCAAAACCGACGTGAGCAGCAGCGTGATCACCTCCCTGGGC
GCCATCGTGAGCTGCTACGGCAAGACCAAGTGTACCGCCTCCAACAAGAATAGGGGAATCATTAAGACC
TTCTCCAACGGCTGCGACTACGTCTCCAACAAGGGCGTGGACACAGTGTCCGTGGGCAACACCCTGTAC
TACGTGAATAAGCAGGAGGGCAAGAGCCTGTACGTGAAGGGAGAGCCTATCATCAACTTTTACGACCC
CCTGGTGTTCCCTAGC<u>AAC</u>GAGTTCGACGCCAGCATCAGCCAGGTGAACGAGAAGATCAACCAGAGCCT
GGCCTTCATCAGAAAGTCCGACGAGCTCCTCCATAACGTCAACGCCGGGAAA***GGATATATCCCCGAAGC
TCCTCGGGATGGTCAGGCCTACGTTCGCAAGGATGGAGAGTGGGTACTGCTGTCTACTTTCCTG***AGTAC
TACTAAT<u>CTCATTACCTATATCGCTTTAACTGCCATATCTCTTGTTTGCGGTATACTTAGTCTGGTTCTAG
CATGCTACCTAATGTACAAGCAAAAGGCGCAACAAAAGACCTTGTTATGGCTTGGGAATAATACCCTG
GGTCAGATGAGAGCCACTACAAAAATGTGA</u>

FIG. 19B SC-TM F/F Protein Sequence (SEQ ID NO:12)

MELLILKANAITTILTAVTFCFASGQNITEEFYQSTCSAVSKGYLSALRTGWYTSVITIELSNIKE<u>I</u>KCNGTDAKVK
LIKQELDKYKNAVTELQLLMQSTPATNN*Q*AR*GSGSGR*S***LGFLLGVGSAIASGVAVSKVLHLEGEVNKIKSALLS
TNKAVVSLSNGVSVLTSKVLDLKNYIDKQLLPIVNKQSCRI*P*NIETVIEFQQKNNRLLEITREFSVNAGVTTPVST
YMLTNSELLSLINDMPITNDQKKLMSNNVQIVRQQSYSIMSIIKEEVLAYVVQLPLYGVIDTPCWKLHTSPLCT
TNTKEGSNICLTRTDRGWYCDNAGSVSFFPQAETCKVQSNRVFCDTMNSLTLPSEVNLCNVDIFNPKYDCKI
MTSKTDVSSSVITSLGAIVSCYGKTKCTASNKNRGIIKTFSNGCDYVSNKGVDTVSVGNTLYYVNKQEGKSLYV
KGEPIINFYDPLVFPS<u>N</u>EFDASISQVNEKINQSLAFIRKSDELLHNVNAGK***GYIPEAPRDGQAYVRKDGEWVL
LSTFL***STTN<u>LITYIALTAISLVCGILSLVLACYLMYKQKAQQKTLLWLGNNTLGQMRATTKM</u>*

A) FIGURE 20A CMV IE, CAG Promoter Sequence (SEQ ID NO:14)

TAGTAATCAATTACGGGGTCATTAGTTCATAGCCCATATATGGAGTTCCGCGTTACATAACTTACGGTAAATGGCC
CGCCTGGCTGACCGCCCAACGACCCCCGCCCATTGACGTCAATAATGACGTATGTTCCCATAGTAACGCCAATAGG
GACTTTCCATTGACGTCAATGGGTGGAGTATTTACGGTAAACTGCCCACTTGGCAGTACATCAAGTGTATCATATG
CCAAGTACGCCCCCTATTGACGTCAATGACGGTAAATGGCCCGCCTGGCATTATGCCCAGTACATGACCTTATGGG
ACTTTCCTACTTGGCAGTACATCTACGTATTAGTCATCGCTATTACCATGGTCGAGGTGAGCCCCACGTTCTGCTTC
ACTCTCCCCATCTCCCCCCCCTCCCCACCCCCAATTTTGTATTTATTTATTTTTAATTATTTTGTGCAGCGATGGGGG
CGGGGGGGGGGGGGGGCGCGCGCCAGGCGGGGCGGGGCGGGGCGAGGGGCGGGGCGGGGCGAGGCGGA
GAGGTGCGGCGGCAGCCAATCAGAGCGGCGCGCTCCGAAAGTTTCCTTTTATGGCGAGGCGGCGGCGGCGGCG
GCCCTATAAAAAGCGAAGCGCGCGGCGGGCG

B) FIGURE 20B pCaggs Sequence in BacMam Virus (SEQ ID NO:15)

GTCGACATTGATTATTGACTAGTTATTAA<u>TAGTAATCAATTACGGGGTCATTAGTTCATAGCCCATATATGGAGTT
CCGCGTTACATAACTTACGGTAAATGGCCCGCCTGGCTGACCGCCCAACGACCCCCGCCCATTGACGTCAATAAT
GACGTATGTTCCCATAGTAACGCCAATAGGGACTTTCCATTGACGTCAATGGGTGGAGTATTTACGGTAAACTG
CCCACTTGGCAGTACATCAAGTGTATCATATGCCAAGTACGCCCCCTATTGACGTCAATGACGGTAAATGGCCCG
CCTGGCATTATGCCCAGTACATGACCTTATGGGACTTTCCTACTTGGCAGTACATCTACGTATTAGTCATCGCTAT
TACCATGGTCGAGGTGAGCCCCACGTTCTGCTTCACTCTCCCCATCTCCCCCCCCTCCCCACCCCCAATTTTGTATTT
ATTTATTTTTAATTATTTTGTGCAGCGATGGGGGCGGGGGGGGGGGGGGGCCCCCCCAGGCGGGGCGGGG
CGGGGCGAGGGGCGGGGCGGGGCGAGGCGGAAAGGTGCGGCGGCAGCCAATCAGAGCGGCGCGCTCCGAAA
GTTTCCTTTTATGGCGAGGCGGCGGCGGCGGCGGCCCTATAAAAAGCGAAGCGCGCGGCGGGCG</u>GGAGTCGTT
GCGCGCTGCCTTCCCCCGTGCCCCGCTCCGCCGCCGCCTCGCGCCGCCCGCCCCGGCTCTGACTGACCGCGTTAC
TCCCACAGGTGAGCGGGCGGGACGGCCCTTCTCCTCCGGGCTGTAATTAGCGCTTGGTTTAATGACGGCTTGTTTC
TTTTCTGTGGCTGCGTGAAAGCCTTGAGGGGCTCCGGGAGGGCCCTTTGTGCGGGGGGAGCGGCTCGGGGGGTG
CGTGCGTGTGTGTGCGTGGGGAGCGCCGCGTGCGGCTCCGCGCTGCCCGGCGGCTGTGAGCGCTGCGGGCGC
GGCGCGGGGCTTTGTGCGCTCCGCAGTGTGCGCGAGGGGAGCGCGGCCGGGGCGGTGCCCCGCGGTGCGGG
GGGGGCTGCAGGGGAACAAAGGCTGCGTGCGGGTGTGTGCGTGGGGGGGTGAGCAGGGGTGTGGGCGC
GTCGGTCGGGCTGCAACCCCCCCTGCACCCCCCTCCCCGAGTTGCTGAGCACGGCCCGGCTTCGGGTGCGGGCT
CCGTACGGGGCGTGGCGCGGGGCTCGCCGTGCCGGGCGGGGGTGGCGGCAGGTGGGGGTGCCGGGCGGGGC
GGGGCCGCCTCGGGCCGGGGAGGGCTCGGGGGAAGGGGCGCGGCGGCCCCCGGAGCGCCGGCGGCTGTCGAG
GCGCGGCGAGCCGCAGCCATTGCCTTTTATGGTAATCGTGCGAGAGGGCGCAGGGACTTCCTTTGTCCCAAATCT
GTGCGGAGCCGAAATCTGGGAGGCGCCGCCGCACCCCCTCTAGCGGGCGCGGGGCGAAGCGGTGCGGCGCCGG
CAGGAAGGAAATGGGCGGGAGGGCCTTCGTGCGTCGCCGCGCCGCCGTCCCCTTCTCCCTCTCCAGCCTCGGGG
CTGTCCGCGGGGGACGGCTGCCTTCGGGGGGACGGGGCAGGGCGGGGTTCGGCTTCTGGCGTGTGACCGGC
GGCTCTAGAGCCTCTGCTAACCATGTTCATGCCTTCTTCTTTTTCCTACAGCTCCTGGGCAACGTGCTGGTTATTGTG
CTGTCTCATCATTTTGGCAAAGAATTC*<u>CTCGAGGAATTCACTCCTCAGGTGCAGGCTGCCTATCAGAAGGTGGTG
GCTGGTGTGGCCA</u>*ATGCCCTGGCTCACAAATACCACTGAGATCT

FIG. 21A NDV NP Protein Sequence (SEQ ID NO:16)

MSSVFDEYEQLLAAQTRPNGAHGGGEKGSTLKVEVPVFTLNSDDPEDRWNFVVFCLRIAVSEDANKPLRQG
ALISLLCSHSQVMRNHVALAGKQNEATLAVLEIDGFTNSVPQFNNTSGVSEERAQRFMMIAGSLPRACSNG
TPFITAGVEDDAPEDIIDTLERILSIQAQVWVTVAKAMTAYETADESETRRINKYMQQGRVQKKYILHPVCRS
AIQLTIRQSLAVRIFLVSELKRGRNHAGGSSTYYNLVGDVDSYIRNTGLTAFFLTLKYGINTKTSALALSSLAGDI
QKMKQLMRLYRMKGDNAPYMTLLGDSDQMSFAPAEYAQLYSFAMAMASVLDKGTGKYQFARDFMSTSF
WRLGVEYAQAQGSSINEDMAAELKLTPAARRGLAAAAQRVSEETSSMDIPTQQAGVLTGLSDGGPQAPQG
GSNRSQGRPDAGDGETQFLDLMRAVANSMREAPNSVQSTTQPEPPPTPGPSQDNDTDWGY*

FIG. 21B NDV M Protein Sequence (SEQ ID NO:17)

MDSSRTIGLYFDSALPSSNLLAFPIVLQDIGDGKKQIAPQYRIQRLDSWTDSKEDSVFITTYGFIFQVGNEEVTV
GMISDNPKHELLSAAMLCLGSVPNVGDLVELARACLTMVVTCKKSATDTERMVFSVVQAPQVLQSCRVVA
NKYSSVNAVKHVKAPEKIPGSGTLEYKVNFVSLTVVPRKDVYKIPTAALKVSGSSLYNLALNVTIDVEVDPKSPL
VKSLSKSDSGYYANLFLHIGLMSTVDKKGKKVTFDKLERKIRRLDLSVGLSDVLGPSVLKARGARTRLLAPFFS
SSGTACYPISNASPQVAKILWSQTARLRSVKVIIQAGTQRAVAVTADHEVTSTKIEKRHTIAKYNPFKK*

FIG. 21C  H/G (NDV HN/RSV G) Protein Sequence (SEQ ID NO:18)

<u>MNRAVCQVALENDEREAKNTWRLVFRIAILLLTVMTLAISAAALAYS</u>ANHKVTPTTAIIQDATSQIKNTTPT
YLTQNPQLGISPSNPSEITSQITTILASTTPGVKSTLQSTTVKTKNTTTTQTQPSKPTTKQRQNKPPSKPNNDFH
FEVFNFVPCSICSNNPTCWAICKRIPNKKPGKKTTTKPTKKPTLKTTKKDPKPQTTKSKEVPTTKPTEEPTINTTK
TNIITTLLTSNTTGNPELTSQMETFHSTSSEGNPSPSQVSTTSEYPSQPSSPPNTPRQ*

FIG. 21D  SC-TM F/F Protein Sequence (SEQ ID NO:19)

MELLILKANAITTILTAVTFCFASGQNITEEFYQSTCSAVSKGYLSALRTGWYTSVITIELSNIKE<u>I</u>KCNGTDAKVK
LIKQELDKYKNAVTELQLLMQSTPATNN<u>*QAR*</u><u>*GSGSG*</u><u>*R*</u><u>*S*</u>LGFLLGVGSAIASGVAVSKVLHLEGEVNKIKSALLS
TNKAVVSLSNGVSVLTSKVLDLKNYIDKQLLPIVNKQSCRI<u>P</u>NIETVIEFQQKNNRLLEITREFSVNAGVTTPVST
YMLTNSELLSLINDMPITNDQKKLMSNNVQIVRQQSYSIMSIIKEEVLAYVVQLPLYGVIDTPCWKLHTSPLCT
TNTKEGSNICLTRTDRGWYCDNAGSVSFFPQAETCKVQSNRVFCDTMNSLTLPSEVNLCNVDIFNPKYDCKI
MTSKTDVSSSVITSLGAIVSCYGKTKCTASNKNRGIIKTFSNGCDYVSNKGVDTVSVGNTLYYVNKQEGKSLYV
KGEPIINFYDPLVFPS<u>N</u>EFDASISQVNEKINQSLAFIRKSDELLHNVNAGK*GYIPEAPRDGQAYVRKDGEWVL*
*LSTFL*STTN<u>LTYIALTAISLVCGILSLVLACYLMYKQKAQQKTLLWLGNNTLGQMRATTKM</u>*

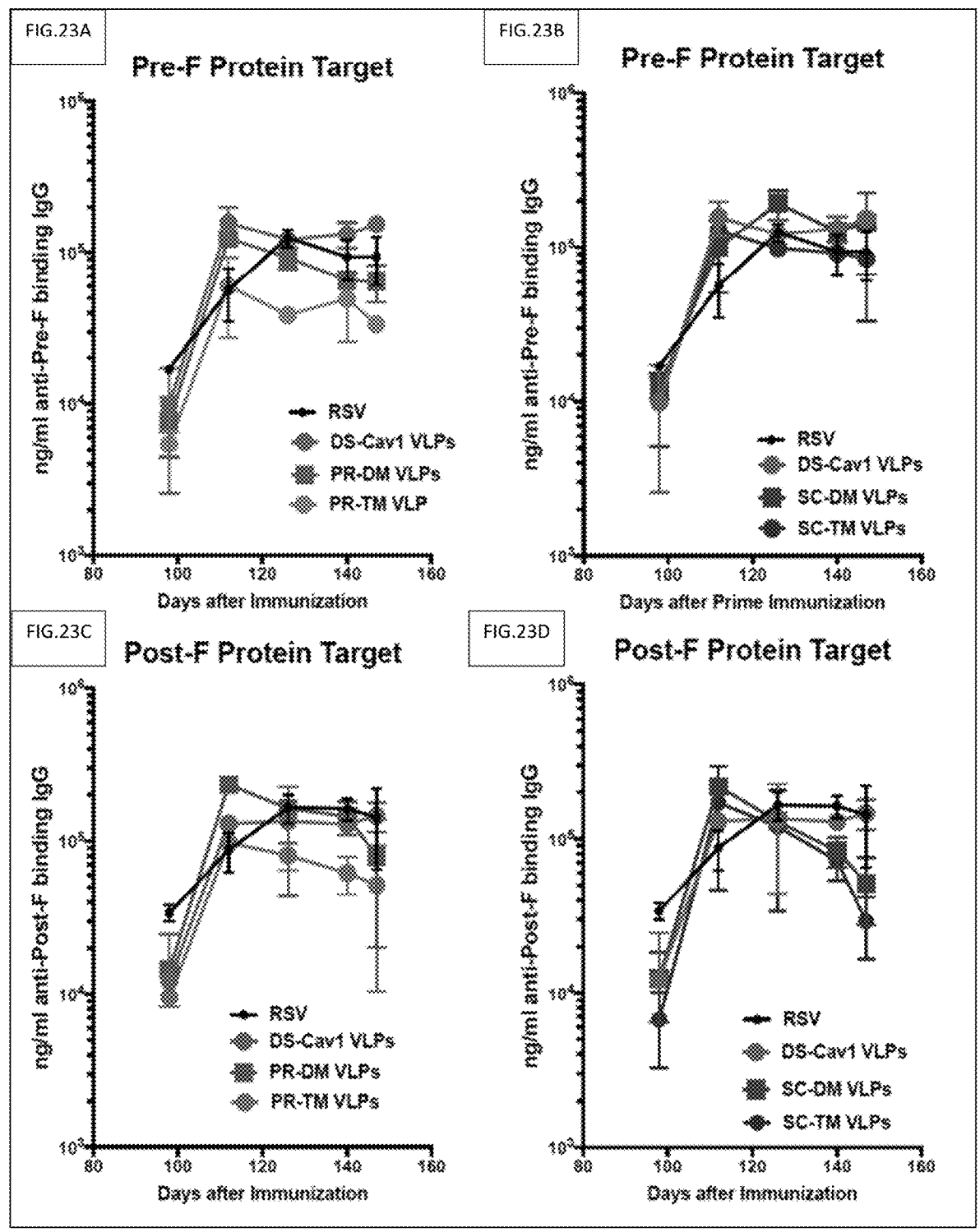

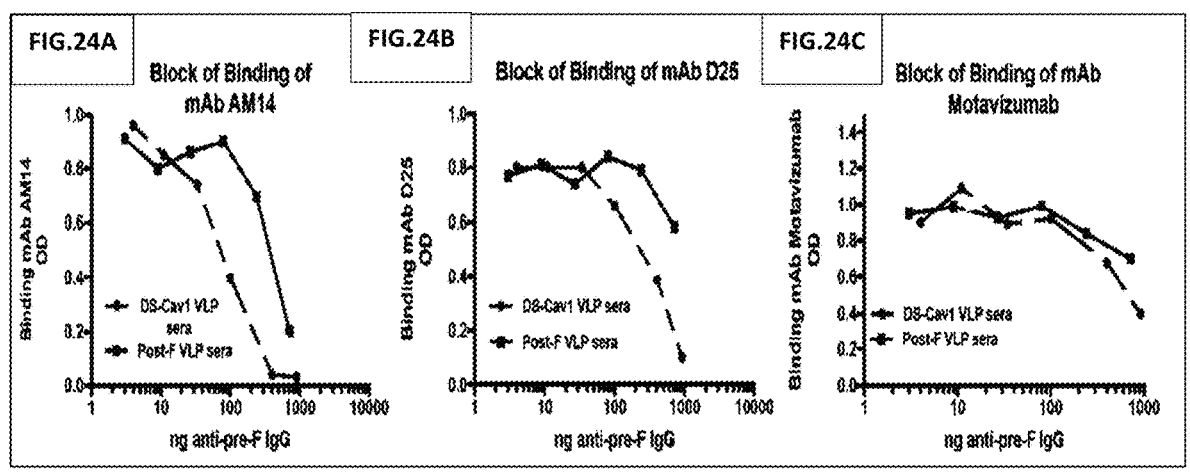

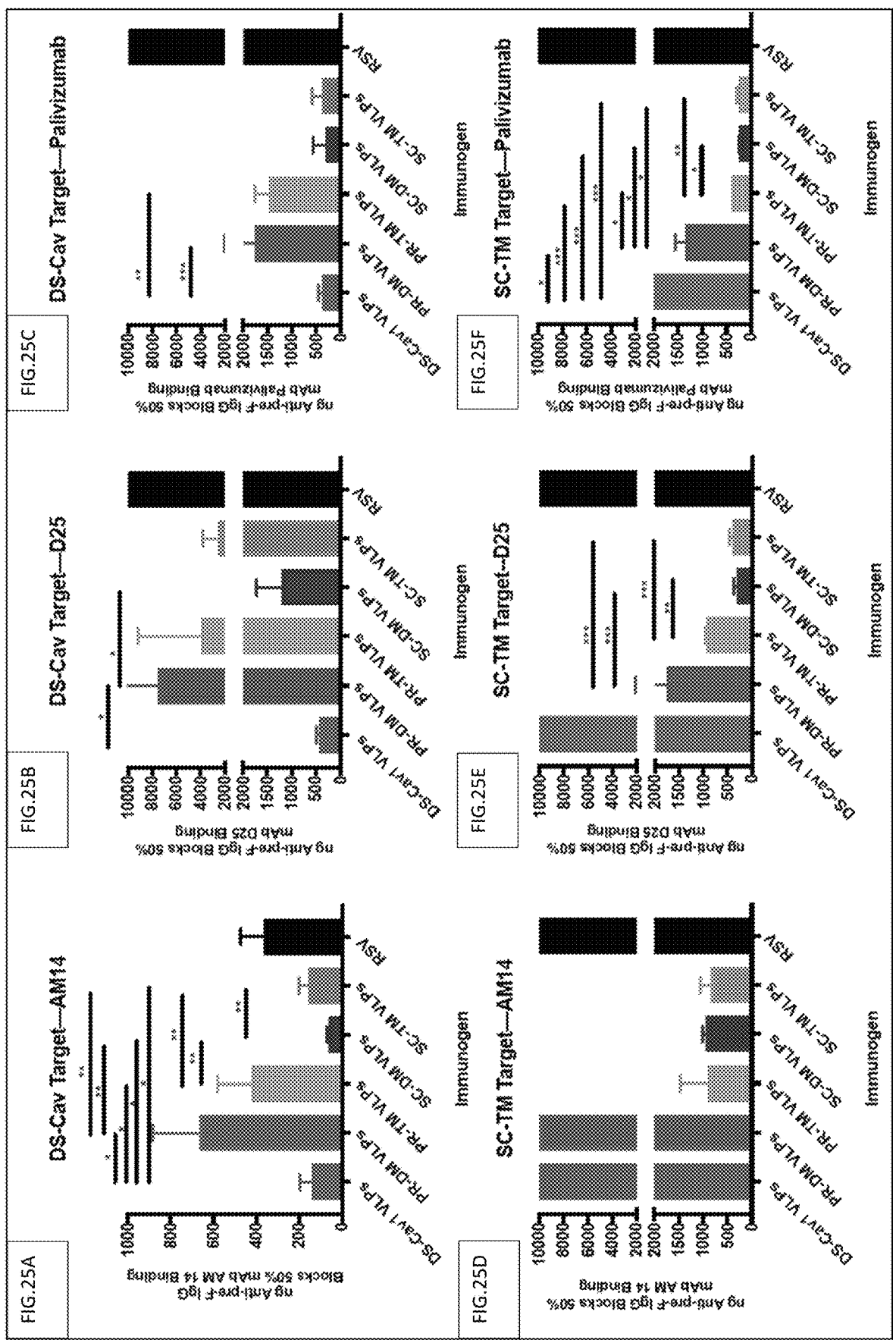

ANTI-NVD F TAIL

ANTI-RSV G

ANTI-NDV

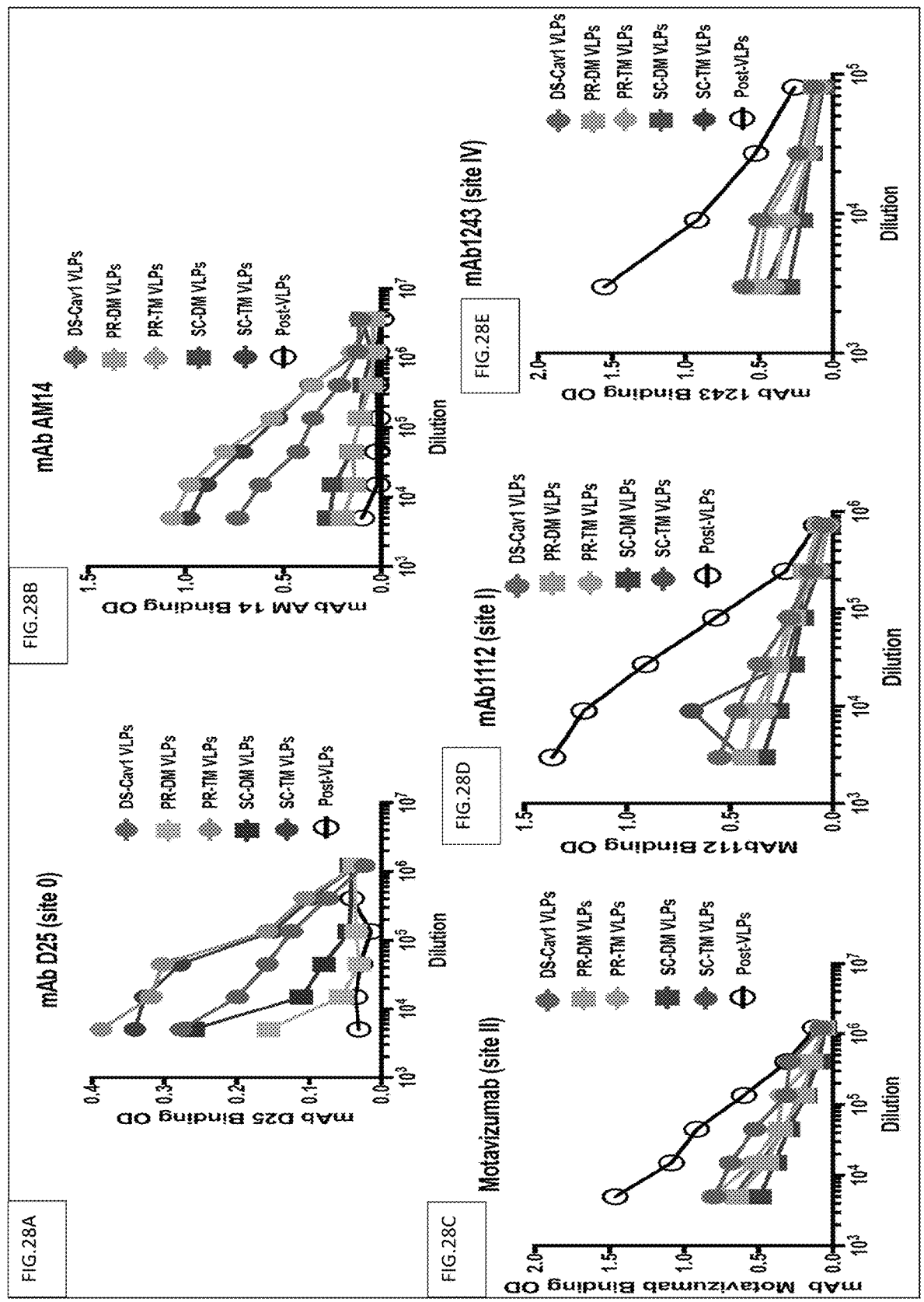

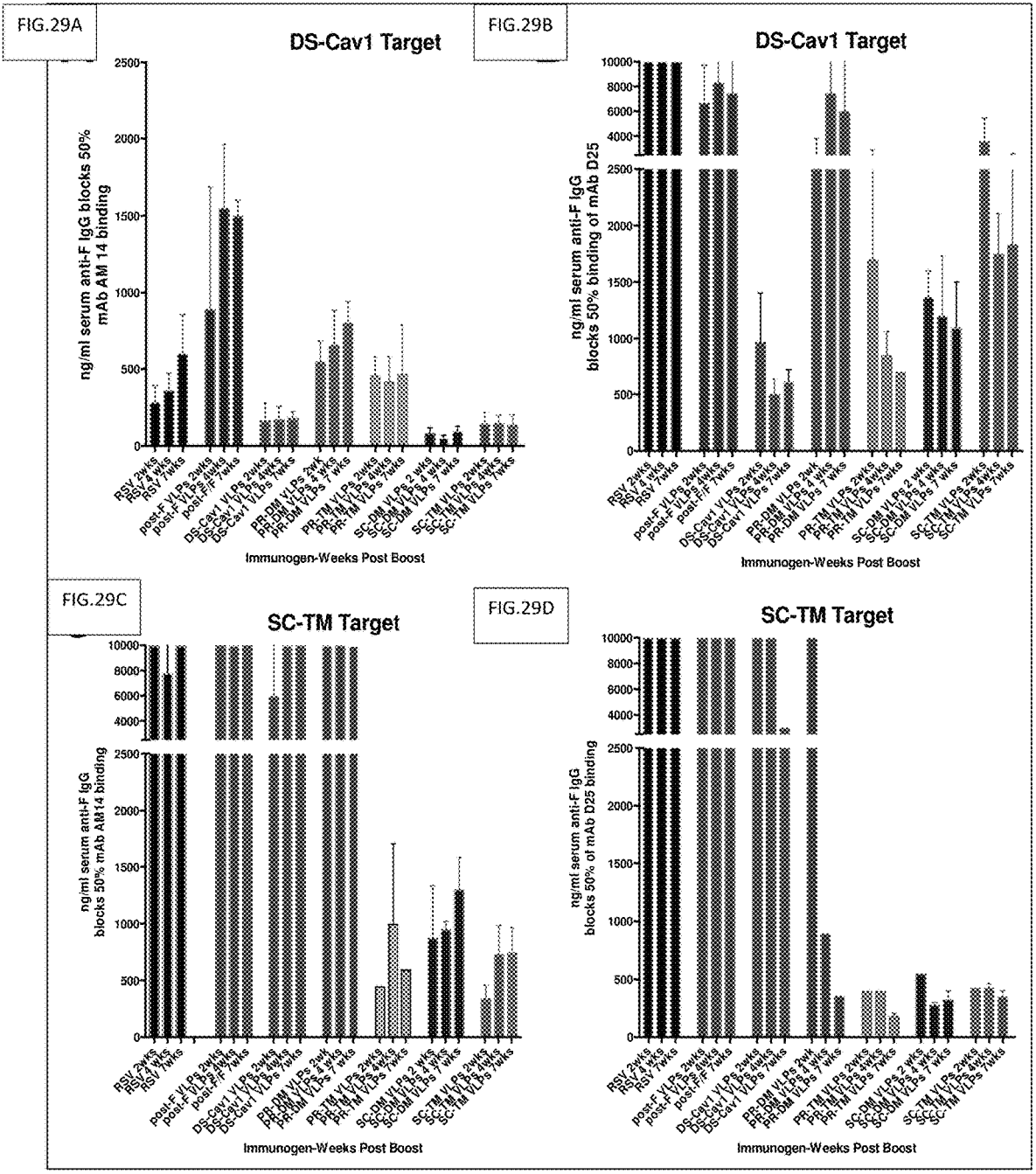

SEQUENCE LISTING

<160> NUMBER OF SEQ ID NOS: 19

<210> SEQ ID NO 1
<211> LENGTH: 1704
<212> TYPE: DNA
<213> ORGANISM: Artificial Sequence
<220> FEATURE:
<223> OTHER INFORMATION: Synthetic

<400> SEQUENCE: 1

```
atggagcttc ttattctcaa agccaatgct attactacca tcctgacagc cgtgacattt      60
tgcttcgcca gtggacagaa tatcactgag gaattctatc agagcacctg ttccgctgta     120
tcaaaagggt atctctccgc attacgaacc ggatggtaca cttcagtcat cacaattgaa     180
ctttctaaca ttaaagagaa taagtgtaac gggactgacg ctaaagtgaa gttgataaag     240
caggagctag acaaatataa gaatgcagta actgaacttc agttgcttat gcagtccaca     300
cctgctacta acaatagagc acgccgtgaa ctgcctagat tcatgaacta tactcttaat     360
aacgcaaaaa agactaatgt tacccttttcc aagaaacaga aacagcaagc tattgcttca     420
ggagtagcag taagtaaggt attacatttg gaaggcgaag tgaacaaaat taaatcagca     480
ctgctttcca ctaacaaggc agtagtgagt ctgtctaatg gtgttagcgt tttaacttct     540
aaagtgctgg atttaaagaa ctacatcgat aaacagctgc tccccatcgt aaacaagcag     600
agttgccgta tcagcaacat agagacagtg atagagtttc agcagaagaa caataggctg     660
cttgaaataa ctcgcgaatt tagcgttaac gcaggcgtga ctaccccagt gtccacttat     720
atgctgacaa actcagagtt actttctctg atcaacgaca tgccaataac taatgatcag     780
aagaaattaa tgtctaataa cgtgcagata gttcggcagc agtcctacag tatcatgagc     840
attatcaagg aagaggtatt ggcctatgtc gttcagttac ctttatacgg tgttatcgat     900
accccatgtt ggaagctcca taccagcccc ttgtgtacta ccaatactaa agaggggagc     960
aatatttgtc taactaggac cgatagggc tggtactgcg acaacgcagg gagtgtttct    1020
ttctttcctc aggcagaaac atgcaaggtg cagagcaaca gagtgttttg cgatactatg    1080
aatagcctga ctctgccatc cgaagttaat ctgtgtaacg tcgatatatt taatccaaaa    1140
tacgattgca aaatcatgac ttcaaaaaca gacgtgagca gttcagtcat aacttctcta    1200
```

```
ggtgccattg tttcatgcta cggaaaaact aagtgtaccg ctagcaacaa aaacagaggt    1260
attatcaaga ctttctccaa tggctgcgat tacgtttcca acaagggtgt cgatacagtc    1320
tcagtcggga ataccttata ttacgttaat aaacaggagg ggaagtctct gtatgtgaaa    1380
ggtgagccaa taattaattt ttatgatcct ttagtatttc catctgacga gtttgacgca    1440
tccatttctc aggttaacga aaagatcaac cagagcttgg cttttataag gaagagtgac    1500
gagctcctcc ataacgtcaa cgccgggaaa agtactacta atctcattac ctatatcgct    1560
ttaactgcca tatctcttgt ttgcggtata cttagtctgg ttctagcatg ctacctaatg    1620
tacaagcaaa aggcgcaaca aaagaccttg ttatggcttg ggataatac cctgggtcag    1680 atgagagcca ctacaaaaat gtga                                          1704
```

<210> SEQ ID NO 2
<211> LENGTH: 567
<212> TYPE: PRT
<213> ORGANISM: Artificial Sequence
<220> FEATURE:
<223> OTHER INFORMATION: Synthetic

<400> SEQUENCE: 2

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Gln Lys Gln Gln Ala Ile Ala Ser Gly Val Ala Val
    130                 135                 140

Ser Lys Val Leu His Leu Glu Gly Glu Val Asn Lys Ile Lys Ser Ala
145                 150                 155                 160

Leu Leu Ser Thr Asn Lys Ala Val Val Ser Leu Ser Asn Gly Val Ser
                165                 170                 175

Val Leu Thr Ser Lys Val Leu Asp Leu Lys Asn Tyr Ile Asp Lys Gln
            180                 185                 190

Leu Leu Pro Ile Val Asn Lys Gln Ser Cys Arg Ile Ser Asn Ile Glu
        195                 200                 205

Thr Val Ile Glu Phe Gln Gln Lys Asn Asn Arg Leu Leu Glu Ile Thr
    210                 215                 220

Arg Glu Phe Ser Val Asn Ala Gly Val Thr Thr Pro Val Ser Thr Tyr
225                 230                 235                 240

Met Leu Thr Asn Ser Glu Leu Leu Ser Leu Ile Asn Asp Met Pro Ile
                245                 250                 255

Thr Asn Asp Gln Lys Lys Leu Met Ser Asn Asn Val Gln Ile Val Arg
            260                 265                 270
```

```
Gln Gln Ser Tyr Ser Ile Met Ser Ile Ile Lys Glu Glu Val Leu Ala
            275                 280                 285

Tyr Val Val Gln Leu Pro Leu Tyr Gly Val Ile Asp Thr Pro Cys Trp
            290                 295                 300

Lys Leu His Thr Ser Pro Leu Cys Thr Thr Asn Thr Lys Glu Gly Ser
305                 310                 315                 320

Asn Ile Cys Leu Thr Arg Thr Asp Arg Gly Trp Tyr Cys Asp Asn Ala
                325                 330                 335

Gly Ser Val Ser Phe Phe Pro Gln Ala Glu Thr Cys Lys Val Gln Ser
            340                 345                 350

Asn Arg Val Phe Cys Asp Thr Met Asn Ser Leu Thr Leu Pro Ser Glu
            355                 360                 365

Val Asn Leu Cys Asn Val Asp Ile Phe Asn Pro Lys Tyr Asp Cys Lys
370                 375                 380

Ile Met Thr Ser Lys Thr Asp Val Ser Ser Ser Val Ile Thr Ser Leu
385                 390                 395                 400

Gly Ala Ile Val Ser Cys Tyr Gly Lys Thr Lys Cys Thr Ala Ser Asn
                405                 410                 415

Lys Asn Arg Gly Ile Ile Lys Thr Phe Ser Asn Gly Cys Asp Tyr Val
            420                 425                 430

Ser Asn Lys Gly Val Asp Thr Val Ser Val Gly Asn Thr Leu Tyr Tyr
            435                 440                 445

Val Asn Lys Gln Glu Gly Lys Ser Leu Tyr Val Lys Gly Glu Pro Ile
            450                 455                 460

Ile Asn Phe Tyr Asp Pro Leu Val Phe Pro Ser Asp Glu Phe Asp Ala
465                 470                 475                 480

Ser Ile Ser Gln Val Asn Glu Lys Ile Asn Gln Ser Leu Ala Phe Ile
                485                 490                 495

Arg Lys Ser Asp Glu Leu Leu His Asn Val Asn Ala Gly Lys Ser Thr
            500                 505                 510

Thr Asn Leu Ile Thr Tyr Ile Ala Leu Thr Ala Ile Ser Leu Val Cys
            515                 520                 525

Gly Ile Leu Ser Leu Val Leu Ala Cys Tyr Leu Met Tyr Lys Gln Lys
530                 535                 540

Ala Gln Gln Lys Thr Leu Leu Trp Leu Gly Asn Asn Thr Leu Gly Gln
545                 550                 555                 560

Met Arg Ala Thr Thr Lys Met
                565

<210> SEQ ID NO 3
<211> LENGTH: 1815
<212> TYPE: DNA
<213> ORGANISM: Artificial Sequence
<220> FEATURE:
<223> OTHER INFORMATION: Synthetic

<400> SEQUENCE: 3
atggagctgc tgatcctgaa ggccaacgcc attaccacca ttctgacagc cgtgacattc      60
tgcttcgcct ccggacagaa catcacagag gagttctatc agagcaccct gttccgccgtc    120 tccaaaggat atctgagcgc cctgaggacc ggctggtata cctccgtgat caccatcgag     180
cttagcaaca tcaaggagaa caagtgcaat ggcaccgacg ccaaggtcaa gctcatcaag     240
caagagcttg acaagtacaa aaacgccgtc accgagcttc agctgctgat gcagtccaca     300
ccagctacca caacagagc caggagagag cttcccagat tcatgaacta caccctgaac     360
```

```
aacgccaaga agaccaacgt gaccctgtcc aagaaaagga aaaggaggtt cctgggcttc    420
ctcctgggag tgggatccgc catcgctagc ggcgtggccg tctgtaaagt cctccatctg    480
gaaggcgagg tcaacaagat caaaagcgcc ctgctgtcca aaacaaagc tgtggtctcc     540 ctgagcaacg gcgtcagcgt cctgaccttc aaggtgctcg acctcaagaa ctacatcgac    600
aagcaactgc tccccatcct caacaagcag agctgcagga tcagcaacat tgaaaccgtg    660
atcgagttcc agcagaagaa taacaggctc ctggagatca ccagggagtt cagcgtgaat    720
gctggcgtga caaccccgt ctccacctac atgctgacca cagcgaact cctgagcctg       780 atcaacgata tgcccatcac caacgaccag aagaagctca tgagcaacaa cgtccagatc    840
gtgaggcagc agagctacag catcatgtgc attatcaaag aggaggtcct ggcttacgtg    900
gtccagctgc ccctgtatgg agtcattgac acccctgct ggaaactcca taccagccca     960
ctgtgtacaa ccaacaccaa ggagggcagc aacatctgcc tcaccagaac cgataggggc   1020
tggtactgcg acaacgccgg atccgtgagc ttcttcccc aggccgagac ctgcaaggtc    1080
cagagcaaca gggtcttctg cgataccatg aacagcctca ccctgccctc cgaggtgaat   1140
ctctgtaatg tcgacatctt caatccaaag tacgactgta agatcatgac cagcaagacc   1200
gacgtcagca gcagcgtgat taccagcctc ggagccatcg tgagctgtta cggcaagacc   1260
aagtgcaccg ccagcaacaa gaacagagga attatcaaga ccttcagcaa cggatgcgac   1320
tacgtctcca caaaggcgt ggataccgtc tccgtgggca cacccctgta ctacgtcaac     1380
aagcaggaag gcaaaagcct gtacgtcaag ggcgagccaa tcatcaactt ttacgatccc   1440
ctcgtcttcc catccgatga gttcgacgcc agcatctccc aagtcaacga aagatcaac    1500 cagtccctgg ccttcatcag aaagtccgac gagctcctcc ataacgtcaa cgccgggaaa   1560
ggatatatcc ccgaagctcc tcgggatggt caggcctacg ttcgcaagga tggagagtgg   1620
gtactgctgt ctactttcct gagtactact aatctcatta cctatatcgc tttaactgcc   1680
atatctcttg tttgcggtat acttagtctg gttctagcat gctacctaat gtacaagcaa   1740
aaggcgcaac aaaagacctt gttatggctt gggaataata ccctgggtca gatgagagcc   1800
actacaaaaa tgtga                                                    1815
```

<210> SEQ ID NO 4
<211> LENGTH: 604
<212> TYPE: PRT
<213> ORGANISM: Artificial Sequence
<220> FEATURE:
<223> OTHER INFORMATION: Synthetic

<400> SEQUENCE: 4

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
```

```
              100                 105                 110
Arg Phe Met Asn Tyr Thr Leu Asn Asn Ala Lys Lys Thr Asn Val Thr
            115                 120                 125

Leu Ser Lys Lys Arg Lys Arg Arg Phe Leu Gly Phe Leu Leu Gly Val
        130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Arg Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Gly Tyr Ile Pro Glu Ala Pro Arg
        515                 520                 525
```

```
Asp Gly Gln Ala Tyr Val Arg Lys Asp Gly Glu Trp Val Leu Leu Ser
            530                 535                 540

Thr Phe Leu Ser Thr Thr Asn Leu Ile Thr Tyr Ile Ala Leu Thr Ala
545                 550                 555                 560

Ile Ser Leu Val Cys Gly Ile Leu Ser Leu Val Leu Ala Cys Tyr Leu
                565                 570                 575

Met Tyr Lys Gln Lys Ala Gln Gln Lys Thr Leu Leu Trp Leu Gly Asn
            580                 585                 590

Asn Thr Leu Gly Gln Met Arg Ala Thr Thr Lys Met
            595                 600

<210> SEQ ID NO 5
<211> LENGTH: 1815
<212> TYPE: DNA
<213> ORGANISM: Artificial Sequence
<220> FEATURE:
<223> OTHER INFORMATION: Synthetic

<400> SEQUENCE: 5
atggagctgc tgatcctgaa ggccaacgcc atcaccacca tcctgaccgc cgtgaccttc      60
tgcttcgcca cggccagaa cattaccgag gagttctacc agagcacctg cagcgccgtg     120
agcaagggct acctgagcgc cctgagaacc ggctggtaca ccagcgtgat caccatcgag     180
ctgagcaaca tcaaggagat taagtgcaac ggcaccgacg ccaaggtgaa gctgatcaag     240
caggagctgg acaagtacaa gaacgccgtg accgagctgc agctgctgat gcagagcacc     300
cccgccacca caacagggc caggaggag ctgcccaggt tcatgaacta caccctgaac     360
aacgccaaga gaccaacgt gaccctgagc aagaagagga gaggaggtt cctgggcttc     420 ctgctgggag tgggctccgc catcgcttcc ggagtggccg tgagcaaggt cctgcacctg     480
gagggcgagg tcaataagat caagtccgcc ctcctgagca ccaataaggc cgtcgtgagc     540
ctcagcaatg gcgtgagcgt gctgacatcc aaggtcctcg acctgaagaa ctacatcgac     600
aagcagctgc tccctatcgt gaacaaacag agctgcagga tccccaacat cgagaccgtg     660
atcgagttcc agcagaagaa caacaggctg ctggagatca ccagggaatt tagcgtgaac     720
gccggagtga ccacccccgt gagcacctat atgctgacaa cagcgagct gctgtccctg     780 atcaacgaca tgcccatcac caacgaccag aagaagctga tgagcaataa cgtgcagatc     840
gtgaggcagc agagctacag catcatgtcc atcatcaagg aggaggtcct ggcttacgtg     900
gtccaactgc tctgtacgg cgtgatcgac accccttgct ggaagctgca caagcccc     960 ctgtgtacca ccaataccaa ggagggcagc aacatctgcc tgacaaggac cgacagaggc    1020
tggtactgcg acaatgccgg ctccgtgtcc ttctttcccc aggctgagac ctgcaaggtc    1080
cagagcaaca gggtgttctg cgacaccatg aactccctga ccctcccag cgaggtgaac    1140 ctgtgcaacg tcgacatctt caaccccaag tacgattgta agatcatgac cagcaaaacc    1200
gacgtgagca gcagcgtgat cacctccctg ggcgccatcg tgagctgcta cggcaagacc    1260
aagtgtaccg cctccaacaa gaatagggga atcattaaga ccttctccaa cggctgcgac    1320
tacgtctcca caagggcgt ggacacagtg tccgtgggca cacccgta ctacgtgaat    1380 aagcaggagg gcaagagcct gtacgtgaag ggagagccta tcatcaactt ttacgacccc    1440
ctggtgttcc ctagcgacga gttcgacgcc agcatcagcc aggtgaacga gaagatcaac    1500
cagagcctgg cctttatcag aaagtccgac gagctcctcc ataacgtcaa cgccgggaaa    1560
ggatatatcc ccgaagctcc tcgggatggt caggcctacg ttcgcaagga tggagagtgg    1620
```

```
gtactgctgt ctactttcct gagtactact aatctcatta cctatatcgc tttaactgcc      1680
atatctcttg tttgcggtat acttagtctg gttctagcat gctacctaat gtacaagcaa      1740
aaggcgcaac aaaagacctt gttatggctt gggaataata ccctgggtca gatgagagcc      1800
actacaaaaa tgtga                                                       1815

<210> SEQ ID NO 6
<211> LENGTH: 604
<212> TYPE: PRT
<213> ORGANISM: Artificial Sequence
<220> FEATURE:
<223> OTHER INFORMATION: Synthetic

<400> SEQUENCE: 6

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Ile Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Arg Ile Pro Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320
```

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
        340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu His Asn Val Asn Ala Gly Lys Gly Tyr Ile Pro Glu Ala Pro Arg
        515                 520                 525

Asp Gly Gln Ala Tyr Val Arg Lys Asp Gly Glu Trp Val Leu Leu Ser
    530                 535                 540

Thr Phe Leu Ser Thr Thr Asn Leu Ile Thr Tyr Ile Ala Leu Thr Ala
545                 550                 555                 560

Ile Ser Leu Val Cys Gly Ile Leu Ser Leu Val Leu Ala Cys Tyr Leu
            565                 570                 575

Met Tyr Lys Gln Lys Ala Gln Gln Lys Thr Leu Leu Trp Leu Gly Asn
        580                 585                 590

Asn Thr Leu Gly Gln Met Arg Ala Thr Thr Lys Met
        595                 600

<210> SEQ ID NO 7
<211> LENGTH: 1815
<212> TYPE: DNA
<213> ORGANISM: Artificial Sequence
<220> FEATURE:
<223> OTHER INFORMATION: Synthetic

<400> SEQUENCE: 7
atggagctgc tgatcctgaa ggccaacgcc atcaccacca tcctgaccgc cgtgaccttc      60
tgcttcgcca gcggccagaa cattaccgag gagttctacc agagcaccctg cagcgccgtg    120 agcaagggct acctgagcgc cctgagaacc ggctggtaca ccagcgtgat caccatcgag    180
ctgagcaaca tcaaggagat taagtgcaac ggcaccgacg ccaaggtgaa gctgatcaag    240
caggagctgg acaagtacaa gaacgccgtg accgagctgc agctgctgat gcagagcacc    300
cccgccacca caacagggc caggagggag ctgcccaggt tcatgaacta caccctgaac      360
aacgccaaga gaccaacgt gaccctgagc aagaaggaga gaggaggtt cctgggcttc      420 ctgctgggag tgggctccgc catcgcttcc ggagtggccg tgagcaaggt cctgcacctg    480

```
gagggcgagg tcaataagat caagtccgcc ctcctgagca ccaataaggc cgtcgtgagc      540
ctcagcaatg gcgtgagcgt gctgacatcc aaggtcctcg acctgaagaa ctacatcgac      600
aagcagctgc tccctatcgt gaacaaacag agctgcagga tccccaacat cgagaccgtg      660
atcgagttcc agcagaagaa caacaggctg ctggagatca ccagggaatt tagcgtgaac      720
gccggagtga ccaccccgt gagcacctat atgctgacaa acagcgagct gctgtccctg      780
atcaacgaca tgcccatcac caacgaccag aagaagctga tgagcaataa cgtgcagatc      840
gtgaggcagc agagctacag catcatgtcc atcatcaagg aggaggtcct ggcttacgtg      900
gtccaactgc tctgtacgg cgtgatcgac accccttgct ggaagctgca cacaagcccc       960
ctgtgtacca ccaataccaa ggagggcagc aacatctgcc tgacaaggac cgacagaggc     1020
tggtactgcg acaatgccgg ctccgtgtcc ttctttcccc aggctgagac ctgcaaggtc     1080
cagagcaaca gggtgttctg cgacaccatg aactccctga ccctccccag cgaggtgaac     1140
ctgtgcaacg tcgacatctt caaccccaag tacgattgta agatcatgac cagcaaaacc     1200
gacgtgagca gcagcgtgat cacctccctg gcgccatcg tgagctgcta cggcaagacc     1260
aagtgtaccg cctccaacaa gaataggga atcattaaga ccttctccaa cggctgcgac     1320
tacgtctcca acaagggcgt ggacacagtg tccgtgggca cacccctgta ctacgtgaat     1380
aagcaggagg caagagcct gtacgtgaag gagagccta tcatcaactt ttacgacccc     1440
ctggtgttcc ctagcaacga gttcgacgcc agcatcagcc aggtgaacga agatcaac     1500 cagagcctgg ccttcatcag aaagtccgac gagctcctcc ataacgtcaa cgccgggaaa     1560
ggatatatcc ccgaagctcc tcgggatggt caggcctacg ttcgcaagga tggagagtgg     1620
gtactgctgt ctactttcct gagtactact aatctcatta cctatatcgc tttaactgcc     1680
atatctcttg tttgcggtat acttagtctg gttctagcat gctacctaat gtacaagcaa     1740
aaggcgcaac aaaagacctt gttatggctt gggaataata ccctgggtca gatgagagcc     1800
actacaaaaa tgtga                                                       1815
```

<210> SEQ ID NO 8
<211> LENGTH: 604
<212> TYPE: PRT
<213> ORGANISM: Artificial Sequence
<220> FEATURE:
<223> OTHER INFORMATION: Synthetic

<400> SEQUENCE: 8

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Ile Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
```

```
             115                 120                 125
Leu Ser Lys Lys Arg Lys Arg Arg Phe Leu Gly Phe Leu Leu Gly Val
            130                 135                 140
Gly Ser Ala Ile Ala Ser Gly Val Ala Val Ser Lys Val Leu His Leu
145                 150                 155                 160
Glu Gly Glu Val Asn Lys Ile Lys Ser Ala Leu Leu Ser Thr Asn Lys
                165                 170                 175
Ala Val Val Ser Leu Ser Asn Gly Val Ser Val Leu Thr Ser Lys Val
                    180                 185                 190
Leu Asp Leu Lys Asn Tyr Ile Asp Lys Gln Leu Leu Pro Ile Val Asn
                195                 200                 205
Lys Gln Ser Cys Arg Ile Pro Asn Ile Glu Thr Val Ile Glu Phe Gln
210                 215                 220
Gln Lys Asn Asn Arg Leu Leu Glu Ile Thr Arg Glu Phe Ser Val Asn
225                 230                 235                 240
Ala Gly Val Thr Thr Pro Val Ser Thr Tyr Met Leu Thr Asn Ser Glu
                    245                 250                 255
Leu Leu Ser Leu Ile Asn Asp Met Pro Ile Thr Asn Asp Gln Lys Lys
                260                 265                 270
Leu Met Ser Asn Asn Val Gln Ile Val Arg Gln Gln Ser Tyr Ser Ile
                275                 280                 285
Met Ser Ile Ile Lys Glu Glu Val Leu Ala Tyr Val Val Gln Leu Pro
290                 295                 300
Leu Tyr Gly Val Ile Asp Thr Pro Cys Trp Lys Leu His Thr Ser Pro
305                 310                 315                 320
Leu Cys Thr Thr Asn Thr Lys Glu Gly Ser Asn Ile Cys Leu Thr Arg
                    325                 330                 335
Thr Asp Arg Gly Trp Tyr Cys Asp Asn Ala Gly Ser Val Ser Phe Phe
                340                 345                 350
Pro Gln Ala Glu Thr Cys Lys Val Gln Ser Asn Arg Val Phe Cys Asp
                355                 360                 365
Thr Met Asn Ser Leu Thr Leu Pro Ser Glu Val Asn Leu Cys Asn Val
370                 375                 380
Asp Ile Phe Asn Pro Lys Tyr Asp Cys Lys Ile Met Thr Ser Lys Thr
385                 390                 395                 400
Asp Val Ser Ser Ser Val Ile Thr Ser Leu Gly Ala Ile Val Ser Cys
                    405                 410                 415
Tyr Gly Lys Thr Lys Cys Thr Ala Ser Asn Lys Asn Arg Gly Ile Ile
                420                 425                 430
Lys Thr Phe Ser Asn Gly Cys Asp Tyr Val Ser Asn Lys Gly Val Asp
                435                 440                 445
Thr Val Ser Val Gly Asn Thr Leu Tyr Tyr Val Asn Lys Gln Glu Gly
            450                 455                 460
Lys Ser Leu Tyr Val Lys Gly Glu Pro Ile Ile Asn Phe Tyr Asp Pro
465                 470                 475                 480
Leu Val Phe Pro Ser Asn Glu Phe Asp Ala Ser Ile Ser Gln Val Asn
                    485                 490                 495
Glu Lys Ile Asn Gln Ser Leu Ala Phe Ile Arg Lys Ser Asp Glu Leu
                500                 505                 510
Leu His Asn Val Asn Ala Gly Lys Gly Tyr Ile Pro Glu Ala Pro Arg
                515                 520                 525
Asp Gly Gln Ala Tyr Val Arg Lys Asp Gly Glu Trp Val Leu Leu Ser
            530                 535                 540
```

```
Thr Phe Leu Ser Thr Thr Asn Leu Ile Thr Tyr Ile Ala Leu Thr Ala
545                 550                 555                 560

Ile Ser Leu Val Cys Gly Ile Leu Ser Leu Val Leu Ala Cys Tyr Leu
                565                 570                 575

Met Tyr Lys Gln Lys Ala Gln Gln Lys Thr Leu Leu Trp Leu Gly Asn
            580                 585                 590

Asn Thr Leu Gly Gln Met Arg Ala Thr Thr Lys Met
            595                 600

<210> SEQ ID NO 9
<211> LENGTH: 1749
<212> TYPE: PRT
<213> ORGANISM: Artificial Sequence
<220> FEATURE:
<223> OTHER INFORMATION: Synthetic

<400> SEQUENCE: 9

Ala Thr Gly Gly Ala Gly Cys Thr Gly Cys Thr Gly Ala Thr Cys Cys
1               5                   10                  15

Thr Gly Ala Ala Gly Gly Cys Cys Ala Ala Cys Gly Cys Cys Ala Thr
                20                  25                  30

Cys Ala Cys Cys Ala Cys Ala Thr Cys Cys Thr Gly Ala Cys Cys Cys
            35                  40                  45

Gly Cys Cys Gly Thr Gly Ala Cys Cys Thr Thr Cys Thr Gly Cys Thr
        50                  55                  60

Thr Cys Gly Cys Ala Gly Cys Gly Gly Cys Cys Ala Gly Ala Ala Ala
65                  70                  75                  80

Cys Ala Thr Thr Ala Cys Cys Gly Ala Gly Ala Gly Thr Thr Cys Thr
                85                  90                  95

Thr Ala Cys Cys Ala Gly Ala Gly Cys Cys Thr Gly Cys Thr Gly Ala
                100                 105                 110

Gly Cys Gly Cys Gly Thr Gly Ala Gly Cys Ala Ala Gly Gly Gly Gly
            115                 120                 125

Cys Thr Ala Cys Cys Thr Gly Ala Gly Cys Gly Cys Cys Cys Thr Gly
        130                 135                 140

Ala Gly Ala Ala Cys Cys Gly Gly Cys Thr Gly Gly Thr Ala Cys Ala
145                 150                 155                 160

Cys Cys Ala Gly Cys Gly Thr Gly Ala Thr Cys Ala Cys Cys Ala Thr
                165                 170                 175

Cys Gly Ala Gly Cys Thr Gly Ala Gly Cys Ala Ala Cys Ala Thr Cys
            180                 185                 190

Ala Ala Gly Gly Ala Gly Ala Thr Thr Ala Ala Gly Thr Gly Cys Ala
            195                 200                 205

Ala Cys Gly Gly Cys Ala Cys Cys Gly Ala Cys Gly Cys Cys Ala Ala
        210                 215                 220

Gly Gly Thr Gly Ala Ala Gly Cys Thr Gly Ala Thr Cys Ala Ala Gly
225                 230                 235                 240

Cys Ala Gly Gly Ala Gly Cys Thr Gly Ala Cys Ala Ala Gly Thr
                245                 250                 255

Ala Cys Ala Ala Gly Ala Ala Cys Gly Cys Cys Gly Thr Gly Ala Cys
                260                 265                 270

Cys Gly Ala Gly Cys Thr Gly Cys Ala Gly Cys Thr Gly Cys Thr Gly
            275                 280                 285

Ala Thr Gly Cys Ala Gly Ala Gly Cys Ala Cys Cys Cys Cys Cys Gly
            290                 295                 300
```

-continued

```
Cys Cys Ala Cys Cys Ala Ala Cys Ala Ala Cys Cys Ala Gly Gly Cys
305                 310                 315                 320

Cys Ala Gly Gly Gly Gly Gly Thr Cys Ala Gly Gly Gly Thr Cys Ala
                325                 330                 335

Gly Gly Ala Ala Gly Gly Thr Cys Cys Cys Thr Gly Gly Gly Cys Thr
            340                 345                 350

Thr Cys Cys Thr Gly Cys Thr Gly Gly Gly Ala Gly Thr Gly Gly Gly
        355                 360                 365

Cys Thr Cys Cys Gly Cys Cys Ala Thr Cys Gly Cys Thr Thr Cys Cys
    370                 375                 380
Gly Gly Ala Gly Thr Gly Gly Cys Cys Gly Thr Gly Ala Gly Cys Ala
385                 390                 395                 400
Ala Gly Gly Thr Cys Cys Thr Gly Cys Ala Cys Cys Thr Gly Gly Ala
                405                 410                 415

Gly Gly Gly Cys Gly Ala Gly Gly Thr Cys Ala Ala Thr Ala Ala Gly
            420                 425                 430

Ala Thr Cys Ala Ala Gly Thr Cys Cys Gly Cys Cys Cys Thr Cys Cys
        435                 440                 445
Thr Gly Ala Gly Cys Ala Cys Cys Ala Ala Thr Ala Ala Gly Gly Cys
    450                 455                 460
Cys Gly Thr Cys Gly Thr Gly Ala Gly Cys Cys Thr Cys Ala Gly Cys
465                 470                 475                 480
Ala Ala Thr Gly Gly Cys Gly Thr Gly Ala Gly Cys Gly Thr Gly Cys
                485                 490                 495

Thr Gly Ala Cys Ala Thr Cys Cys Ala Ala Gly Gly Thr Cys Cys Thr
            500                 505                 510

Cys Gly Ala Cys Cys Thr Gly Ala Ala Gly Ala Ala Cys Thr Ala Cys
        515                 520                 525

Ala Thr Cys Gly Ala Cys Ala Ala Gly Cys Ala Gly Cys Thr Gly Cys
    530                 535                 540

Thr Cys Cys Cys Thr Ala Thr Cys Gly Thr Gly Ala Ala Cys Ala Ala
545                 550                 555                 560

Ala Cys Ala Gly Ala Gly Cys Thr Gly Cys Ala Gly Gly Ala Thr Cys
                565                 570                 575

Cys Cys Cys Ala Ala Cys Ala Thr Cys Gly Ala Gly Ala Cys Cys Gly
            580                 585                 590

Thr Gly Ala Thr Cys Gly Ala Gly Thr Thr Cys Cys Ala Gly Cys Ala
        595                 600                 605

Gly Ala Ala Gly Ala Ala Cys Ala Ala Cys Ala Gly Gly Cys Thr Gly
    610                 615                 620

Cys Thr Gly Gly Ala Gly Ala Thr Cys Ala Cys Cys Ala Gly Gly Gly
625                 630                 635                 640

Ala Ala Thr Thr Thr Ala Gly Cys Gly Thr Gly Ala Ala Cys Gly Cys
                645                 650                 655

Cys Gly Gly Ala Gly Thr Gly Ala Cys Cys Ala Cys Cys Cys Cys Cys
            660                 665                 670

Gly Thr Gly Ala Gly Cys Ala Cys Cys Thr Ala Thr Ala Thr Gly Cys
        675                 680                 685

Thr Gly Ala Cys Ala Ala Ala Cys Ala Gly Cys Gly Ala Gly Cys Thr
    690                 695                 700

Gly Cys Thr Gly Thr Cys Cys Cys Thr Gly Ala Thr Cys Ala Ala Cys
705                 710                 715                 720
```

```
Gly Ala Cys Ala Thr Gly Cys Cys Cys Ala Cys Cys Ala
                725                 730             735

Ala Cys Gly Ala Cys Cys Ala Gly Ala Ala Gly Cys Thr
        740             745             750

Gly Ala Thr Gly Ala Gly Cys Ala Ala Thr Ala Ala Cys Gly Thr Gly
            755             760             765

Cys Ala Gly Ala Thr Cys Gly Thr Gly Ala Gly Cys Ala Gly Cys
        770             775             780

Ala Gly Ala Gly Cys Thr Ala Cys Ala Gly Ala Thr Cys Ala Thr
785             790             795             800

Gly Thr Cys Cys Ala Thr Cys Ala Thr Cys Ala Ala Gly Gly Ala Gly
            805             810             815

Gly Ala Gly Gly Thr Cys Cys Thr Gly Gly Cys Thr Thr Ala Cys Gly
            820             825             830

Thr Gly Gly Thr Cys Cys Ala Ala Cys Thr Gly Cys Cys Thr Cys Thr
            835             840             845

Gly Thr Ala Cys Gly Gly Cys Gly Thr Gly Ala Thr Cys Gly Ala Cys
        850             855             860

Ala Cys Cys Cys Cys Thr Thr Gly Cys Thr Gly Gly Ala Ala Gly Cys
865             870             875             880

Thr Gly Cys Ala Cys Ala Cys Ala Ala Gly Cys Cys Cys Cys Thr
            885             890             895

Gly Thr Gly Thr Ala Cys Cys Ala Cys Cys Ala Ala Thr Ala Cys Cys
            900             905             910

Ala Ala Gly Gly Ala Gly Gly Cys Ala Gly Cys Ala Ala Cys Ala
            915             920             925

Thr Cys Thr Gly Cys Cys Thr Gly Ala Cys Ala Ala Gly Gly Ala Cys
    930             935             940

Cys Gly Ala Cys Ala Gly Ala Gly Gly Cys Thr Gly Gly Thr Ala Cys
945             950             955             960

Thr Gly Cys Gly Ala Cys Ala Ala Thr Gly Cys Cys Gly Gly Cys Thr
            965             970             975

Cys Cys Gly Thr Gly Thr Cys Cys Thr Thr Cys Thr Thr Thr Cys Cys
            980             985             990

Cys Cys Ala Gly Gly Cys Thr Gly  Ala Gly Ala Cys Cys  Thr Gly Cys
            995                 1000            1005

Ala Ala  Gly Gly Thr Cys Cys  Ala Gly Ala Gly Cys  Ala Ala Cys
        1010            1015                1020

Ala Gly  Gly Gly Thr Gly Thr  Thr Cys Thr Gly Cys  Gly Ala Cys
        1025            1030                1035

Ala Cys  Cys Ala Thr Gly Ala  Ala Cys Thr Cys Cys  Cys Thr Gly
        1040            1045                1050

Ala Cys  Cys Cys Thr Cys Cys  Cys Cys Ala Gly Cys  Gly Ala Gly
        1055            1060                1065

Gly Thr  Gly Ala Ala Cys Cys  Thr Gly Thr Gly Cys  Ala Ala Cys
        1070            1075                1080

Gly Thr  Cys Gly Ala Cys Ala  Thr Cys Thr Thr Cys  Ala Ala Cys
        1085            1090                1095

Cys Cys  Cys Ala Ala Gly Thr  Ala Cys Gly Ala Thr  Thr Gly Thr
        1100            1105                1110

Ala Ala  Gly Ala Thr Cys Ala  Thr Gly Ala Cys Cys  Ala Gly Cys
        1115            1120                1125

Ala Ala  Ala Ala Cys Cys Gly  Ala Cys Gly Thr Gly  Ala Gly Cys
```

```
    1130                1135                1140

Ala Gly  Cys Ala Gly Cys Gly  Thr Gly Ala Thr Cys  Ala Cys Cys
    1145                1150                1155

Thr Cys  Cys Cys Thr Gly Gly  Gly Cys Gly Cys Cys  Ala Thr Cys
    1160                1165                1170

Gly Thr  Gly Ala Gly Cys Thr  Gly Cys Thr Ala Cys  Gly Gly Cys
    1175                1180                1185

Ala Ala  Gly Ala Cys Cys Ala  Ala Gly Thr Gly Thr  Ala Cys Cys
    1190                1195                1200

Gly Cys  Cys Thr Cys Cys Ala  Ala Cys Ala Ala Gly  Ala Ala Thr
    1205                1210                1215

Ala Gly  Gly Gly Gly Ala Ala  Thr Cys Ala Thr Thr  Ala Ala Gly
    1220                1225                1230

Ala Cys  Cys Thr Thr Cys Thr  Cys Cys Ala Ala Cys  Gly Gly Cys
    1235                1240                1245

Thr Gly  Cys Gly Ala Cys Thr  Ala Cys Gly Thr Cys  Thr Cys Cys
    1250                1255                1260

Ala Ala  Cys Ala Ala Gly Gly  Gly Cys Gly Thr Gly  Gly Ala Cys
    1265                1270                1275

Ala Cys  Ala Gly Thr Gly Thr  Cys Cys Gly Thr Gly  Gly Gly Cys
    1280                1285                1290

Ala Ala  Cys Ala Cys Cys Cys  Thr Gly Thr Ala Cys  Thr Ala Cys
    1295                1300                1305

Gly Thr  Gly Ala Ala Thr Ala  Ala Gly Cys Ala Gly  Gly Ala Gly
    1310                1315                1320

Gly Gly  Cys Ala Ala Gly Ala  Gly Cys Cys Thr Gly  Thr Ala Cys
    1325                1330                1335

Gly Thr  Gly Ala Ala Gly Gly  Gly Ala Gly Ala Gly  Cys Cys Thr
    1340                1345                1350

Ala Thr  Cys Ala Thr Cys Ala  Ala Cys Thr Thr Thr  Thr Ala Cys
    1355                1360                1365

Gly Ala  Cys Cys Cys Cys Cys  Thr Gly Gly Thr Gly  Thr Thr Cys
    1370                1375                1380

Cys Cys  Thr Ala Gly Cys Gly  Ala Cys Gly Ala Gly  Thr Thr Cys
    1385                1390                1395

Gly Ala  Cys Gly Cys Cys Ala  Gly Cys Ala Thr Cys  Ala Gly Cys
    1400                1405                1410

Cys Ala  Gly Gly Thr Gly Ala  Ala Cys Gly Ala Gly  Ala Ala Gly
    1415                1420                1425

Ala Thr  Cys Ala Ala Cys Cys  Ala Gly Ala Gly Cys  Cys Thr Gly
    1430                1435                1440

Gly Cys  Cys Thr Thr Cys Ala  Thr Cys Ala Gly Ala  Ala Ala Gly
    1445                1450                1455

Thr Cys  Cys Gly Ala Cys Gly  Ala Gly Cys Thr Cys  Cys Thr Cys
    1460                1465                1470

Cys Ala  Thr Ala Ala Cys Gly  Thr Cys Ala Ala Cys  Gly Cys Cys
    1475                1480                1485

Gly Gly  Gly Ala Ala Ala Gly  Gly Ala Thr Ala Thr  Ala Thr Cys
    1490                1495                1500

Cys Cys  Cys Gly Ala Ala Gly  Cys Thr Cys Cys Thr  Cys Gly Gly
    1505                1510                1515

Gly Ala  Thr Gly Gly Thr Cys  Ala Gly Gly Cys Cys  Thr Ala Cys
    1520                1525                1530
```

Gly Thr Thr Cys Gly Cys Ala Ala Gly Gly Ala Thr Gly Gly Ala
            1535                1540                1545

Gly Ala Gly Thr Gly Gly Gly Thr Ala Cys Thr Gly Cys Thr Gly
    1550                1555                1560

Thr Cys Thr Ala Cys Thr Thr Thr Cys Cys Thr Gly Ala Gly Thr
    1565                1570                1575

Ala Cys Thr Ala Cys Thr Ala Ala Thr Cys Thr Cys Ala Thr Thr
    1580                1585                1590

Ala Cys Cys Thr Ala Thr Ala Thr Cys Gly Cys Thr Thr Thr Ala
    1595                1600                1605

Ala Cys Thr Gly Cys Cys Ala Thr Ala Thr Cys Thr Cys Thr Thr
    1610                1615                1620

Gly Thr Thr Thr Gly Cys Gly Gly Thr Ala Thr Ala Cys Thr Thr
    1625                1630                1635

Ala Gly Thr Cys Thr Gly Gly Thr Thr Cys Thr Ala Gly Cys Ala
    1640                1645                1650

Thr Gly Cys Thr Ala Cys Cys Thr Ala Ala Thr Gly Thr Ala Cys
    1655                1660                1665

Ala Ala Gly Cys Ala Ala Ala Ala Gly Gly Cys Gly Cys Ala Ala
    1670                1675                1680

Cys Ala Ala Ala Gly Ala Cys Cys Thr Thr Gly Thr Thr Ala
    1685                1690                1695

Thr Gly Gly Cys Thr Thr Gly Gly Gly Ala Ala Thr Ala Ala Thr
    1700                1705                1710

Ala Cys Cys Cys Thr Gly Gly Gly Thr Cys Ala Gly Ala Thr Gly
    1715                1720                1725

Ala Gly Ala Gly Cys Cys Ala Cys Thr Ala Cys Ala Ala Ala
    1730                1735                1740

Ala Thr Gly Thr Gly Ala
    1745

<210> SEQ ID NO 10
<211> LENGTH: 582
<212> TYPE: PRT
<213> ORGANISM: Artificial Sequence
<220> FEATURE:
<223> OTHER INFORMATION: Synthetic

<400> SEQUENCE: 10

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Ile Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

-continued

```
Gly Val Ala Val Ser Lys Val Leu His Leu Glu Gly Glu Val Asn Lys
        130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Arg Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
        435                 440                 445

Gly Glu Pro Ile Ile Asn Phe Tyr Asp Pro Leu Val Phe Pro Ser Asp
450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu His Asn Val Asn Ala
                485                 490                 495

Gly Lys Gly Tyr Ile Pro Glu Ala Pro Arg Asp Gly Gln Ala Tyr Val
            500                 505                 510

Arg Lys Asp Gly Glu Trp Val Leu Leu Ser Thr Phe Leu Ser Thr Thr
        515                 520                 525

Asn Leu Ile Thr Tyr Ile Ala Leu Thr Ala Ile Ser Leu Val Cys Gly
530                 535                 540
```

Ile Leu Ser Leu Val Leu Ala Cys Tyr Leu Met Tyr Lys Gln Lys Ala
545                 550                 555                 560

Gln Gln Lys Thr Leu Leu Trp Leu Gly Asn Asn Thr Leu Gly Gln Met
            565                 570                 575

Arg Ala Thr Thr Lys Met
            580

<210> SEQ ID NO 11
<211> LENGTH: 1749
<212> TYPE: DNA
<213> ORGANISM: Artificial Sequence
<220> FEATURE:
<223> OTHER INFORMATION: Synthetic

<400> SEQUENCE: 11

| | | | | | | |
|---|---|---|---|---|---|---|
| atggagctgc | tgatcctgaa | ggccaacgcc | atcaccacca | tcctgaccgc | cgtgaccttc | 60 |
| tgcttcgcca | gcggccagaa | cattaccgag | gagttctacc | agagcacctg | cagcgccgtg | 120 |
| agcaagggct | acctgagcgc | cctgagaacc | ggctggtaca | ccagcgtgat | caccatcgag | 180 |
| ctgagcaaca | tcaaggagat | taagtgcaac | ggcaccgacg | ccaaggtgaa | gctgatcaag | 240 |
| caggagctgg | acaagtacaa | gaacgccgtg | accgagctgc | agctgctgat | gcagagcacc | 300 |
| cccgccacca | caaccaggc | cagggggtca | gggtcaggaa | ggtccctggg | cttcctgctg | 360 |
| ggagtgggct | ccgccatcgc | ttccggagtg | gccgtgagca | aggtcctgca | cctggagggc | 420 |
| gaggtcaata | agatcaagtc | cgccctcctg | agcaccaata | aggccgtcgt | gagcctcagc | 480 |
| aatggcgtga | gcgtgctgac | atccaaggtc | ctcgacctga | gaactacat | cgacaagcag | 540 |
| ctgctcccta | tcgtgaacaa | acagagctgc | aggatcccca | catcgagac | cgtgatcgag | 600 |
| ttccagcaga | gaacaacag | gctgctggag | atcaccaggg | aatttagcgt | gaacgccgga | 660 |
| gtgaccaccc | ccgtgagcac | ctatatgctg | acaaacagcg | agctgctgtc | cctgatcaac | 720 |
| gacatgccca | tcaccaacga | ccagaagaag | ctgatgagca | taacgtgca | gatcgtgagg | 780 |
| cagcagagct | acagcatcat | gtccatcatc | aaggaggagg | tcctggctta | cgtggtccaa | 840 |
| ctgcctctgt | acggcgtgat | cgacacccct | tgctggaagc | tgcacacaag | ccccctgtgt | 900 |
| accaccaata | ccaaggaggg | cagcaacatc | tgcctgacaa | ggaccgacag | aggctggtac | 960 |
| tgcgacaatg | ccggctccgt | gtccttctt | ccccaggctg | agacctgcaa | ggtccagagc | 1020 |
| aacagggtgt | tctgcgacac | catgaactcc | ctgacccctcc | ccagcgaggt | gaacctgtgc | 1080 |
| aacgtcgaca | tcttcaaccc | caagtacgat | tgtaagatca | tgaccagcaa | aaccgacgtg | 1140 |
| agcagcagcg | tgatcaccctc | cctgggcgcc | atcgtgagct | gctacggcaa | gaccaagtgt | 1200 |
| accgcctcca | caagaatag | gggaatcatt | aagaccttct | ccaacggctg | cgactacgtc | 1260 |
| tccaacaagg | gcgtggacac | agtgtccgtg | ggcaacaccc | tgtactacgt | gaataagcag | 1320 |
| gagggcaaga | gcctgtacgt | gaagggagag | cctatcatca | acttttacga | ccccctggtg | 1380 |
| ttccctagca | acgagttcga | cgccagcatc | agccaggtga | acgagaagat | caaccagagc | 1440 |
| ctggccttca | tcagaaagtc | cgacgagctc | ctccataacg | tcaacgccgg | gaaaggatat | 1500 |
| atccccgaag | ctcctcggga | tggtcaggcc | tacgttcgca | aggatggaga | gtgggtactg | 1560 |
| ctgtctactt | tcctgagtac | tactaatctc | attacctata | tcgctttaac | tgccatatct | 1620 |
| cttgttttgcg | gtatacttag | tctggttcta | gcatgctacc | taatgtacaa | gcaaaaggcg | 1680 |
| caacaaaaga | ccttgttatg | gcttgggaat | aatacccctgg | gtcagatgag | agccactaca | 1740 |
| aaaatgtga | | | | | | 1749 |

<210> SEQ ID NO 12
<211> LENGTH: 582
<212> TYPE: PRT
<213> ORGANISM: Artificial Sequence
<220> FEATURE:
<223> OTHER INFORMATION: Synthetic

<400> SEQUENCE: 12

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Ile Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
    130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Arg Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365
```

```
Tyr Asp Cys Lys Ile Met Thr Ser Lys Thr Asp Val Ser Ser Ser Val
    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
        435                 440                 445

Gly Glu Pro Ile Ile Asn Phe Tyr Asp Pro Leu Val Phe Pro Ser Asn
    450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu His Asn Val Asn Ala
                485                 490                 495

Gly Lys Gly Tyr Ile Pro Glu Ala Pro Arg Asp Gly Gln Ala Tyr Val
            500                 505                 510

Arg Lys Asp Gly Glu Trp Val Leu Leu Ser Thr Phe Leu Ser Thr Thr
        515                 520                 525

Asn Leu Ile Thr Tyr Ile Ala Leu Thr Ala Ile Ser Leu Val Cys Gly
    530                 535                 540

Ile Leu Ser Leu Val Leu Ala Cys Tyr Leu Met Tyr Lys Gln Lys Ala
545                 550                 555                 560

Gln Gln Lys Thr Leu Leu Trp Leu Gly Asn Asn Thr Leu Gly Gln Met
                565                 570                 575

Arg Ala Thr Thr Lys Met
            580

<210> SEQ ID NO 13
<211> LENGTH: 7
<212> TYPE: PRT
<213> ORGANISM: Artificial Sequence
<220> FEATURE:
<223> OTHER INFORMATION: Synthetic

<400> SEQUENCE: 13

Gly Ser Gly Ser Gly Arg Ser
1               5

<210> SEQ ID NO 14
<211> LENGTH: 633
<212> TYPE: DNA
<213> ORGANISM: Artificial Sequence
<220> FEATURE:
<223> OTHER INFORMATION: Synthetic

<400> SEQUENCE: 14
tagtaatcaa ttacggggtc attagttcat agcccatata tggagttccg cgttacataa      60
cttacggtaa atggcccgcc tggctgaccg cccaacgacc cccgcccatt gacgtcaata     120
atgacgtatg ttcccatagt aacgccaata gggactttcc attgacgtca atgggtggag    180
tatttacggt aaactgccca cttggcagta catcaagtgt atcatatgcc aagtacgccc    240
cctattgacg tcaatgacgg taaatggccc gcctggcatt atgcccagta catgacctta    300
tgggactttc ctacttggca gtacatctac gtattagtca tcgctattac catggtcgag    360
gtgagcccca cgttctgctt cactctcccc atctccccccc ctccccacc cccaatttttg   420
```

| | |
|---|---|
| tatttattta tttttttaatt attttgtgca gcgatggggg cgggggggggg ggggggggcgc | 480 |
| gcgccaggcg gggcggggcg gggcgagggg cggggcgggg cgaggcggag aggtgcggcg | 540 |
| gcagccaatc agagcggcgc gctccgaaag tttccttttta tggcgaggcg gcggcggcgg | 600 |
| cggccctata aaaagcgaag cgcgcggcgg gcg | 633 |

```
<210> SEQ ID NO 15
<211> LENGTH: 1826
<212> TYPE: DNA
<213> ORGANISM: Artificial Sequence
<220> FEATURE:
<223> OTHER INFORMATION: Synthetic

<400> SEQUENCE: 15
```

| | |
|---|---|
| gtcgacattg attattgact agttattaat agtaatcaat tacggggtca ttagttcata | 60 |
| gcccatatat ggagttccgc gttacataac ttacggtaaa tggcccgcct ggctgaccgc | 120 |
| ccaacgaccc ccgcccattg acgtcaataa tgacgtatgt tcccatagta acgccaatag | 180 |
| ggactttcca ttgacgtcaa tgggtggagt atttacggta aactgcccac ttggcagtac | 240 |
| atcaagtgta tcatatgcca agtacgcccc ctattgacgt caatgacggt aaatggcccg | 300 |
| cctggcatta tgcccagtac atgaccttat gggactttcc tacttggcag tacatctacg | 360 |
| tattagtcat cgctattacc atggtcgagg tgagccccac gttctgcttc actctcccca | 420 |
| tctcccccc ctcccaccc ccaattttgt atttatttat tttttaatta ttttgtgcag | 480 |
| cgatggggc gggggggggg ggggggcccc cccaggcgg ggcggggcgg ggcgagggc | 540 |
| ggggcgggc gaggcggaaa ggtgcggcgg cagccaatca gagcggcgcg ctccgaaagt | 600 |
| ttccttttat ggcgaggcgg cggcggcggc ggccctataa aaagcgaagc gcgcggcggg | 660 |
| cgggagtcgt tgcgcgctgc cttccccccg tgccccgctc cgccgccgcc tcgcgccgcc | 720 |
| cgccccggct ctgactgacc gcgttactcc cacaggtgag cgggcgggac ggcccttctc | 780 |
| ctccgggctg taattagcgc ttggtttaat gacggcttgt ttcttttctg tggctgcgtg | 840 |
| aaagccttga ggggctccgg gagggccctt tgtgcggggg gagcggctcg ggggtgcgt | 900 |
| gcgtgtgtgt gtgcgtgggg agcgccgcgt gcggctccgc gctgcccggc ggctgtgagc | 960 |
| gctgcgggcg cggcgcgggg ctttgtgcgc tccgcagtgt gcgcgagggg agcgcggccg | 1020 |
| ggggcggtgc cccgcggtgc gggggggggct gcgaggggaa caaaggctgc gtgcggggtg | 1080 |
| tgtgcgtggg ggggtgagca gggggtgtgg gcgcgtcggt cgggctgcaa cccccctgc | 1140 |
| acccccctcc ccgagttgct gagcacggcc cggcttcggg tgcggggctc cgtacggggc | 1200 |
| gtggcgcggg gctcgccgtg ccgggcgggg ggtggcggca ggtgggggtg ccgggcgggg | 1260 |
| cggggccgcc tcgggccggg gagggctcgg gggaaggggc gcggcggccc ccggagcgcc | 1320 |
| ggcggctgtc gaggcgcggc gagccgcagc cattgccttt tatggtaatc gtgcgagagg | 1380 |
| gcgcagggac ttccttttgtc ccaaatctgt gcggagccga atctgggag gcgccgccgc | 1440 |
| acccctcta gcgggcgcgg ggcgaagcgg tgcggcgccg gcaggaagga atgggcgggg | 1500 |
| gagggccttc gtgcgtcgcc gcgccgccgt ccccttctcc ctctccagcc tcggggctgt | 1560 |
| ccgcgggggg acggctgcct tcgggggggga cgggcaggg cggggttcgg cttctggcgt | 1620 |
| gtgaccggcg gctctagagc ctctgctaac catgttcatg ccttcttctt tttcctacag | 1680 |
| ctcctgggca acgtgctggt tattgtgctg tctcatcatt ttggcaaaga attcctcgag | 1740 |
| gaattcactc ctcaggtgca ggctgcctat cagaaggtgg tggctggtgt ggccaatgcc | 1800 |
| ctggctcaca ataccactg agatct | 1826 |

<210> SEQ ID NO 16
<211> LENGTH: 489
<212> TYPE: PRT
<213> ORGANISM: Artificial Sequence
<220> FEATURE:
<223> OTHER INFORMATION: Synthetic

<400> SEQUENCE: 16

```
Met Ser Ser Val Phe Asp Glu Tyr Glu Gln Leu Leu Ala Ala Gln Thr
1               5                   10                  15

Arg Pro Asn Gly Ala His Gly Gly Glu Lys Gly Ser Thr Leu Lys
            20                  25                  30

Val Glu Val Pro Val Phe Thr Leu Asn Ser Asp Asp Pro Glu Asp Arg
        35                  40                  45

Trp Asn Phe Val Val Phe Cys Leu Arg Ile Ala Val Ser Glu Asp Ala
    50                  55                  60

Asn Lys Pro Leu Arg Gln Gly Ala Leu Ile Ser Leu Leu Cys Ser His
65                  70                  75                  80

Ser Gln Val Met Arg Asn His Val Ala Leu Ala Gly Lys Gln Asn Glu
                85                  90                  95

Ala Thr Leu Ala Val Leu Glu Ile Asp Gly Phe Thr Asn Ser Val Pro
            100                 105                 110

Gln Phe Asn Asn Thr Ser Gly Val Ser Glu Glu Arg Ala Gln Arg Phe
        115                 120                 125

Met Met Ile Ala Gly Ser Leu Pro Arg Ala Cys Ser Asn Gly Thr Pro
    130                 135                 140

Phe Ile Thr Ala Gly Val Glu Asp Asp Ala Pro Glu Asp Ile Ile Asp
145                 150                 155                 160

Thr Leu Glu Arg Ile Leu Ser Ile Gln Ala Gln Val Trp Val Thr Val
                165                 170                 175

Ala Lys Ala Met Thr Ala Tyr Glu Thr Ala Asp Glu Ser Glu Thr Arg
            180                 185                 190

Arg Ile Asn Lys Tyr Met Gln Gln Gly Arg Val Gln Lys Lys Tyr Ile
        195                 200                 205

Leu His Pro Val Cys Arg Ser Ala Ile Gln Leu Thr Ile Arg Gln Ser
    210                 215                 220

Leu Ala Val Arg Ile Phe Leu Val Ser Glu Leu Lys Arg Gly Arg Asn
225                 230                 235                 240

His Ala Gly Gly Ser Ser Thr Tyr Tyr Asn Leu Val Gly Asp Val Asp
                245                 250                 255

Ser Tyr Ile Arg Asn Thr Gly Leu Thr Ala Phe Phe Leu Thr Leu Lys
            260                 265                 270

Tyr Gly Ile Asn Thr Lys Thr Ser Ala Leu Ala Leu Ser Ser Leu Ala
        275                 280                 285

Gly Asp Ile Gln Lys Met Lys Gln Leu Met Arg Leu Tyr Arg Met Lys
    290                 295                 300

Gly Asp Asn Ala Pro Tyr Met Thr Leu Leu Gly Asp Ser Asp Gln Met
305                 310                 315                 320

Ser Phe Ala Pro Ala Glu Tyr Ala Gln Leu Tyr Ser Phe Ala Met Ala
                325                 330                 335

Met Ala Ser Val Leu Asp Lys Gly Thr Gly Lys Tyr Gln Phe Ala Arg
            340                 345                 350

Asp Phe Met Ser Thr Ser Phe Trp Arg Leu Gly Val Glu Tyr Ala Gln
        355                 360                 365
```

```
Ala Gln Gly Ser Ser Ile Asn Glu Asp Met Ala Ala Glu Leu Lys Leu
            370                 375                 380

Thr Pro Ala Ala Arg Arg Gly Leu Ala Ala Ala Gln Arg Val Ser
385                 390                 395                 400

Glu Glu Thr Ser Ser Met Asp Ile Pro Thr Gln Gln Ala Gly Val Leu
                405                 410                 415

Thr Gly Leu Ser Asp Gly Gly Pro Gln Ala Pro Gln Gly Gly Ser Asn
                420                 425                 430

Arg Ser Gln Gly Arg Pro Asp Ala Gly Asp Gly Glu Thr Gln Phe Leu
                435                 440                 445

Asp Leu Met Arg Ala Val Ala Asn Ser Met Arg Glu Ala Pro Asn Ser
                450                 455                 460

Val Gln Ser Thr Thr Gln Pro Glu Pro Pro Thr Pro Gly Pro Ser
465                 470                 475                 480

Gln Asp Asn Asp Thr Asp Trp Gly Tyr
                485

<210> SEQ ID NO 17
<211> LENGTH: 364
<212> TYPE: PRT
<213> ORGANISM: Artificial Sequence
<220> FEATURE:
<223> OTHER INFORMATION: Synthetic

<400> SEQUENCE: 17

Met Asp Ser Ser Arg Thr Ile Gly Leu Tyr Phe Asp Ser Ala Leu Pro
1               5                   10                  15

Ser Ser Asn Leu Leu Ala Phe Pro Ile Val Leu Gln Asp Ile Gly Asp
                20                  25                  30

Gly Lys Lys Gln Ile Ala Pro Gln Tyr Arg Ile Gln Arg Leu Asp Ser
            35                  40                  45

Trp Thr Asp Ser Lys Glu Asp Ser Val Phe Ile Thr Thr Tyr Gly Phe
        50                  55                  60

Ile Phe Gln Val Gly Asn Glu Glu Val Thr Val Gly Met Ile Ser Asp
65                  70                  75                  80

Asn Pro Lys His Glu Leu Leu Ser Ala Ala Met Leu Cys Leu Gly Ser
                85                  90                  95

Val Pro Asn Val Gly Asp Leu Val Glu Leu Ala Arg Ala Cys Leu Thr
                100                 105                 110

Met Val Val Thr Cys Lys Lys Ser Ala Thr Asp Thr Glu Arg Met Val
            115                 120                 125

Phe Ser Val Val Gln Ala Pro Gln Val Leu Gln Ser Cys Arg Val Val
        130                 135                 140

Ala Asn Lys Tyr Ser Ser Val Asn Ala Val Lys His Val Lys Ala Pro
145                 150                 155                 160

Glu Lys Ile Pro Gly Ser Gly Thr Leu Glu Tyr Lys Val Asn Phe Val
                165                 170                 175

Ser Leu Thr Val Val Pro Arg Lys Asp Val Tyr Lys Ile Pro Thr Ala
                180                 185                 190

Ala Leu Lys Val Ser Gly Ser Ser Leu Tyr Asn Leu Ala Leu Asn Val
            195                 200                 205

Thr Ile Asp Val Glu Val Asp Pro Lys Ser Pro Leu Val Lys Ser Leu
        210                 215                 220

Ser Lys Ser Asp Ser Gly Tyr Tyr Ala Asn Leu Phe Leu His Ile Gly
225                 230                 235                 240
```

```
Leu Met Ser Thr Val Asp Lys Gly Lys Val Thr Phe Asp Lys
            245                 250                 255

Leu Glu Arg Lys Ile Arg Arg Leu Asp Leu Ser Val Gly Leu Ser Asp
            260                 265                 270

Val Leu Gly Pro Ser Val Leu Val Lys Ala Arg Gly Ala Arg Thr Arg
            275                 280                 285

Leu Leu Ala Pro Phe Phe Ser Ser Ser Gly Thr Ala Cys Tyr Pro Ile
            290                 295                 300

Ser Asn Ala Ser Pro Gln Val Ala Lys Ile Leu Trp Ser Gln Thr Ala
305                 310                 315                 320

Arg Leu Arg Ser Val Lys Val Ile Ile Gln Ala Gly Thr Gln Arg Ala
                325                 330                 335

Val Ala Val Thr Ala Asp His Glu Val Thr Ser Thr Lys Ile Glu Lys
                340                 345                 350

Arg His Thr Ile Ala Lys Tyr Asn Pro Phe Lys Lys
                355                 360

<210> SEQ ID NO 18
<211> LENGTH: 281
<212> TYPE: PRT
<213> ORGANISM: Artificial Sequence
<220> FEATURE:
<223> OTHER INFORMATION: Synthetic

<400> SEQUENCE: 18

Met Asn Arg Ala Val Cys Gln Val Ala Leu Glu Asn Asp Glu Arg Glu
1               5                   10                  15

Ala Lys Asn Thr Trp Arg Leu Val Phe Arg Ile Ala Ile Leu Leu Leu
                20                  25                  30

Thr Val Met Thr Leu Ala Ile Ser Ala Ala Leu Ala Tyr Ser Ala
            35                  40                  45

Asn His Lys Val Thr Pro Thr Thr Ala Ile Ile Gln Asp Ala Thr Ser
        50                  55                  60

Gln Ile Lys Asn Thr Thr Pro Thr Tyr Leu Thr Gln Asn Pro Gln Leu
65                  70                  75                  80

Gly Ile Ser Pro Ser Asn Pro Ser Glu Ile Thr Ser Gln Ile Thr Thr
                85                  90                  95

Ile Leu Ala Ser Thr Thr Pro Gly Val Lys Ser Thr Leu Gln Ser Thr
            100                 105                 110

Thr Val Lys Thr Lys Asn Thr Thr Thr Gln Thr Gln Pro Ser Lys
            115                 120                 125

Pro Thr Thr Lys Gln Arg Gln Asn Lys Pro Pro Ser Lys Pro Asn Asn
130                 135                 140

Asp Phe His Phe Glu Val Phe Asn Phe Val Pro Cys Ser Ile Cys Ser
145                 150                 155                 160

Asn Asn Pro Thr Cys Trp Ala Ile Cys Lys Arg Ile Pro Asn Lys Lys
                165                 170                 175

Pro Gly Lys Lys Thr Thr Thr Lys Pro Thr Lys Lys Pro Thr Leu Lys
            180                 185                 190

Thr Thr Lys Lys Asp Pro Lys Pro Gln Thr Thr Lys Ser Lys Glu Val
            195                 200                 205

Pro Thr Thr Lys Pro Thr Glu Glu Pro Thr Ile Asn Thr Thr Lys Thr
            210                 215                 220

Asn Ile Ile Thr Thr Leu Leu Thr Ser Asn Thr Thr Gly Asn Pro Glu
225                 230                 235                 240
```

```
Leu Thr Ser Gln Met Glu Thr Phe His Ser Thr Ser Glu Gly Asn
            245                 250                 255

Pro Ser Pro Ser Gln Val Ser Thr Thr Ser Glu Tyr Pro Ser Gln Pro
            260                 265                 270

Ser Ser Pro Pro Asn Thr Pro Arg Gln
        275                 280

<210> SEQ ID NO 19
<211> LENGTH: 582
<212> TYPE: PRT
<213> ORGANISM: Artificial Sequence
<220> FEATURE:
<223> OTHER INFORMATION: Synthetic

<400> SEQUENCE: 19

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Ile Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
    130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Arg Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320
```

```
Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
            355                 360                 365

Tyr Asp Cys Lys Ile Met Thr Ser Lys Thr Asp Val Ser Ser Ser Val
        370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
            405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
        435                 440                 445

Gly Glu Pro Ile Ile Asn Phe Tyr Asp Pro Leu Val Phe Pro Ser Asn
        450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu His Asn Val Asn Ala
            485                 490                 495

Gly Lys Gly Tyr Ile Pro Glu Ala Pro Arg Asp Gly Gln Ala Tyr Val
            500                 505                 510

Arg Lys Asp Gly Glu Trp Val Leu Leu Ser Thr Phe Leu Ser Thr Thr
            515                 520                 525

Asn Leu Ile Thr Tyr Ile Ala Leu Thr Ala Ile Ser Leu Val Cys Gly
            530                 535                 540

Ile Leu Ser Leu Val Leu Ala Cys Tyr Leu Met Tyr Lys Gln Lys Ala
545                 550                 555                 560

Gln Gln Lys Thr Leu Leu Trp Leu Gly Asn Asn Thr Leu Gly Gln Met
            565                 570                 575

Arg Ala Thr Thr Lys Met
            580
```

COMPOSITIONS AND METHODS FOR MAKING AND USING VIRUS-LIKE PARTICLES (VLPS)

This application claims priority to U.S. provisional Application Ser. No. 62/735,503, filed Sep. 24, 2018, and to U.S. provisional Application Ser. No. 62/806,526 filed Feb. 15, 2019, each of which is herein incorporated by reference in its entirety.

STATEMENT REGARDING FEDERALLY SPONSORED RESEARCH

This invention was made with government support under grant number AI114809 awarded by the National Institutes of Health. The Government has certain rights in the invention.

A Sequence Listing has been submitted in an ASCII text file named "19435RevisedSequencelistingLRG" created on Jul. 1, 2021, consisting of 64,633 bytes, the entire content of which is herein incorporated by reference.

FIELD OF THE INVENTION

The present invention provides compositions and methods for using prophylactic and/or therapeutic vaccines to immunize subjects, and offspring of immunized female subjects, against respiratory syncytial virus (RSV). The invention also provides compositions and methods for producing increased yields of recombinant virus-like particles (VLPs).

BACKGROUND OF THE INVENTION

Efforts to develop a vaccine for respiratory syncytial virus (RSV) have focused primarily on the RSV fusion protein. The pre-fusion conformation of this protein, most effective in inducing potent neutralizing antibodies, is the focus of recent efforts in vaccine development (1). The first identification of mutations in the RSV F protein that stabilized the pre-fusion conformation was named DS-Cav1 (2) and this mutant pre-F protein has been shown to induce high titers of neutralizing antibodies, in contrast to wild type F protein and post-F protein. DS-Cav1 has been the focus of many laboratories and companies. However, at least three reports indicate that soluble DS-Cav1 pre-F is unstable and converts to the post-F form upon storage (3-5).

Furthermore, a significant step toward clinical trials and subsequent manufacture of virus-like particle (VLP) vaccines is the development of protocols for large-scale production of VLP vaccine candidates by cost-effective, robust manufacturing practices.

Thus, what is needed are compositions that stabilize DS-Cav1 pre-F protein for use in vaccines against RSV infection. Furthermore, there is a need for increasing the yield of VLPs for use in vaccines.

BRIEF DESCRIPTION OF THE DRAWINGS

FIG. 2A-B: Expression of chimera proteins and VLP content. Panel FIG. 2A: Shown is a western blot of total cell extracts of ELL-0 cells transfected with one of the cDNAs encoding the chimera proteins described in FIG. 1 and a cDNA encoding the H/G chimera. F proteins were detected using anti-RSV HR2 antibody. Panel FIG. 2B: a western blot of biotinylated RSV F proteins expressed at the surfaces of cells transfected as in panel FIG. 2A detected using anti-RSV HR2 antibody.

FIG. 3A-F: Expression of chimera proteins and VLP content: Panel FIG. 3A: Shown is a western blot of cell surface biotinylated RSV F proteins detected on the surfaces of ELL-0 cells (1×105 cells) transfected with each of the cDNAs encoding the chimera proteins described in FIG. 1. F proteins were detected using anti-RSV HR2 antibody. Panel FIG. 3B: Shown is a western blot of biotinylated RSV F proteins detected on surfaces of cells transfected as in panel FIG. 3A with the addition of a cDNA encoding the H/G chimera. Panel FIG. 3C-F: Western blots of proteins in purified VLPs adjusted for similar F protein content based on results shown in FIG. 27A-C. Panel FIG. 3C, F/F protein content; panel FIG. 3D, H/G protein content; panel FIG. 3E, NDV NP protein content; panel FIG. 3F, RSV G protein content. Results are representative of two separate experiments. Anti-RSV does not detect F protein. F0, uncleaved F/F chimera; F1, cleaved F/F chimera; H/G, NDV HN/RSVG protein chimera; NP, NDV NP protein; M, marker proteins.

FIG. 4A-E: Monoclonal antibody binding to VLPs. Binding to VLPs of mAb specific to sites common to both pre-fusion and post-fusion F proteins are shown in panels FIG. 4A-C. Panel FIG. 4A: motavizumab (site II); panel FIG. 4B: mAb 1112 (site I); mAb 1243 (site IV). Binding of pre-fusion specific mAb is shown in panels FIG. 4D (mAb D25, site 0) and FIG. 4E (mAb AM14, trimer specific Ab). Equivalent amounts of VLPs were bound to microtiter wells. Increasing dilutions of the Ab were added to the wells. Binding of Mab was detected using anti-human IgG coupled to HRP. Results are representative of three separate experiments.

FIG. 5A-C: Stability of pre-fusion F conformation in VLPs. Equivalent amounts of VLPs were incubated for 1 hour at different temperatures, pHs, or salt concentrations indicated. The binding of mAb D25 to the VLPs was quantified using anti-human IgG coupled to HRP. Results are presented as mAb D25 bound at each condition as a percent of the binding at 4° C. (panel FIG. 5A), or pH 7 (panel FIG. 5B), or 0.15 M salt (Panel FIG. 5C). Results are the average with standard deviations of 3 separate determinations.

FIG. 14A-B. (FIG. 14A) Post-fusion F/F DNA Sequence (SEQ ID NO:01), and (FIG. 14B) Post-fusion F/F protein Sequence (SEQ ID NO:02). POST ectodomain of RSV F sequence is in black text, and the transmembrane (TM) and cytoplasmic (CT) domains of the NDV F sequence is in underlined bold text.

FIG. 15A-B. (FIG. 15A) DS-CAV1 F/F DNA Sequence (i.e., Pre-fusion F/F DNA Sequence) (SEQ ID NO:03), and (FIG. 15B) DS-CAV1 F/F Protein Sequence (i.e., Pre-fusion F/F protein Sequence) (SEQ ID NO:04). DS-CAV1 mutant ectodomain of RSV F sequence is in black text. Mutations in the DS-CAV1 mutant ectodomain of RSV F sequence are in double-underlined bold text, foldon sequence is in italicized, underlined, bold text, and the transmembrane (TM) and cytoplasmic (CT) domains of the NDV F sequence is in underlined grey-shaded bold text.

FIG. 16A-B. (FIG. 16A) PR-DM F/F DNA Sequence (SEQ ID NO:05), and (FIG. 16B) encoded PR-DM F/F protein sequence (SEQ ID NO:06). PR-DM mutant ectodomain of RSV F sequence is in black text. Mutations (DM=N67I, S215P) in the PR-DM mutant ectodomain of RSV F sequence are in double-underlined bold text, foldon sequence is in italicized underlined bold text, and the transmembrane (TM) and cytoplasmic (CT) domains of the NDV F sequence is in underlined grey-shaded bold text.

FIG. 17A-B. (FIG. 17A) PR-TM F/F DNA Sequence (SEQ ID NO:07), and (FIG. 17B) encoded PR-TM F/F protein sequence (SEQ ID NO:08). PR-TM mutant ectodomain of RSV F sequence is in black text. Mutations (TM=N67I, S215P, D486N) in the PR-TM mutant ectodomain of RSV F sequence are in double-underlined bold text, foldon sequence is in italicized underlined bold text, and the transmembrane (TM) and cytoplasmic (CT) domains of the NDV F sequence is in underlined grey-shaded bold text.

FIG. 18A-B. (FIG. 18A) SC-DM F/F DNA Sequence (SEQ ID NO:09), and (FIG. 18B) SC-DM F/F protein sequence (SEQ ID NO:10). SC-DM mutant ectodomain of RSV F sequence is in black text. Mutations (DM=N67I, S215P) in the SC-DM mutant ectodomain of RSV F sequence are in double-underlined bold text, SC linker and Cleavage site mutations are in double-underlined bold italicized text, foldon sequence is in italicized underlined bold text, and the transmembrane (TM) and cytoplasmic (CT) domains of the NDV F sequence is in underlined grey-shaded bold text.

FIG. 19A-B. (FIG. 19A) SC-TM F/F DNA Sequence (SEQ ID NO:11), and (FIG. 19B) SC-TM F/F protein sequence (SEQ ID NO:12). SC-TM mutant ectodomain of RSV F sequence is in black text. Mutations (DM=N67I, S215P, D486N) in the SC-TM mutant ectodomain of RSV F sequence are in double-underlined bold text, SC linker and Cleavage site mutations are in double-underlined italicized bold text, foldon sequence is in italicized underlined bold text, and the transmembrane (TM) and cytoplasmic (CT) domains of the NDV F sequence is in underlined grey-shaded bold text.

FIG. 20A-B. (FIG. 20A) CMV IE, CAG Promoter Sequence (SEQ ID NO:14), and (FIG. 20B) pCaggs Sequence in BacMam Virus (SEQ ID NO:15). CMV, IECAG Promoter is in bold underlined text; NDV, RSV/NDV genes are inserted at the location shown in bold italics underlined text; pCaggs sequence is in black text.

FIG. 21A-D. (FIG. 21A) NDV NP Protein Sequence (SEQ ID NO:16). (FIG. 21B) NDV M Protein Sequence (SEQ ID NO:17). (FIG. 21C) H/G (NDV HN/RSV G) Protein Sequence (SEQ ID NO:18), bold underlined text is the NDV HN protein TM and CT domain sequences. RSV G protein ectodomain sequence is in black text. (FIG. 21D) SC-TM F/F Protein Sequence (SEQ ID NO:19), Mutations (DM=N67I, S215P, D486N) are in bold double-underlined text; SC linker+Cleavage site mutations are in bold double-underlined italicized text; Foldon Sequence is in bold italics underlined text; NDV F Sequences is in bold underlined grey-shaded text; RSV F Sequence is in black text.

(FIG. 22a,b) Protein expression levels and prefusion stability of RSV F SCA2 variants and processed variants (PRA2) with substitutions in RR1 (n=2-4). (FIG. 22c,d) Protein expression levels and prefusion stability of RSV F SCA2 variants with all 20 amino acid substitutions at position 215 (n=1) and (FIG. 22e,f) at position 67 (n=2). Protein expression levels in cell culture supernatants were tested 72 h post transfection and fraction of RSV F protein binding to prefusion specific CR9501 antibody on the day of harvest and after storage at 4° C. for indicated period of time. (FIGS. 22a,b,e and f)—bars represent average of 2-4 measurements, lines represent range of values; (FIG. 22c,

*d*)—bars represent single measurement. Amino acids are grouped according to physicochemical characteristics. Variants are based on strain A2.

FIG. 23A-D: Total anti-pre-F and post-F binding IgG in sera after immunization with different VLPs. Total anti-pre-F binding (Panels FIG. 23A, B) and post-F binding (Panels FIG. 23C, D) IgG in pooled sera at each time point after the boost immunization was determined by ELISA using soluble DS-Cav1 protein (panels FIGS. 23A and B) or soluble post-F protein (panels FIGS. 23C and D) as target antigen. Panels FIGS. 23A and C compare titers in DS-Cav1 VLP sera with those in sera from PR-DM or PR-TM VLP sera. Panels FIGS. 23B and D compare titers in DS-Cav1 VLP sera with those in sera from SC-DM or SC-TM VLP sera. Shown are the mean and standard deviations of three separate determinations. There were no statistically significant differences between titers at each time point.

FIG. 24A-C: Amounts of polyclonal antibody that blocks binding of representative mAb. Shown is the ability of anti-pre-F IgG in DS-Cav1 VLP sera and in Post-F VLP sera to block binding of mAb to soluble DS-Cav1 targets. Results are plotted as binding of the 200 ng of mAb in the presence of increasing amounts (ng/ml) of anti-pre-F IgG in each pooled serum. Binding of mAb is detected using anti-human IgG coupled to HRP as described in Materials and Methods. Panel FIG. 24A shows the inhibition of binding of mAb AM14 with different amounts of anti-pre-F IgG. Panel FIG. 24B shows inhibition of binding of mD25. Panel FIG. 24C shows inhibition of binding of motavizumab. Broken line, DS-Cav1 VLP sera; Solid line, Post-F VLP sera.

FIG. 25A-F: Blocking of binding of representative mAb by sera from PR, SC, and DS-Cav1 VLP immunizations. Shown are concentrations (ng/ml) of anti-pre-F IgG in pooled sera obtained at 4 weeks after boost immunizations with all pre-fusion F VLPs and with RSV infection that blocked 50% binding of mAb AM14 (panel FIG. 25A), D25 (panel FIG. 25B), and palivizumab (panel FIG. 25C) to soluble DS-Cav1 target protein. Panels FIGS. 25D, E, and F show concentrations (ng/ml) of anti-pre-F IgG in pooled sera that blocked binding of mAbs AM14, D25, and palivizumab, respectively, to soluble SC-TM target protein. The results are the mean of at least three separate determinations with standard deviations indicated. Significant differences between groups were determined by Student t test: * $p<0.0005$,  $p<0.005$, * $p<0.05$. Values at or near 10,000 ng/ml indicate failure of the sera to block binding of the tested mAb. Values at or somewhat above 2000 ng/ml indicated sera that only very weakly blocked binding. Values at or above 2000 ng/ml were quite variable from experiment to experiment as indicated by the large standard deviation.

Figure 26:
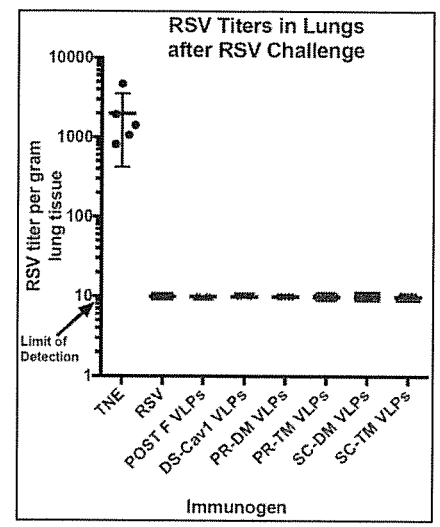

FIG. 26: RSV replication upon RSV challenge of VLP Immunized mice. Mice were primed with VLPs or RSV infected at day 0 and boosted at day 100. At day 147, the mice were infected with RSV ($1\times10^6$ pfu/animal) and four days later mice were sacrificed and the titers of RSV per gram of lung tissue were determined.

Figure 27A:
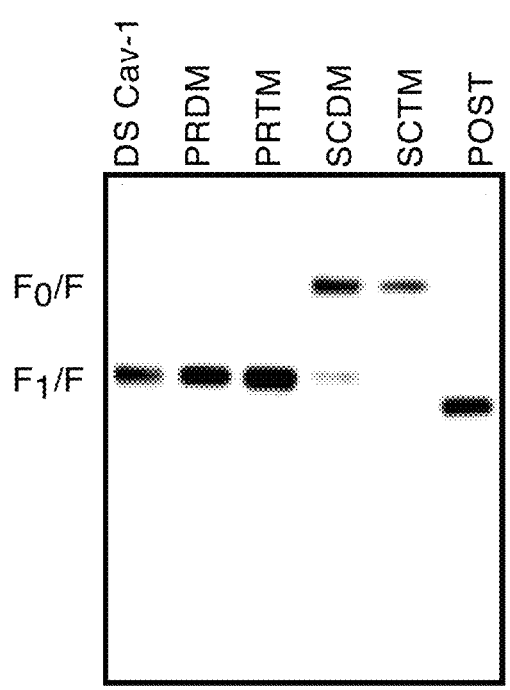
Figure 27B:
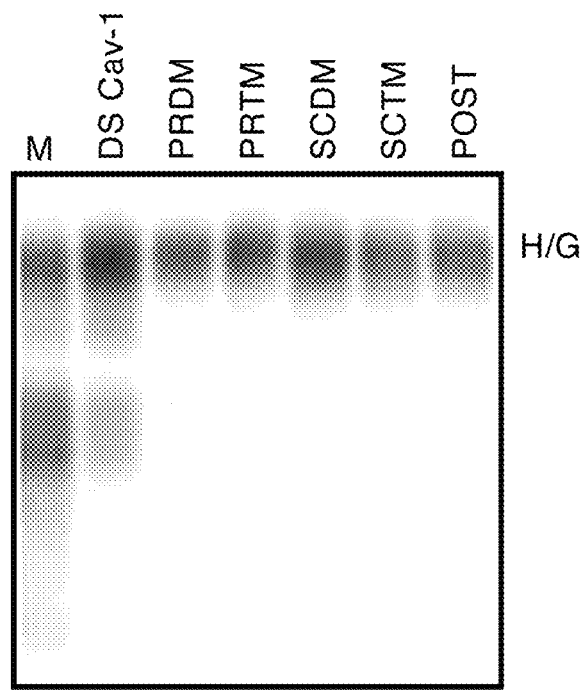
Figure 27C:
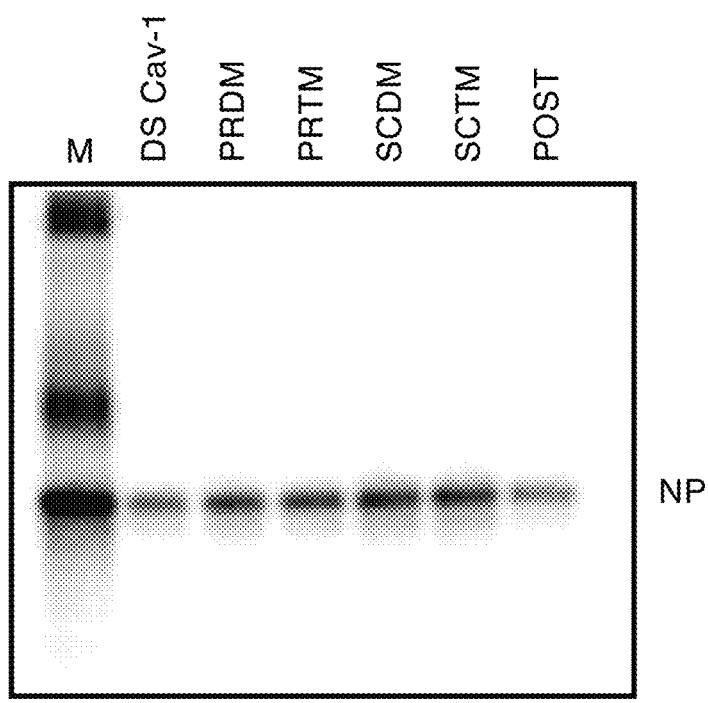

FIG. 27A-C: Western blot of protein content of VLPs prior to adjustment for equivalent amounts of F protein. Initial Characterization of VLP Protein Content: FIG. 27A-C shows VLP stocks of purified VLPs prior to final normalization of F protein content. Panel FIG. 27A: F/F protein content of VLP stocks; panel FIG. 27B, H/G protein content; panel C, NDV NP protein content. F0, uncleaved F/F chimera; F1, cleaved F/F chimera; H/G, NDV HN/RSVG protein chimera; NP, NDV NP protein; M, marker proteins.

FIG. 28A-E: Relative binding of representative mAbs to purified VLPs. Relative binding of decreasing amounts of pre-fusion F specific monoclonal antibodies to VLPs is shown in panels FIG. 28A (mAb D25: site 0) and FIG. 28B (mAb AM14, a trimer specific antibody). Binding to VLPs of mAb specific to sites common to both pre- and post-fusion F proteins is shown in panels FIG. 28C-E. Panel FIG. 28C: motavizumab (site II); Panel FIG. 28D: mAb 1112 (site I); Panel FIG. 28E: mAb 1243 (site IV). Equivalent amounts of F protein in VLPs were bound to microtiter wells. Increasing dilutions of the antibodies were added to the wells and binding of the mAb was detected using anti-human (mAb D25, AM14, and motavizumab) or anti-mouse (mAb 1112, 1243) IgG coupled to HRP. Results are from a separate experiment as that shown in FIG. 3A-F.

FIG. 29A-D: Blocking of binding of representative mAbs by sera from PR, SC, and DS-Cav1 immunizations. Shown are concentrations (ng/ml) of anti-pre-F IgG in pooled sera obtained at 2, 4, and 7 weeks after boost immunizations with all pre-fusion F VLPs, post-F VLPs, and RSV infection that block 50% binding of mAb AM14 (panel FIG. 29A) and D25 (panel FIG. 29B) to DS-Cav1 target protein. Panels FIGS. 29C and D show concentrations (ng/ml) of anti-pre-F IgG in pooled sera that block binding of mAbs AM14 and D25, respectively, to SC-TM target protein. The results are the mean of at least three separate determinations with standard deviations indicated. Values at or near 10,000 ng/ml indicate failure of the sera to block binding of the tested mAb. Values at or above 2000 ng/ml indicated sera that only very weakly blocked binding. Values at or above 2000 ng/ml were quite variable from experiment to experiment as indicated by the large standard deviation.

Figure 30:
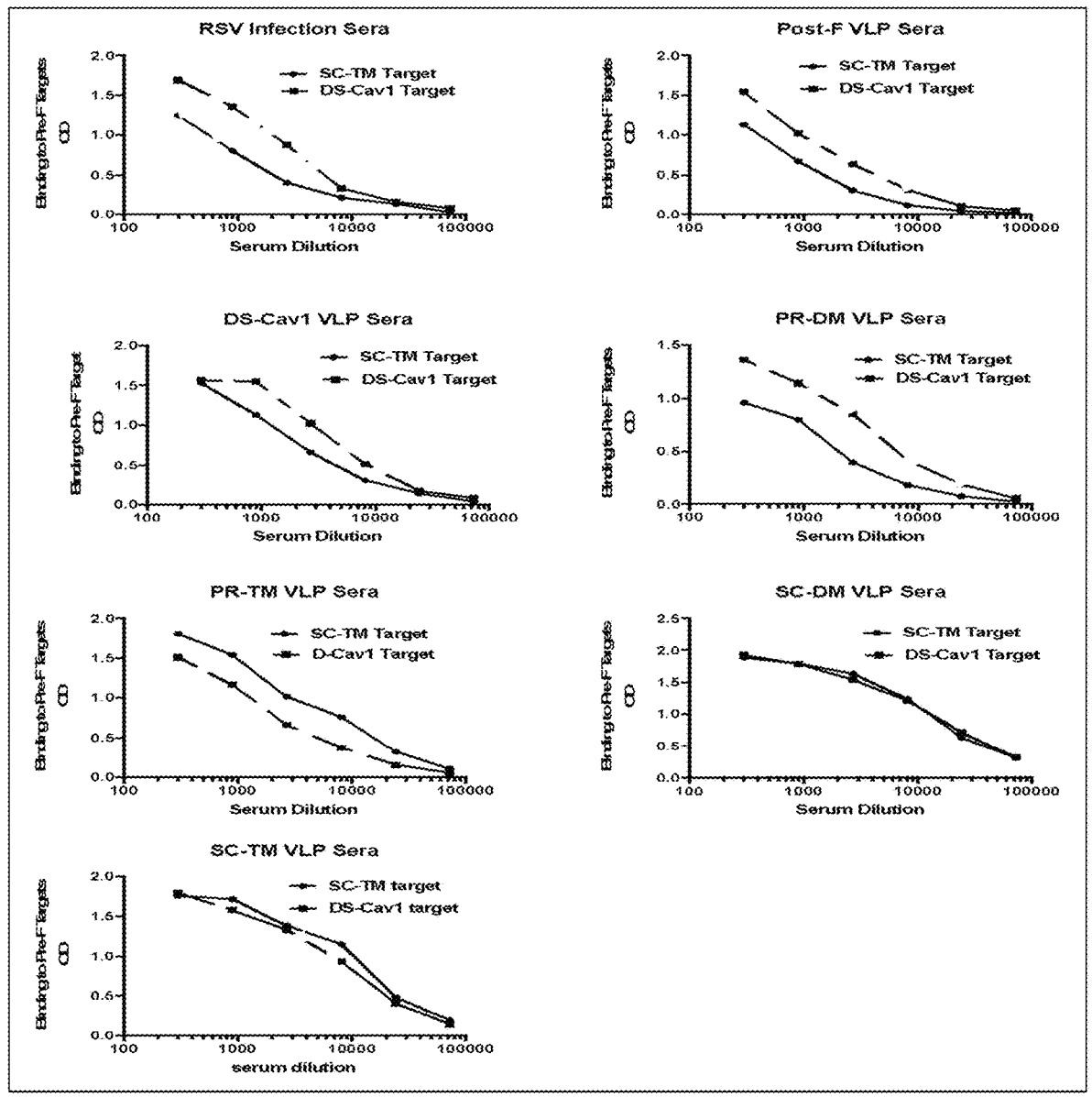

FIG. 30: Binding of sera induced by DS-Cav1 or SC-TM VLPs to soluble DS-Cav1 protein or soluble SC-TM protein. The binding of different dilutions of sera resulting from VLP immunizations or RSV infection to DS-Cav1 target (broken line) or SC-TM (solid line) target is shown.

DEFINITIONS

To facilitate understanding of the invention, a number of terms are defined below.

"SC linker" refers to a serine, glycine linker sequence exemplified by the amino acid sequence GSGSGRS (SEQ ID NO:13) (FIGS. 1, 18A-B, and 19A-B)

"PR-DM" sequence refers to a processed (i.e., cleaved at the natural proteolytic cleavage sites) double mutant sequence.

"PR-TM" sequence refers to a processed (i.e., cleaved) triple mutant sequence.

"SC-DM" sequence refers to a single chain (uncleaved) double mutant sequence.

"SC-TM" sequence refers to a single chain (uncleaved) triple mutant sequence.

The term "recombinant" molecule refers to a molecule that is produced using molecular biological techniques. Thus, "recombinant DNA molecule" refers to a DNA molecule that is comprised of segments of DNA joined together by means of molecular biological techniques. A "recombinant protein" or "recombinant polypeptide" as used herein refers to a protein molecule that is expressed using a recombinant DNA molecule. A "recombinant" virus-like particle (VLP) refers to a VLP that is expressed using a recombinant DNA molecule.

"Chimeric," "fusion" and "hybrid" composition (e.g., when in reference to an amino acid sequence, nucleotide sequence, virus, cell, etc.) refers to a composition containing parts from different origins. In one embodiment, the parts may be from different organisms, different tissues, different cells, different viruses, etc. In another embodiment, the parts may be from different proteins and/or genomic sequences from the same organism, same tissue, same cell, same virus, etc. In one embodiment, a chimeric amino acid sequence is a recombinant amino acid sequence that is produced by expressing operably linked nucleotide sequences that encode the different amino acid sequences.

"Operable combination" and "operably linked" when in reference to the relationship between nucleic acid sequences and/or amino acid sequences refers to linking (i.e., fusing) the sequences in frame such that they perform their intended function. For example, operably linking a promoter sequence to a nucleotide sequence of interest refers to linking the promoter sequence and the nucleotide sequence of interest in a manner such that the promoter sequence is capable of directing the transcription of the nucleotide sequence of interest and/or the synthesis of a polypeptide encoded by the nucleotide sequence of interest.

A "virus-like particle" and "VLP" interchangeably refer to a non-replicating, non-infectious particle shell that contains one or more virus proteins, lacks the viral RNA and/or DNA genome, and that approximately resembles live virus in external conformation. Methods for producing and characterizing recombinant VLPs containing Newcastle Disease Virus (NDV) proteins have been described (Pantua et al. (2006) J. Virol. 80:11062-11073; U.S. Pat. No. 7,951,384 issued to Morrison et al. on May 1, 2011; U.S. Pat. No. 8,974,797, issued to Morrison on Mar. 10, 2015, each of which is incorporated by reference). Further methods for producing NDV VLPs are disclosed herein.

"Newcastle disease virus virus-like particles" and "ND VLPs" refer to a VLP that contains one or more Newcastle disease virus proteins, such as matrix protein, nucleocapsid protein, fusion protein, and haemagglutinin-neuraminidase protein.

The term "matrix protein", "membrane protein", or "M protein" as used herein, means any protein localized between the envelope and the nucleocapsid core and facilitates the organization and maintenance of the virion or VLP structure and budding processes. Exemplary NDV M protein sequences include SEQ ID NO:17, and those described in U.S. Pat. No. 7,951,384 issued to Morrison et al. on May 1, 2011; U.S. Pat. No. 8,974,797, issued to Morrison on Mar. 10, 2015, each of which is incorporated by reference.

The term "nucleocapsid protein" or "NP protein" as used herein, means any protein that associates with genomic RNA (i.e., for example, one molecule per hexamer) and protects the RNA from nuclease digestion. Exemplary NP protein sequences from NDV include SEQ ID NO:16, and those described in U.S. Pat. No. 7,951,384 issued to Morrison et al. on May 1, 2011; U.S. Pat. No. 8,974,797, issued to Morrison on Mar. 10, 2015, each of which is incorporated by reference.

The term "fusion protein" or "F protein" as used herein, means any protein that projects from the envelope surface and mediates host cell entry by inducing fusion between the viral envelope and the cell membrane. However, it is not intended that the present invention be limited to functional F proteins. For example, an F protein may be encoded by a mutant F gene such as, but not limited to, F-K115Q. F-K115Q is believed to eliminate the normal cleavage and subsequent activation of the fusion protein. F-K115Q mimics naturally occurring F-protein mutations in avirulent NDV strains, and in cell culture, eliminates any potential side effects of cell-cell fusion on the release of VLPs. Exemplary NDV F protein sequences include those contained in SEQ ID NO:19, and those described in U.S. Pat. No. 7,951,384 issued to Morrison et al. on May 1, 2011; U.S. Pat. No. 8,974,797, issued to Morrison on Mar. 10, 2015, each of which is incorporated by reference.

The term "haemagglutinin-neuraminidase protein", "FIN protein", or G protein as used herein, means any protein that spans the viral envelope and projects from the surface as spikes to facilitate cell attachment and entry (i.e., for example, by binding to sialic acid on a cell surface). These proteins may possess both haemagglutination and neuraminidase activity. Exemplary NDV HN protein sequences include those contained in SEQ ID NO:18, and those described in U.S. Pat. No. 7,951,384 issued to Morrison et al. on May 1, 2011; U.S. Pat. No. 8,974,797, issued to Morrison on Mar. 10, 2015, each of which is incorporated by reference.

"Transgenic" and "recombinant" composition (e.g., nucleotide sequence, protein sequence, cell, virus, VLP, etc.) interchangeably refer to a composition that has been manipulated by any molecular biological technique to produce a composition that does not exist in nature, including, for example, the introduction of mutations, heterologous sequences, and the like.

The term "vaccine" refers to a pharmaceutically acceptable preparation that may be administered to a host to induce a humoral immune response (including eliciting a soluble antibody response) and/or cell-mediated immune response (including eliciting a cytotoxic T lymphocyte (CTL) response).

The term "administering" to a subject means delivering a molecule or composition (e.g., vaccine) to a subject. "Administering" includes prophylactic administration of the composition (i.e., before the disease or infection and/or one or more symptoms of the disease or infection are detectable) and/or therapeutic administration of the composition (i.e., after the disease or infection and/or one or more symptoms of the disease or infection are detectable). Administration also may be concomitant with (i.e., at the same time as, or during) manifestation of one or more symptoms of the disease or infection. Methods of administering the invention's compositions include, without limitation, administration in parenteral, oral, intraperitoneal, intranasal, topical and sublingual forms. Parenteral routes of administration include, for example, subcutaneous, intravenous, intramuscular, intrastemal injection, and infusion routes.

"Respiratory syncytial virus" and "RSV" interchangeably refer to a medium-sized (120-200 nm) enveloped virus that contains a lipoprotein coat and a linear negative-sense RNA genome (which must be converted to positive sense mRNA prior to translation). The genome is approximately 15,222 nucleotides in length and is composed of a single strand of RNA with negative polarity. It has 10 genes encoding 11 proteins (Lee et al. (2012) "Complete Genome Sequence of Human Respiratory Syncytial Virus Genotype A with a 72-Nucleotide Duplication in the Attachment Protein G Gene," Journal of Virology. 86 (24): 13810-1).

"Infection" and "infectious" when in reference to a virus refer to adsorption of the virus to the cell and penetration into the cell. A virus may be infectious (i.e., can adsorb to and penetrate a cell) without being replication competent (i.e., fails to produce new progeny virus particles).

"Transfection" is the process of introducing nucleic acid sequences into eukaryotic cells by non-viral methods, while "transformation" is the process of introducing nucleic acid sequences into bacterial cells by non-viral methods (e.g., using plasmids).

"Transduction" is the process of nucleic acid sequences into cells by via a viral vector.

"Transient" when in reference to transfection and/or transduction refer to the introduction of one or more nucleotide sequences of interest into a cell in the absence of integration of the nucleotide sequence of interest into the host cell's genome.

"Multiplicity of infection" and "moi" interchangeably refer to the number of viruses per cell.

"Symptom of RSV infection" include one or more of congested or runny nose, dry cough, fever, sore throat, headache, poor appetite, unusual tiredness (lethargy), irritability, wheezing, rapid breathing, difficulty in breathing, shallow breathing, bronchiolitis (inflammation of the small airways in the lung), pneumonia (infection of the lungs), and bluish color of the skin or in the nail beds due to lack of oxygen (cyanosis).

The terms "antigen," "immunogen," "antigenic," "immunogenic," "antigenically active," and "immunologically active" when made in reference to a molecule, refer to any substance that is capable of inducing a specific humoral and/or cell-mediated immune response. In a particular embodiment, the antigen comprises at least a portion of a virus protein sequence, and in particular an ectodomain of a virus protein sequence or a portion of the ectodomain. Exemplary antigenic sequences are include ectodomains of a membrane protein described in U.S. Pat. Nos. 7,951,384; 9,399,059; 9,216,212; and 8,974,797.

The term "ectodomain" when in reference to a membrane protein refers to the portion of the protein that is exposed on the extracellular side of a lipid bilayer of a cell, virus and the like.

Physiologically acceptable "carrier" and "diluent" for vaccine preparation include water, saline solution, human serum albumin, oils, polyethylene glycols, aqueous dextrose, glycerin, propylene glycol or other synthetic solvents. Carriers may be liquid carriers (such as water, saline, culture medium, saline, aqueous dextrose, and glycols) or solid carriers (such as carbohydrates exemplified by starch, glucose, lactose, sucrose, and dextrans, anti-oxidants exemplified by ascorbic acid and glutathione, and hydrolyzed proteins).

The term "expression vector" refers to a nucleotide sequence containing a desired coding sequence and appropriate nucleic acid sequences necessary for the expression (i.e., transcription into RNA and/or translation into a polypeptide) of the operably linked coding sequence in a particular host cell. Expression vectors are exemplified by, but not limited to, plasmid, phagemid, shuttle vector, cosmid, virus, chromosome, mitochondrial DNA, plastid DNA, and nucleic acid fragments thereof. Nucleic acid sequences used for expression in prokaryotes include a promoter, optionally an operator sequence, a ribosome binding site and possibly other sequences. Eukaryotic cells are known to utilize promoters, enhancers, and termination and polyadenylation signals.

"Mammalian subject" includes human, non-human primate, murine, ovine, bovine, ruminant, lagomorph, porcine, caprine, equine, canine, felines, ave, etc.).

A subject "in need" of reducing one or more symptoms of a disease or infection, and/or "in need for a particular treatment (such as immunization) against a disease or infection includes a subject that exhibits and/or is at risk of exhibiting one or more symptoms of the disease or infection. For Example, subjects may be at risk based on family history, genetic factors, environmental factors, etc. This term includes animal models of the disease. Thus, administering a composition (which reduces a disease or infection and/or which reduces one or more symptoms of a disease or infection) to a subject in need of reducing the disease or infection and/or of reducing one or more symptoms of the disease or infection includes prophylactic administration of the composition (i.e., before the disease or infection and/or one or more symptoms of the disease or infection are detectable) and/or therapeutic administration of the composition (i.e., after the disease or infection and/or one or more symptoms of the disease or infection are detectable). The invention's compositions and methods are also useful for a subject "at risk" for disease or infection refers to a subject that is predisposed to contracting and/or expressing one or more symptoms of the disease or infection. This predisposition may be genetic (e.g., a particular genetic tendency to expressing one or more symptoms of the disease or infection, such as heritable disorders, immunosuppression etc.), age, or due to other factors (e.g., environmental conditions, exposures to detrimental compounds, including carcinogens, present in the environment, etc.). It is not intended that the present invention be limited to any particular signs or symptoms. Thus, it is intended that the present invention encompass subjects that are experiencing any range of disease or infection, from sub-clinical symptoms to full-blown disease or infection, wherein the subject exhibits at least one of the indicia (e.g., signs and symptoms) associated with the disease or infection.

"Immunogenically effective amount" and "immunologically effective amount" interchangeably refer to that amount of a molecule that elicits and/or increases production of an "immune response" (i.e., production of specific antibodies and/or induction of a cytotoxic T lymphocyte (CTL) response) in a host upon vaccination with the molecule.

"Antibody" refers to an immunoglobulin (e.g., IgG, IgM, IgA, IgE, IgD, etc.) and/or portion thereof that contains a "variable domain" (also referred to as the "Fv region") that specifically binding to an antigen.

The term "specifically binds" and "specific binding" when made in reference to the binding of antibody to a molecule (e.g., peptide) or binding of a cell (e.g., T-cell) to a peptide, refer to an interaction of the antibody or cell with one or more epitopes on the molecule where the interaction is dependent upon the presence of a particular structure on the molecule. For example, if an antibody is specific for epitope "A" on the molecule, then the presence of a protein containing epitope A (or free, unlabeled A) in a reaction containing labeled "A" and the antibody will reduce the amount of labeled A bound to the antibody. In one embodiment, the level of binding of an antibody to a molecule is determined using the "IC50" i.e., "half maximal inhibitory concentration" that refer to the concentration of a substance (e.g., inhibitor, antagonist, etc.) that produces a 50% inhibition of a given biological process, or a component of a process (e.g., an enzyme, antibody, cell, cell receptor, microorganism, etc.). It is commonly used as a measure of an antagonist substance's potency.

The term "control" as used herein when in reference to a sample (e.g., a first vaccine, first VLP, first amino acid sequence, first nucleotide sequence, etc.) refers to any type of sample that one of ordinary skill in the art may use for comparing to a test sample (e.g., a second vaccine, second VLP, second amino acid sequence, second nucleotide sequence, etc.) by maintaining the same conditions in the control and test samples, except in one or more particular factors. These factors are exemplified by the presence of mutations (deletions, insertions, additions, etc.) and/or of different sequences (e.g., foldon sequence, linker sequence, etc.) in the test nucleotide sequence and/or test amino acid sequence. In one embodiment, the comparison of the control and test samples is used to infer a causal significance of this varied one or more factors.

Figures 22A, 22B:
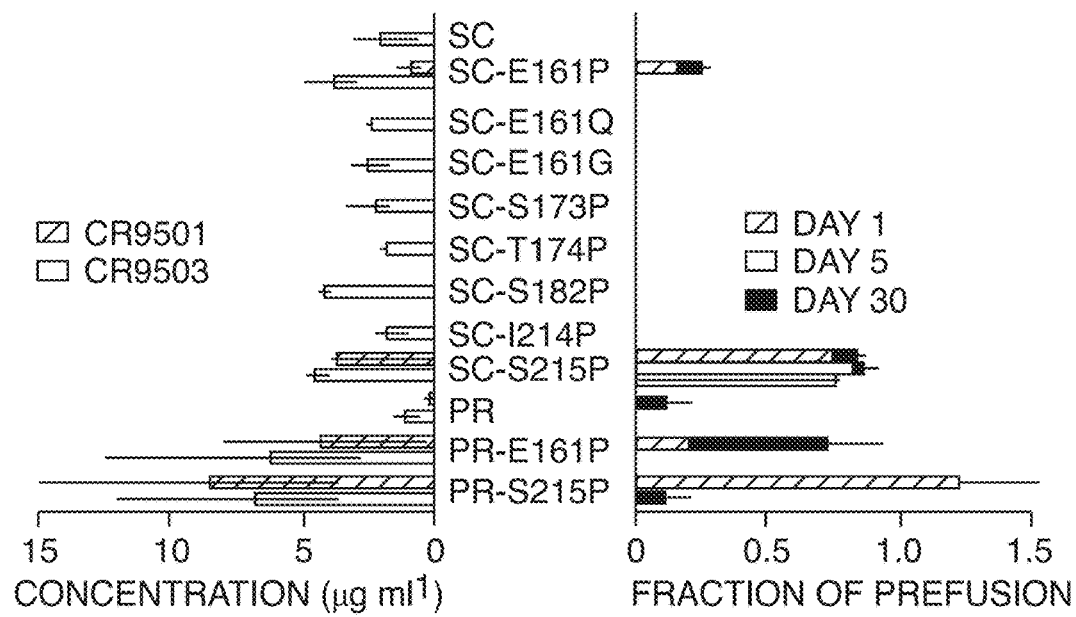
FIG. 22A-F. Amino acid substitutions at positions 67 and 215 increase expression level and prefusion stability of the F protein.
Figures 22C, 22D:
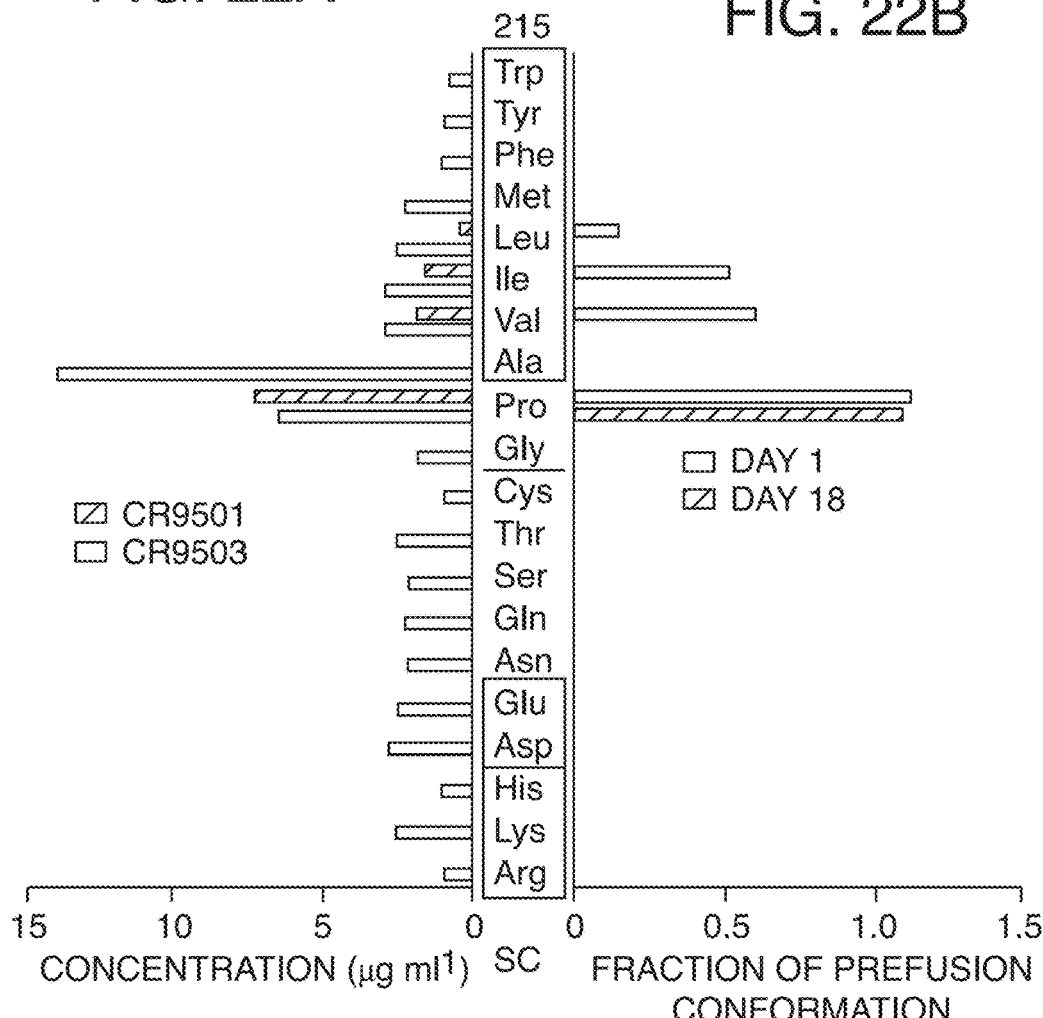
Figures 22E, 22F:
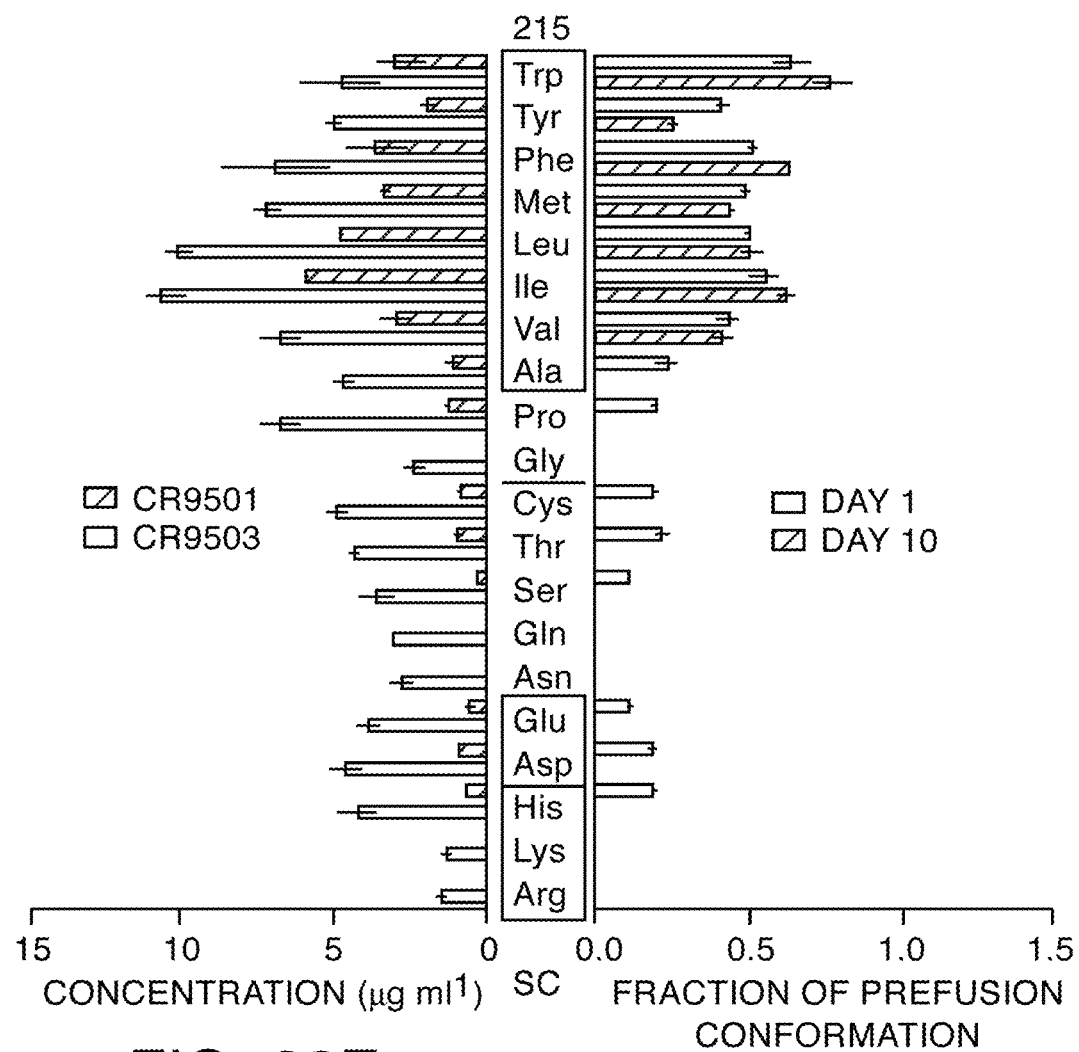

A "stabilized" first polypeptide sequence that contains one or more mutations relative to second polypeptide sequence means that the first polypeptide sequence has an increased expression level compared to the second polypeptide sequence. For example, for stabilizing the α4-α5 hinge loop of the prefusion conformation of RSV F in order to preserve the protein in the prefusion conformation and to dramatically increase expression levels, the transition to the postfusion conformation may be prevented by stabilizing the regions between the secondary structural elements that assembled into a long coiled-coil during the transformation from pre- to postfusion RSV F as described in Krarup, et al (3). To stabilize the turns between α2-α3, α3-β3, β3-β4 and α4-α5, proline residues were introduced because of their restricted backbone dihedral angles Of all single amino acid substitutions at turns, substitution of position 161, 182 and 215 with proline resulted in higher expression levels, and E161P and S215P also increased protein stability (FIGS. 22a and b). When the E161P or S215P were introduced in a furin-processed (PR) version of RSV F without the short loop, the expression of both increased more than sixfold and at day 1 the amount of prefusion conformation was ~70% for PR-E161P and 100% for the PR-S215P variant (FIGS. 22a and b). To understand the strong stabilizing effect of S215P, all 20 substitutions at position 215 were made and the variants were tested for expression and stability of prefusion F protein. As shown in FIGS. 22a and b, only proline had a major impact on the stability and expression whereas some medium-sized hydrophobic side chains had a minor effect.

The terms "reduce," "inhibit," "diminish," "suppress," "decrease," and grammatical equivalents (including "lower," "smaller," etc.) when in reference to the level or yield of any molecule (e.g., amino acid sequence, and nucleic acid sequence, antibody, etc.), cell, virus, VLP, and/or phenomenon (e.g., symptom of infection, symptom of disease, level of antibody, level of protection against RSV infection, level of expression of a gene, level of binding of two molecules such as binding of an antibody to an antigen, specificity of binding of two molecules, affinity of binding of two molecules, specificity to disease, sensitivity to disease, affinity of binding, etc.) in a first sample (or in a first subject) relative to a second sample (or relative to a second subject), mean that the quantity of molecule, cell and/or phenomenon in the first sample (or in the first subject) is lower than in the second sample (or in the second subject) by any amount that is statistically significant using any art-accepted statistical method of analysis. In one embodiment, the quantity of molecule, cell and/or phenomenon in the first sample (or in the first subject) is at least 10% lower than, at least 25% lower than, at least 50% lower than, at least 75% lower than, and/or at least 90% lower than the quantity of the same molecule, cell and/or phenomenon in the second sample (or in the second subject). In another embodiment, the quantity of molecule, cell, and/or phenomenon in the first sample (or in the first subject) is lower by any numerical percentage from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100% lower than the quantity of the same molecule, cell and/or phenomenon in the second sample (or in the second subject). In one embodiment, the first sample (or the first subject) is exemplified by, but not limited to, a sample (or subject) that has been manipulated using the invention's compositions and/or methods. In a further embodiment, the second sample (or the second subject) is exemplified by, but not limited to, a sample (or subject) that has not been manipulated using the invention's compositions and/or methods. In an alternative embodiment, the second sample (or the second subject) is exemplified by, but not limited to, a sample (or subject) that has been manipulated, using the invention's compositions and/or methods, at a different dosage and/or for a different duration and/or via a different route of administration compared to the first subject. In one embodiment, the first and second samples (or subjects) may be the same, such as where the effect of different regimens (e.g., of dosages, duration, route of administration, etc.) of the invention's compositions and/or methods is sought to be determined on one sample (or subject). In another embodiment, the first and second samples (or subjects) may be different, such as when comparing the effect of the invention's compositions and/or methods on one sample (subject), for example a patient participating in a clinical trial and another individual in a hospital.

The terms "increase," "elevate," "raise," and grammatical equivalents (including "higher," "greater," etc.) when in reference to the level or yield of any molecule (e.g., amino acid sequence, and nucleic acid sequence, antibody, etc.), cell, virus, VLP, and/or phenomenon (e.g., symptom of infection, symptom of disease, level of antibody, level of protection against RSV infection, level of expression of a gene, level of binding of two molecules such as binding of an antibody to an antigen, specificity of binding of two molecules, affinity of binding of two molecules, specificity to disease, sensitivity to disease, affinity of binding, etc.), mean that the quantity of the molecule, cell and/or phenomenon in the first sample (or in the first subject) is higher than in the second sample (or in the second subject) by any amount that is statistically significant using any art-accepted statistical method of analysis. In one embodiment, the quantity of the molecule, cell and/or phenomenon in the first sample (or in the first subject) is at least 10% greater than, at least 25% greater than, at least 50% greater than, at least 75% greater than, and/or at least 90% greater than the quantity of the same molecule, cell and/or phenomenon in the second sample (or in the second subject). This includes, without limitation, a quantity of molecule, cell, and/or phenomenon in the first sample (or in the first subject) that is at least 10% greater than, at least 15% greater than, at least 20% greater than, at least 25% greater than, at least 30% greater than, at least 35% greater than, at least 40% greater than, at least 45% greater than, at least 50% greater than, at least 55% greater than, at least 60% greater than, at least 65% greater than, at least 70% greater than, at least 75% greater than, at least 80% greater than, at least 85% greater than, at least 90% greater than, and/or at least 95% greater than the quantity of the same molecule, cell and/or phenomenon in the second sample (or in the second subject). In one embodiment, the first sample (or the first subject) is exemplified by, but not limited to, a sample (or subject) that has been manipulated using the invention's compositions and/or methods. In a further embodiment, the second sample (or the second subject) is exemplified by, but not limited to, a sample (or subject) that has not been manipulated using the invention's compositions and/or methods. In an alternative embodiment, the second sample (or the second subject) is exemplified by, but not limited to, a sample (or subject) that has been manipulated, using the invention's compositions and/or methods, at a different dosage and/or for a different duration and/or via a different route of administration compared to the first subject. In one embodiment, the first and second samples (or subjects) may be the same, such as where the effect of different regimens (e.g., of dosages, duration, route of administration, etc.) of the invention's compositions and/or methods is sought to be determined on one sample (or subject). In another embodiment, the first and second samples (or subjects) may be different, such as when comparing the effect of the invention's compositions and/or methods on one sample (subject), for example a patient participating in a clinical trial and another individual in a hospital.

SUMMARY OF THE INVENTION

The invention provides a vaccine comprising a) a recombinant Newcastle disease virus-like particle (ND VLP), said ND VLP comprises recombinant chimeric polypeptide, said recombinant chimeric polypeptide comprising one or more mutation-stabilized pre-fusion F proteins, and b) a physiologically acceptable carrier. In one embodiment, said one or more mutation-stabilized pre-fusion F proteins comprises one or more of SC-TM F/F protein sequence SEQ ID NO:12 and SC-DM F/F protein sequence SEQ ID NO:10.

The invention provides a recombinant chimeric polypeptide comprising one or more of SC-TM F/F protein sequence SEQ ID NO:12, SC-DM F/F protein sequence SEQ ID NO:10, and mutation-stabilized pre-fusion F proteins. In a particular embodiment, the recombinant chimeric polypeptide comprises SC-TM F/F protein sequence SEQ ID NO:12.

The invention also provides a recombinant Newcastle disease virus-like particle (ND VLP) comprising one or more of the recombinant chimeric polypeptides described herein, such as SC-TM F/F protein sequence SEQ ID NO:12 and SC-DM F/F protein sequence SEQ ID NO:10.

The invention additionally provides a vaccine comprising any one or more of the recombinant ND VLPs described herein, and a physiologically acceptable carrier.

The invention further provides an expression vector encoding any one or more of the recombinant VLPs described herein.

The invention also provides an expression vector encoding any one or more of the recombinant chimeric polypeptides described herein, such as SC-TM F/F protein sequence SEQ ID NO:12 and SC-DM F/F protein sequence SEQ ID NO:10.

The invention also provides a method for immunizing a first mammalian subject against respiratory syncytial virus (RSV), comprising administering an immunologically effective amount of one or more of the vaccines described herein to a mammalian subject to produce a treated subject, wherein said administering is under conditions to produce an immune response to one or more of said RSV protein and an immunogenic portion thereof. In one embodiment, said recombinant VLP comprises SC-TM F/F protein sequence SEQ ID NO:12. In a further embodiment, said immune response comprises an increased level of antibody in serum of said treated subject, wherein said antibody specifically binds with one or more of said respiratory syncytial virus (RSV) protein and said immunogenic portion thereof. In a particular embodiment, the mammalian subject is female. In one embodiment, said immunizing is before birth (such as during gestation) of an offspring of said female subject.

The invention also provides a method for immunizing a mammalian subject against respiratory syncytial virus (RSV), comprising administering, prior to birth of said mammalian subject, an immunologically effective amount of one or more vaccines described herein to a mother of a first mammalian subject to produce a treated mother, wherein said administering is under conditions to produce an immune response to one or more of said respiratory syncytial virus (RSV) protein and an immunogenic portion thereof in said treated mother. In one embodiment, said administering is during gestation of said mammalian subject by said mother. In another embodiment, said immune response comprises an increased level of antibody in serum of said treated mother, wherein said antibody specifically binds with one or more of said respiratory syncytial virus (RSV) protein and said immunogenic portion thereof. In another embodiment, said immune response comprises an increased level of antibody in serum of said mammalian subject, wherein said antibody specifically binds with one or more of said respiratory syncytial virus (RSV) protein and said immunogenic portion thereof. In a particular embodiment, said immune response comprises an increased level of protection of said mammalian subject against RSV infection.

The invention additionally provides a transgenic baculovirus expression vector that comprises baculovirus genome, said genome comprising a first nucleotide sequence encoding a virus-like particle (VLP), said first nucleotide sequence operably linked to a mammalian promoter sequence.

The invention also provides a method for producing recombinant virus-like particles (VLPs) comprising infecting a cell selected from the group consisting of mammalian cell and avian cell, in the presence of sodium butyrate, with any one or more transgenic baculovirus expression vector described herein. In one embodiment, said infecting produces said VLPs at a yield that is higher than in the absence of said sodium butyrate. In a further embodiment, said method comprises (a) prior to said infecting, the step of concentrating a sample for said transgenic baculovirus expression vectors to produce a concentrated sample, and (b) using said concentrated sample in the infecting step. In one embodiment, said method further comprises, prior to said concentrating step, infecting an insect cell with said vector to produce said recombinant baculovirus.

The invention additionally provides a recombinant virus-like particle (VLP) produced by the any one or more of the methods described herein.

The invention also provides a method for producing recombinant virus-like particles (VLPs) comprising a) providing a first sample that contains one or more transgenic baculovirus expression vector described herein, b) concentrating said first sample for said transgenic baculovirus expression vectors to produce a concentrated sample, and c) infecting a cell selected from the group consisting of mammalian cell and avian cell with said concentrated sample to produce said recombinant VLPs. In one embodiment, said infecting produces said VLPs at a yield that is higher than in the absence of said concentrating. In another embodiment, said infecting is in the presence of sodium butyrate.

The invention also provides a recombinant virus-like particle (VLP) produced by any one or more of the methods described herein.

The invention additionally provides a recombinant Newcastle disease virus-like particle (ND VLP) comprising recombinant chimeric polypeptide comprising one or more mutation-stabilized pre-fusion F proteins. In one embodiment, said recombinant chimeric polypeptide comprises amino acid changes introduced into the ectodomain sequences to generate said one or more mutation-stabilized pre-fusion F proteins. In a further embodiment, the sequences encoding the ectodomains of said one or more mutation-stabilized pre-fusion F proteins are fused to the sequences encoding the transmembrane (TM) and cytoplasmic (CT) domains of the NDV F proteins. In yet another embodiment, said recombinant chimeric polypeptide comprises one or more of SC-TM F/F protein sequence SEQ ID NO:12 and SC-DM F/F protein sequence SEQ ID NO:10.

DESCRIPTION OF THE INVENTION

The present invention provides compositions and methods for using prophylactic and/or therapeutic vaccines to immunize subjects, and offspring of immunized female subjects, against respiratory syncytial virus (RSV). The invention also provides compositions and methods for producing increased yields of recombinant virus-like particles (VLPs). The invention is further described under (A) Compositions and methods for vaccination against RSV infection, and (B) Methods for Production of VLPs.

A) Compositions and Methods for Vaccination Against RSV Infection.

At least three reports teach that soluble DS-Cav1 pre-F is unstable and converts to the post-F form upon storage (3-5). This suggests that VLPs containing DS-Cav1 pre-F are not optimal for use as a vaccine. Thus, the invention addresses the need for compositions that stabilize pre-F protein for use in vaccines against RSV infection.

Data herein indicate that not all mutation stabilized pre-fusion F proteins are the same. Data herein indicate that different mutant stabilized pre-F proteins in VLPs have somewhat different conformations or accessibility of mAb epitopes and that there are differences in the levels and specificities of antibodies as well as NAbs titers induced by these VLP associated pre-fusion F proteins. For selection of the appropriate form of the pre-fusion F protein for a vaccine candidate, experiments need to be extended to mice and cotton rats previously infected with RSV, a situation more closely mimicking the human population. Prior RSV infection (RSV priming) may well alter responses after different Pre-F VLP boost immunizations.

There have been only a few reports of systematic comparisons, other than total neutralizing antibody titers, of any differences between alternative versions of stabilized pre-fusion F proteins with respect to the properties of the protective antibodies they induce. Because the reported instability of the pre-fusion conformation of the soluble DS-Cav1 pre-fusion F protein could negatively impact the immune response to the protein, we explored the properties of alternative pre-fusion RSV F proteins. Kraup, et al [27] have described a number of different mutations of RSV F protein reported to stabilize the RSV pre-fusion F protein. To generate the data in Examples 2-11, four of these mutants were selected for characterization of protein expression, efficiency of assembly into VLPs, the stability of the pre-fusion conformation, the mAb reactivity of VLP associated F protein, and the induction of neutralizing antibody responses in mice, comparing results with VLP associated DS-Cav1 pre-F protein. In addition, the ability to block binding of prototype monoclonal antibodies to protein targets by serum antibodies induced by each VLP was quantified. Taken together, the results are consistent with the conclusion that not all mutation stabilized RSV pre-F proteins have the same conformation or induce the same antibody responses. They do not induce similar levels of neutralizing antibodies nor do they induce serum antibodies with similar antibody specificities.

Data herein show a significant difference between the pre-F proteins was their levels of expression. The PR and SC mutants were expressed, on cell surfaces, at significantly higher levels than the DS-Cav1 F mutant and the post-F mutant. This finding suggested that the synthesis, folding, or intracellular transport of the PR and SC mutant proteins are more efficient than that of DS-Cav1 F protein. This difference likely accounts for the different ratios of F and H/G and F and NP in the different VLPs.

Data herein show that the reactivity of the different VLPs to the pre-fusion specific anti-F protein monoclonal antibodies were surprisingly different. The PR-TM and SC-TM VLPs bound both mAbs D25 and AM14 at higher levels than DS-Cav1 indicating differences from DS-Cav1 VLPs. Without intending to limit the invention to any particular mechanism, these differences may be due to altered accessibility of the mAb binding sites, by different affinities of the mAb to the different F proteins in VLPs, or differences in the conformation of the VLP associated F protein pre-fusion epitopes. By contrast, PR-DM bound both antibodies quite poorly and at much lower levels than DS-Cav1. These results suggest that PR-DM mutant protein may be predominantly in a post-fusion conformation, or more likely in a conformation intermediate between the pre-F and post-F proteins. Monoclonal antibodies to sites in common with both pre- and post-fusion F, Motavizamab®, a site II antibody and mAb1112 (site I), bound to all five pre-F VLPs at similar levels. However, there were some differences in the binding of the mAb 1243, a site IV antibody, again suggesting F protein conformational differences between the VLPs.

There are three reports of the instability of soluble DS-Cav1 pre-F conformation [27-29] and, indeed, we have observed the loss of reactivity of this protein to mAb D25 upon storage. However, this protein, assembled into VLPs, was stable during incubation at high temperatures, high and low salt concentrations, high and low pH, multiple cycles of freeze thaw, or upon prolonged storage. The pre-fusion conformation of the other four VLP associated pre-F proteins was also stable. Without intending to limit the invention to any particular mechanism, possibly anchoring of the proteins in VLP membranes helps to stabilize the pre-fusion conformation. Additionally, the fusion of the ectodomains of these proteins to the NDV TM and CT domains and the inclusion of the foldon sequence at the carboxyl terminus of the F protein ectodomains may serve to stabilize the pre-fusion F protein conformation.

Data herein show that measures of neutralizing antibodies (NAbs) in sera showed that the PR-TM and PR-DM VLPs stimulated levels quite similar to that stimulated by the DS-Cav1 VLPs. Interestingly, the PR-DM VLPs were as effective as the DS-Cav1 and PR-TM VLPs in induction of NAbs in spite of the finding that the PR-DM VLPs bound pre-fusion specific mAbs D25 and AM 14 very poorly. We have previously reported that Post-F VLPs after both a prime and boost in mice stimulated about 1.5 to 2 fold lower neutralization titers than DS-Cav1 VLPs [24]. Thus, without intending to limit the invention to any particular mechanism, the titers after PR-DM VLP immunization may reflect a mix of pre-F and post-F content in these VLPs. Alternatively, without intending to limit the invention to any particular mechanism, the PR-DM may be in a conformation intermediate between pre- and post-F but a conformation that stimulates neutralizing antibodies. By contrast, SC-TM VLPs stimulated NAbs titers three-fold higher than DS-Cav1 VLPs indicating that this version of pre-fusion F protein more effectively stimulated NAbs in mice, a result consistent with increased binding of mAb AM14 and D25 to these VLPs. SC-DM VLPs stimulated NAb levels twice that of DS-Cav1 consistent with binding of D25 mAb to this VLP. This VLP may stimulate other pre-fusion specific antibodies not tested here.

Data herein show that there were no significant differences in the levels of total anti-pre-F or post-F-binding IgGs stimulated by the five different VLPs. This result suggests that different NAbs titers may be due to different populations of specific antibodies in each serum. With the goal of defining potential differences in the populations of antibodies induced by the different VLPs, we quantified the amounts of anti-pre-F binding IgG required to block the binding of a given amount of monoclonal antibody to a pre-fusion target protein. Our results showed that the five-different pre-F VLPs induced quite different amounts of antibodies that blocked binding of D25, AM14, or Palivizumab® to the target F protein.

Complicating this analysis was that the data herein found that the measured concentration of antibody that blocked mAb binding varied with the target F protein used. For example, the measured ng/ml of D25-blocking antibodies and AM14-blocking antibodies induced by DS-Cav1 VLPs were quite different using soluble DS-Cav1 as target compared to values obtained using soluble SC-TM protein target. These results further support our idea that alternative pre-F proteins induce different populations of anti-F antibodies.

There are potentially several reasons for ability of sera to block the binding of a mAb to a target protein. Without intending to limit the invention to any particular mechanism, the polyclonal sera may have antibodies that bind directly to the epitope recognized by the mAb and thus they will directly block binding of that mAb. However, without intending to limit the invention to any particular mechanism, mAb blocking may also involve relative affinities of the antibodies to the specific mAb binding site. Without intending to limit the invention to any particular mechanism, it is likely that polyclonal antibodies with a lower avidity will not block binding as effectively as antibodies that have undergone affinity maturation. Indeed, at least for mAb D25, polyclonal antibodies from 4 and 7 weeks post boost in general blocked mAb binding better than antibodies at 2 weeks post boost (FIG. 29A-D). Differences could also relate to the affinities of the mAb to the target. For example, Motavizumab® is reported to have a higher affinity for site II than Palivizumab® [40]. This differential affinity could account for the observation that approximately 700 ng/ml of DS-Cav1 VLP sera was required to block the binding of motavizumab (FIG. 24A-C, panel FIG. 24C) to DS-Cav1 target while only 350 ng/ml of the same sera was required to block Palivizumab® binding (FIG. 25A-F, panel FIG. 25C). Without intending to limit the invention to any particular mechanism, it is also possible that polyclonal antibodies in sera will be directed, not to the specific epitope recognized by the mAb but to regions of the molecule in the vicinity of the epitope. Binding of these antibodies to off-site targets may block mAb binding to its site by masking the epitope, a concept described by Mousa, et al, for antibodies to site II [41]. Results of competition of any of the sera with the mAbs could be due to any or all of these possible mechanisms.

Based on the combined results herein, particularly of mAb binding to VLPs, neutralization titers of sera in mice, and competition for binding of mAbs by sera induced by the five pre-F VLPs, one preferred embodiment for antigens for inclusion in a vaccine includes the SC pre-fusion F protein, particularly SC-TM. The ultimate selection will depend upon results of protection from RSV challenge. These studies are not informative in mice since even a single RSV infection results in complete protection of mice from RSV challenge due, at least in part, to the limited permissiveness of mice to RSV replication. Thus, there was no detectable RSV in lungs of any of the immunized mice four days after RSV challenge at day 147. Challenge studies, as well as assays for lung pathology after challenge, are better accomplished in cotton rats which are quite permissive to RSV. Indeed, data herein clearly suggest significant differences in the protection provided by immunization with the different pre-F VLPs.

Data herein (Examples 2-8) demonstrate the use of ND VLPs containing four alternate forms of the mutation stabilized pre-fusion F proteins, as vaccine candidates. To determine if there are differences in alternate versions of pre-fusion F proteins, data herein was obtained using, as vaccine candidates, of five virus-like particles (VLPs) each containing one of the five different stabilized pre-fusion F proteins, including DS-Cav1 protein. The expression of the alternative pre-F proteins, their assembly into ND VLPs, their pre-fusion conformation stability in ND VLPs, the anti-F protein monoclonal antibody reactivity of the ND VLPs, and their induction of immune responses after immunization of mice and cotton rats, were characterized, comparing results with ND VLP associated DS-Cav1 pre-F as well as post-F protein. Data herein (Examples 2-8) show that the conformation and immunogenicity of alternative ND VLP associated stabilized pre-fusion RSV F proteins are different. Data herein (Examples 2-8) also demonstrated that two mutant F proteins (i.e., SC-TM F/F protein sequence (SEQ ID NO:12) and SC-DM F/F protein sequence (SEQ ID NO:10)) were superior to DS-Cav1 (SEQ ID NO:04) with respect to induction of neutralizing antibodies in a subject (Example 6), including a pregnant subject (Example 7). Data herein also demonstrate that SC-TM F/F protein sequence (SEQ ID NO:12) was superior to DS-Cav1 (SEQ ID NO:04) with respect to protecting the offspring of mothers that had been immunized with this sequence.

In particular, without intending to limit the invention to any particular mechanism, data herein (Examples 2-8) show differences in the levels of neutralizing antibodies induced by these ND VLP associated pre-fusion F proteins. While not intending to limit the invention to any particular mechanism, data herein (Examples 2-8) show that these differences may be the result of different mutant stabilized pre-F proteins having different conformations or accessibility to monoclonal antibody (mAb) epitopes.

As a first illustration, data herein (Example 3) show that the expression levels and cell surface expression levels vary. This was a surprising finding. In particular, the PR mutants (containing protein SEQ ID NO:06 and 08) and the SC mutants (containing protein SEQ ID NO:10 and 12) were expressed, on cell surfaces, at significantly higher levels (three fold and two fold, respectively) than the DS-Cav1 F mutant (containing protein SEQ ID NO:04) and the post-F mutant (containing protein SEQ ID NO:02).

As a second illustration, data herein (Example 4) show that the reactivity of equal concentrations of the different ND VLPs to representative anti-F protein monoclonal antibodies were surprisingly different, as follows:

mAb D25: PR-DM (containing SEQ ID NO:06): negligible binding
   PR-TM (containing SEQ ID NO:08): 3.3 fold higher than DS-Cav1
   SC-DM (containing SEQ ID NO:10): same as DS-Cav1
   SC-TM (containing SEQ ID NO:12): 5.3 fold higher than DS-Cav1 mAb AM14:

PR-DM (containing SEQ ID NO:06): negligible binding
PR-TM (containing SEQ ID NO:08): 10 fold higher than DS-Cav1
SC-DM (containing SEQ ID NO:10): negligible binding
SC-TM (containing SEQ ID NO:12): 6 fold higher than DS-Cav1

These differences are consistent with different conformations of the alternative pre-fusion F proteins.

As a third illustration, data herein (Example 5) show that the pre-fusion conformation of all five ND VLP associated pre-F proteins were stable in a variety of conditions. Without intending to limit the invention to any particular mechanism, anchoring of the proteins in ND VLP membranes may help to stabilize the pre-fusion conformation. Additionally, without intending to limit the invention to any particular mechanism, the results suggest that the fusion of the ectodomains of these proteins to the NDV TM and CT domains and the inclusion of the foldon sequence at the carboxyl terminus of the F protein ectodomains serves to stabilize the pre-fusion F protein conformation. These are new and surprising findings.

As a fourth illustration, data herein (Example 6) show that the PR-TM ND VLPs (containing protein SEQ ID NO:08) and PR-DM ND VLPs (containing protein SEQ ID NO:06) stimulated neutralizing antibody (NA) levels in sera that were substantially the same as those stimulated by the DS-Cav1 ND VLPs (containing protein SEQ ID NO:04). By contrast, the SC-DM ND VLPs (which contain SC-DM F/F protein sequence (SEQ ID NO:10)) and SC-TM ND VLPs (which contain SC-TM F/F protein sequence (SEQ ID NO:12)) stimulated NA titers two fold higher and three fold higher, respectively, than DS-Cav1 ND VLPs (which contain the DS-CAV1 F/F protein sequence (SEQ ID NO:04)), demonstrating that these versions of pre-fusion F protein more effectively stimulate NA in mice (Examples 6 and 12) and cotton rats (Example 7). Again, this was surprising. Without intending to limit the invention to any particular mechanism, the results further demonstrate that the conformation of these different versions of pre-fusion F proteins is different.

As a fifth illustration, data herein (Example 8) show that immunization of dams with SC-TM ND VLPs (which contain SC-TM F/F protein sequence (SEQ ID NO:12)) at 2 weeks of gestation resulted in a 4 fold increase in protection of the offspring compared to mock immunized controls, and a 4 fold increase in protection compared to SC-DM ND VLPs (which contain SC-DM F/F protein sequence (SEQ ID NO:10)). Immunization of dams with SC-TM ND VLPs (which contain SC-TM F/F protein sequence (SEQ ID NO:12)) at 3 weeks of gestation resulted in a 15 fold increase in pup protection compared to mock vaccinated dams and a 4 fold and 15 fold increase, respectively, in protection compared to SC-DM ND VLP (which contain SC-DM F/F protein sequence (SEQ ID NO:10)) and DS-Cav1 ND VLP (which contain the DS-CAV1 F/F protein sequence (SEQ ID NO:04)) dam immunization at 2 weeks gestation. Thus SC-TM ND VLPs induce in dams higher levels of protection of pups than the other ND VLPs.

Thus, in one embodiment, the invention provides a recombinant chimeric polypeptide comprising SC-TM F/F protein sequence (SEQ ID NO:12, FIG. 19B) and/or SC-DM F/F protein sequence (SEQ ID NO:10, FIG. 18B).

In another embodiment, the invention provides a recombinant Newcastle disease virus-like particle (ND VLP) comprising one or more of the recombinant chimeric polypeptides described herein, and in particular, a ND VLP comprising one or more of SC-TM F/F protein sequence (SEQ ID NO:12, FIG. 19B) and/or SC-DM F/F protein sequence (SEQ ID NO:10, FIG. 18B). In one embodiment, the recombinant ND VLP of further comprises, in operable combination, one or more NDV proteins. In a further embodiment, the one or more NDV proteins comprises one or more of NDV M protein, NDV NP protein, NDV F protein, NDV HN protein, and portions thereof. In a further embodiment, the one or more NDV proteins comprises NDV M protein.

The invention further provides prophylactic and/or therapeutic vaccines that contain one or more of the recombinant ND VLPs described herein and a physiologically acceptable carrier. In one embodiment, the recombinant ND VLP comprises the SC-TM F/F protein sequence (SEQ ID NO:12, FIG. 19B). In another embodiment, the recombinant ND VLP comprises SC-DM F/F protein sequence (SEQ ID NO:10, FIG. 18B).

The invention also provides an expression vector encoding any one or more of the recombinant ND VLPs described herein. In a particular embodiment, the recombinant ND VLP comprises SC-TM F/F protein sequence (SEQ ID NO:12, FIG. 19B) and/or SC-DM F/F protein sequence (SEQ ID NO:10, FIG. 18B).

The invention further provides an expression vector encoding any one or more of the recombinant chimeric polypeptides described herein. In one embodiment, the recombinant chimeric polypeptide comprises SC-TM F/F protein sequence (SEQ ID NO:12, FIG. 19B) and/or SC-DM F/F protein sequence (SEQ ID NO:10, FIG. 18B).

Further provided herein is a method for immunizing a first mammalian subject against respiratory syncytial virus (RSV), comprising administering an immunologically effective amount of one or more vaccines described herein to a mammalian subject in need thereof to produce a treated subject, wherein the administering is under conditions to produce an immune response to the RSV protein or to an immunogenic portion thereof. In one embodiment, the recombinant ND VLP comprises SC-TM F/F protein sequence (SEQ ID NO:12, FIG. 19B) and/or SC-DM F/F protein sequence (SEQ ID NO:10, FIG. 18B).

In a further embodiment, the immune response comprises an increased level of antibody in serum of the treated subject, wherein the antibody specifically binds with one or more of the respiratory syncytial virus (RSV) and the immunogenic portion thereof (Examples 6 and 7). In some embodiments, the increased level of antibody comprises from 1.1 fold (i.e., 10%) to 10 fold (i.e., 1,000%), from 1.5 (i.e., 50%) fold to 10 fold (i.e., 1,000%), from 2 fold (i.e., 200%) to 10 fold (i.e., 1,000%), from 3 fold (i.e., 300%) to 10 fold (i.e., 1,000%), from 2 (i.e., 200%) fold to 5 fold (i.e., 500%), and from 3 fold (i.e., 300%) to 5 fold (i.e., 500%), higher than the level of antibody in serum of a second subject treated with a control vaccine comprising a control recombinant ND VLP that contains DS-Cav1 protein sequence SEQ ID NO:04).

In one embodiment the increased level of antibody comprises a 3 fold (i.e., 300%) increase after vaccination with SC-TM VLPs (which contain SC-TM F/F protein sequence SEQ ID NO:12) compared to vaccination with control DS-Cav1 VLPs (which contain protein sequence SEQ ID NO:04) in mice (Examples 6 and 12) and cotton rats (Example 7)).

In one embodiment the increased level of antibody comprises a 2 fold (i.e., 200%) increase after vaccination with SC-DM VLPs (which contain SC-DM F/F protein sequence SEQ ID NO:10) compared to vaccination with control DS-Cav1 VLPs (which contain protein sequence SEQ ID NO:04) in mice (Examples 6 and 12) and cotton rats (Example 7)).

Data herein (Example 6) show that the PR-TM ND VLPs (which contain PR-TM F/F protein sequence SEQ ID NO:08) and PR-DM ND VLPs (which contain PR-DM F/F protein sequence SEQ ID NO:06) stimulated neutralizing antibody (NA) levels in sera that were substantially the same as those stimulated by the DS-Cav1 ND VLPs (which contain protein sequence SEQ ID NO:04). By contrast, the SC-DM ND VLPs (which contain SC-DM F/F protein sequence SEQ ID NO:10) and SC-TM ND VLPs (which contain SC-TM F/F protein sequence SEQ ID NO:12) stimulated NA titers two fold higher and three fold higher, respectively, than DS-Cav1 ND VLPs (which contain protein sequence SEQ ID NO:04) in mice (Examples 6 and 12) and cotton rats (Example 7).

In one embodiment, the mammalian subject is female. In another embodiment, immunizing the female subject is before birth of an offspring of the female subject. In a particular embodiment, immunizing is during gestation by the female subject (e.g., to protect her offspring against RSV infection (Example 8).

The invention further provides a method for immunizing a mammalian subject in need thereof against respiratory syncytial virus (RSV), comprising administering an immunologically effective amount of one or more vaccines described herein to the mother a first mammalian subject prior to birth of the mammalian subject to produce a treated mother, wherein the administering step is under conditions to produce an immune response to one or more of the respiratory syncytial virus (RSV) proteins and an immunogenic portion thereof in the treated mother. In one embodiment, the administering step is before and/or during gestation of the mammalian subject.

In a particular embodiment, the immune response comprises an increased level of antibody in serum of the treated mother, wherein the antibody specifically binds with one or more of the respiratory syncytial virus (RSV) protein and the immunogenic portion thereof.

Data herein (Example 7) show that SC-DM ND VLPs (which contain SC-DM F/F protein sequence SEQ ID NO:10) and SC-TM ND VLPs (which contain SC-TM F/F protein sequence SEQ ID NO:12) stimulated higher NA titers in pregnant cotton rats than DS-Cav1 ND VLPs (which contain DS-Cav1 protein sequence SEQ ID NO:04) (Example 7).

Figure 8:
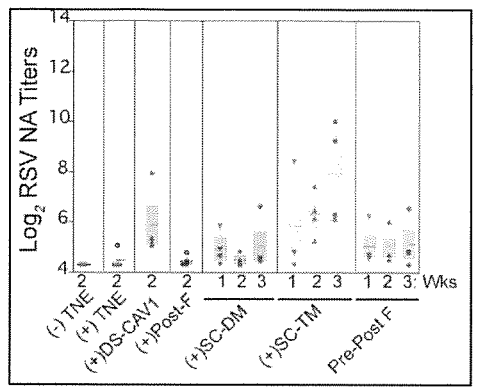
FIG. 8: Neutralizing Antibody Titers in Pups. Neutralizing titers in sera from pups obtained 4 weeks after birth was determined in a plaque reduction assay. Weeks refers to time of gestation at which the dams were immunized. +, RSV primed. Pre-post is a group of pups from dams immunized with a mix of post-F and DS-Cav1 VLPs.

Data herein in FIG. 8 show that that immunization of dams with SC-TM VLPs (which contain SC-TM F/F protein sequence SEQ ID NO:12) resulted in the highest levels of neutralizing antibodies in the pups, levels much higher than in pups delivered from dams immunized with DS-Cav1 VLPs (which contains DS-Cav1 protein SEQ ID NO:04) or SC-DM VLPs (which contain SC-DM F/F protein sequence SEQ ID NO:10).

Figure 9:
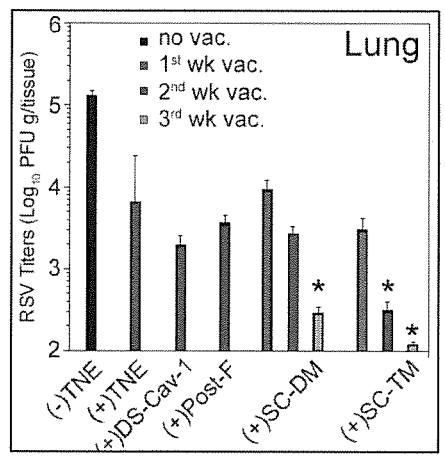
FIG. 9: Protection of Pups from RSV. Shown are lung titers of RSV in pups after challenge with RSV (at 4 weeks after birth). Wk=weeks of gestation when dams were immunized with VLPs indicated at the bottom.

In one embodiment, the immune response comprises an increased level of protection of the mammalian subject against RSV infection (Example 8, FIG. 9). The "level of protection" of a subject against RSV infection may be determined by measuring the viral titer in the subject (FIG. 9). Thus, an "increased level of protection" against RSV means a reduction in the level of RSV titers in the subject. In some embodiments, the increased level of protection of the mammalian subject against RSV infection comprises from 2 to 30 fold, from 2 to 20 fold, from 2 to 15 fold, from 2 to 10 fold, from 2 to 5 fold, from 2 to 4 fold, from 2 to 3 fold, from 3 to 20 fold, from 3 to 15 fold, from 4 to 20 fold, and from 4 to 15 fold, increase in the level of protection after administering to a mother of a second mammalian subject a control vaccine comprising a control recombinant ND VLP that contains DS-Cav1 protein sequence SEQ ID NO:04).

In a further embodiment, the immune response comprises an increased level of antibody in serum of the mammalian subject, wherein the antibody specifically binds with one or more of the respiratory syncytial virus (RSV) protein and the immunogenic portion thereof. Data herein (FIG. 9) show that immunization of dams with SC-TM ND VLPs (which contain SC-TM F/F protein sequence SEQ ID NO:12) at 2 weeks of gestation resulted in a 4 fold increase in protection of the offspring against RSV infection compared to mock immunized controls, and a 4 fold increase in protection compared to SC-DM ND VLPs (which contain SC-DM F/F protein sequence SEQ ID NO:10). Immunization of dams with SC-TM ND VLPs (which contain SC-TM F/F protein sequence SEQ ID NO:12) at 3 weeks of gestation resulted in a 15 fold increase in pup protection compared to mock vaccinated dams and a 4 fold and 15 fold increase, respectively, in protection compared to SC-DM ND VLP (which contain SC-DM F/F protein sequence SEQ ID NO:10) and DS-Cav1 ND VLP (which contain protein sequence SEQ ID NO:04) dam immunization at 2 weeks gestation. Thus SC-TM ND VLPs induce in dams higher levels of protection of pups than the other ND VLPs.

In one embodiment, the method further comprises one or more of a) detecting the immune response to RSV and/or to an immunogenic portion thereof, and b) detecting a reduction in one or more symptoms of RSV infection in the treated subject. In one embodiment, administering the vaccine is prophylactic before manifestation of one or more symptoms of RSV infection. In one embodiment, administering the vaccine is therapeutic after manifestation of one or more symptoms of RSV infection. In one embodiment, the vaccine prevents RSV infection.

B) Methods for Production of VLPs

A significant step toward clinical trials of the VLPs will be development of protocols for large-scale production of VLP vaccine candidates by cost-effective, robust manufacturing practices. Data herein (Example 9) demonstrates a method for the use of baculovirus (BV) vectors to express the exemplary VLP proteins (SC-TM F/F, NDV HN/RSV G (referred to as H/G), NDV NP, and NDV M) (FIG. 21A-D) in FDA approved cell lines for vaccine.

BVs do not replicate in mammalian cells. However, BV can infect mammalian cell lines, and, if a foreign gene is inserted into the BV genome downstream (i.e., at the C-terminal end) of a mammalian promoter, the gene will be expressed upon BV infection of mammalian cells. Thus, BV encoding selected genes can be propagated inexpensively in SF9 insect cells, purified, titered, and then used to transduce cell lines of choice for expression of the inserted genes. Levels of expression can be controlled by multiplicity of infection (moi).

i) Sodium Butyrate

The invention provides a transgenic baculovirus expression vector that comprises baculovirus genome (exemplified by GenBank Accession numbers NC001623, NC004323, NC008349)), the genome comprising a first nucleotide sequence encoding a virus-like particle (VLP), the first nucleotide sequence operably linked to a mammalian promoter sequence. In one embodiment, the VLP comprises an immunogenic polypeptide sequence. In one embodiment, the mammalian promoter sequence comprises a hybrid beta globin-CMV promoter (FIG. 20A-B).

Figure 12:
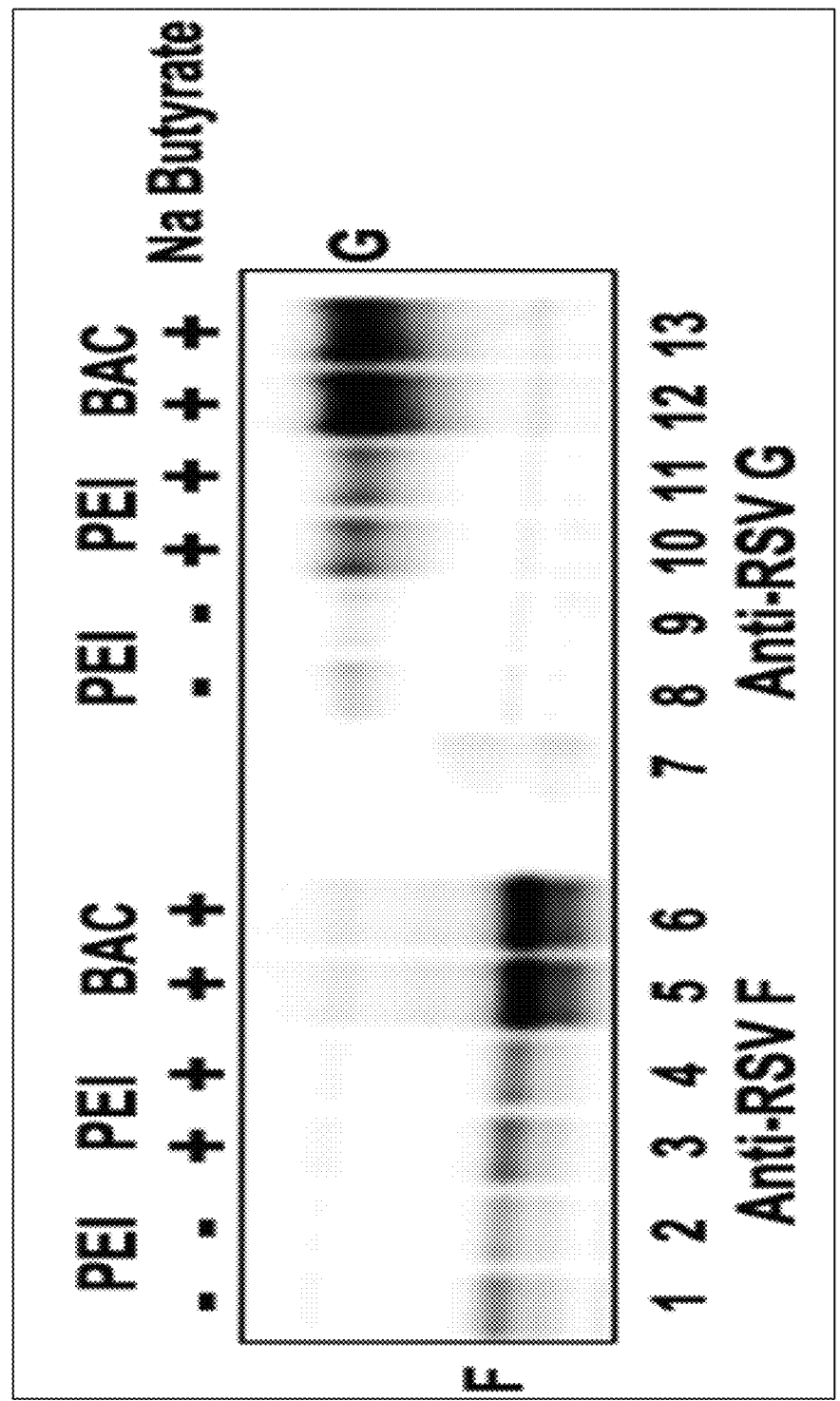
FIG. 12. Effect of Na-butyrate on VLP yield in 293F cells. Cells were transfected with cDNAs (using PEI) (lanes 1-4, 8-11) or transduced with BV (BAC, moi=10) (lanes 5,6,12, 13) and incubated in the absence or presence of Na-butyrate (50 mM). Proteins in purified VLPs were detected by Western blot with anti-F (lanes 1-7) or anti-G antibodies (lanes 7-13). Duplicate lanes are VLPs released 3 and 6 days after transfection or transduction. Lane 7, marker F protein.

The invention further provides a method for producing recombinant virus-like particles (VLPs) comprising infecting one or more of a mammalian cell and avian cell, in the presence of sodium butyrate, with a transgenic baculovirus expression vector to produce the recombinant VLPs, wherein the baculovirus expression vector comprises a baculovirus genome (exemplified by GenBank Accession numbers NC001623, NC004323, NC008349), that contains a first nucleotide sequence encoding the VLPs, and wherein the first nucleotide sequence is operably linked to a mammalian promoter sequence. In one embodiment, the infecting step produces the VLPs at a yield that is higher than in the absence of the sodium butyrate (FIG. 12). In one embodiment, the VLP yield comprises from 1 to 10 fold, 2 to 10 fold, 3 to 10 fold, 4 to 10 fold, 5 to 10 fold, and 6 to 10 fold, higher in the presence of sodium butyrate than in the absence of sodium butyrate. In particular, data herein (FIG. 12) demonstrate that inclusion of Na-butyrate during VLP production increased the VLP yield from chimeric BV transduced mammalian cells by 6 fold.

Figure 10:
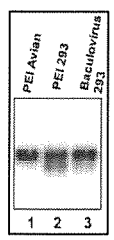
FIG. 10: F proteins in VLPs released from different cell lines. Western blot of F proteins in VLPs released from avian or 293 cells. PEI: transient transfection; baculovirus: BV transduced cells.
Figure 11:
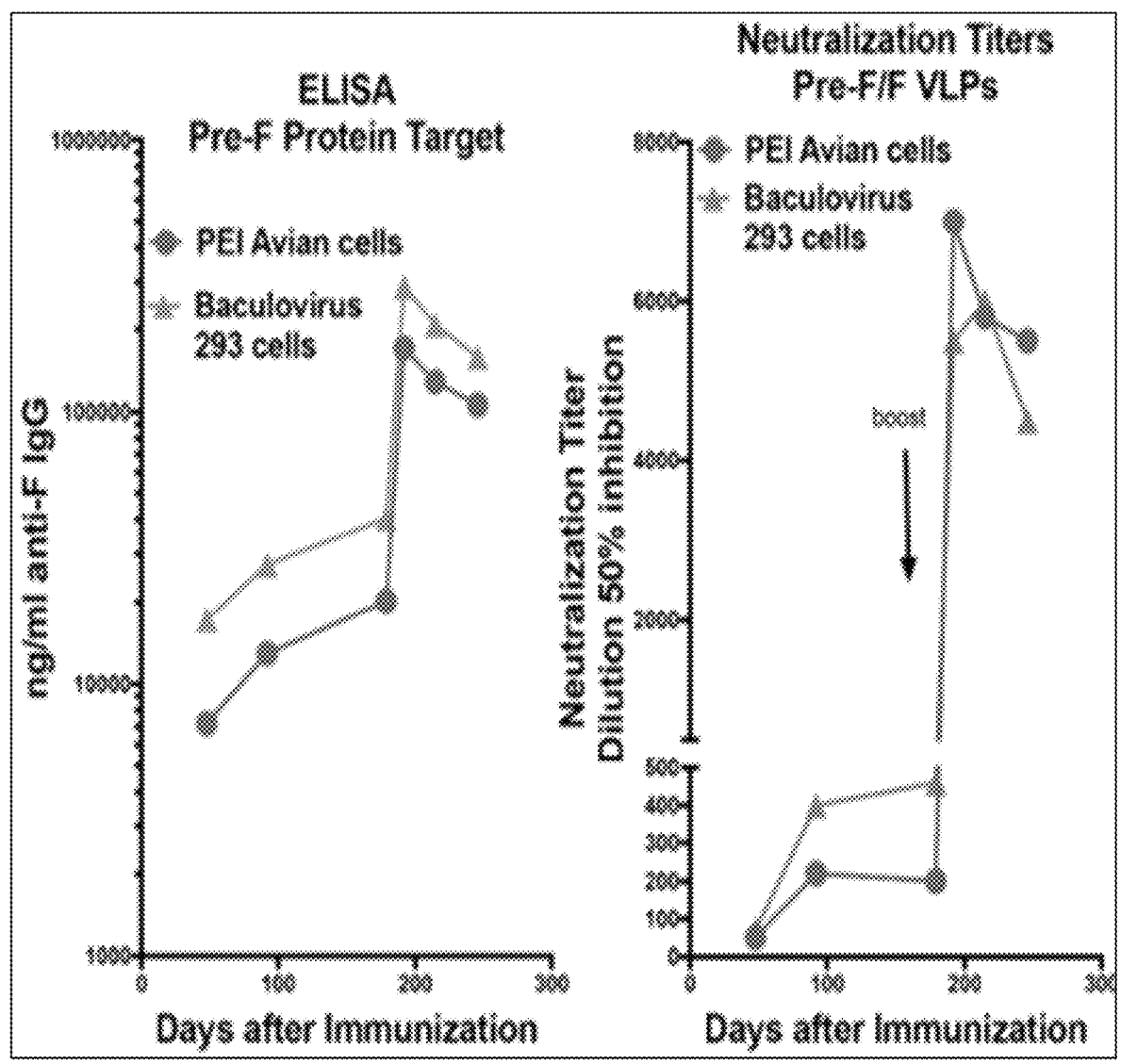
FIG. 11: Immune responses to VLPs from different cell types. VLPs from avian cells or BV infected 293 cells were used to immunize mice in a prime/boost protocol. Left panel total anti-F IgG in pooled sera with time after prime (ELISA; soluble pre-F target). Right panel, NA titers (serum dilution that reduces virus titer 50%).

In one embodiment, method further comprises, prior to infecting in the presence of sodium butyrate, infecting an insect cell with the BV vector to produce a BV stock. In one embodiment, the VLPs are produced by infecting a mammalian or avian cells with BV. The VLPs released from the cell are immunogenic (FIG. 11). In a particular embodiment, infecting the mammalian cell produces the VLPs at substantially the same efficiency as transiently transfecting one or more of avian cells and mammalian cells (FIG. 10).

In a further embodiment, the method comprises (a) prior to the infecting, the step of concentrating a sample for the transgenic baculovirus expression vectors to produce a concentrated sample, and (b) using the concentrated sample in the infecting step in mammalian or avian cells.

The cell infected and/or transfected and/or transduced with any one or more of the compositions and/or one or more of the methods of the invention can be any mammalian cell and/or avian cell that can be infected by baculovirus.

Exemplary mammalian cells include e293F cells (also known as Expi293F cells) which is a cell line derivative of HEK 293 that can be grown in suspension culture. Other illustrative mammalian cell lines include MDCK (Madin Darby canine kidney cells), Vero (African Green Monkey epithelial cells), and CHO (Chinese Hamster Ovary Cells), and previously described cells in Boyce et al. 1996. Baculovirus-mediated gene transfer into mammalian cells. Proc Natl Acad Sci USA 93:2348-2352; Lee & Yu, Expression in mammalian cells using BacMam viruses. in Expression Systems: (M. R. Dyson and Y. Durocher, eds) Chapter 15, page 261. © Scion Publishing Limited, 2007. Methods Express; Condreay et al. 1999. Transient and stable gene expression in mammalian cells transduced with a recombinant baculovirus vector. Proc Natl Acad Sci USA 96:127-132; Fornwald et al. 2006. Gene expession in mammalian cells using BacMam modified BV system. Methods in Molecular Biology 338: 95; and Kost et al., Baculovirus as versatile vectors for protein expression in insect and mammalian cells, Nat Biotechnol, 23 (2005), pp. 567-575.

Exemplary avian cells include those described herein (Example 9); chicken primary cells (Ping et al., Baculovirus-mediated gene expression in chicken primary cells, Avian Dis, 50 (2006), pp. 59-63); and chicken embryo fibroblast cells (Jingping et al., Construction of Recombinant Baculoviruses Expressing Infectious Bursal Disease Virus Main Protective Antigen and Their Immune Effects on Chickens, PLoS One. 2015; 10(7): e0132993).

ii) Multiplicity of Infection

The invention provides a method for producing recombinant virus-like particles (VLPs) comprising a) providing a first sample that contains transgenic baculovirus expression vectors, wherein the baculovirus expression vectors comprises a baculovirus genome that contains a first nucleotide sequence encoding the VLPs, and wherein the first nucleotide sequence is operably linked to a mammalian promoter sequence, b) concentrating the first sample for the transgenic baculovirus expression vectors to produce an "concentrated" sample (i.e., a sample that contains a higher multiplicity of infection than the first sample), and c) infecting one or more of a mammalian cell or an avian cell with the concentrated sample to produce the recombinant VLPs.

Figure 13:
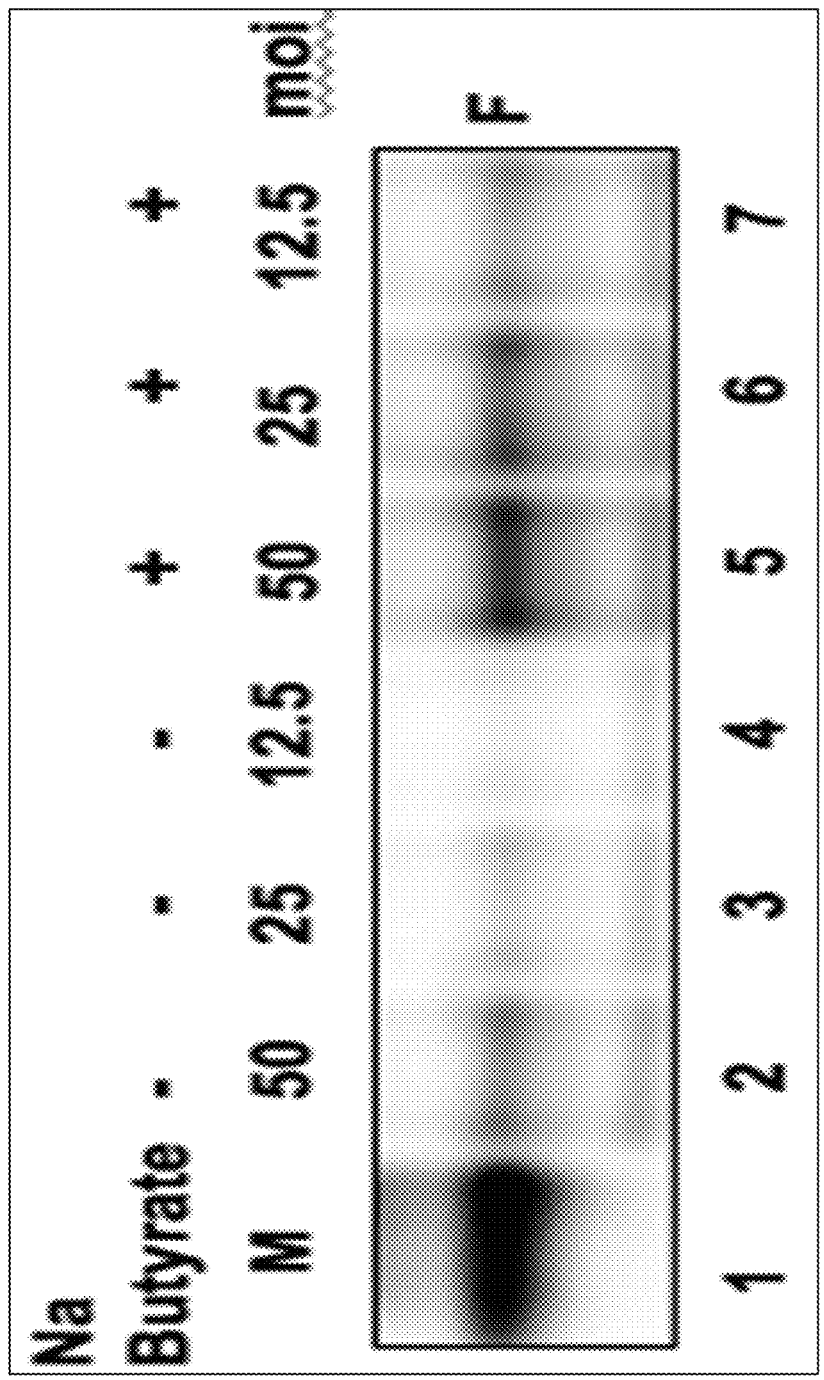
FIG. 13. Effect of BV moi on VLP release from 293F cells. 293F cells transduced with different moi of each of the four BV in the absence (lanes 2-4) or presence of Na butyrate (5 mM)(lanes 5-7). Shown is F in Western blots. M, marker F.

In one embodiment, the infecting step produces the VLPs at a yield that is higher than in the absence of the concentrating step (FIG. 13). In one embodiment, the VLP yield comprises from 1 to 10 fold, 1 to 9 fold, 1 to 8 fold, 1 to 7 fold, 1 to 6 fold, 1 to 5 fold, 1 to 4 fold, 1 to 3 fold, 1 to 2 fold, 1 to 1.5 fold, 1 to 1.6 fold, 1 to 1.7 fold, 1 to 1.8 fold, 1 to 1.9 fold, 1 to 2.0 fold, 1 to 2.1 fold, 1 to 2.2 fold, 1 to 2.3 fold, 1 to 2.4 fold, 1 to 2.5 fold, 1 to 2.6 fold, 1 to 2.7 fold, 1 to 2.8 fold, and 1 to 2.9 fold, higher in the presence of the concentrating step than in the absence of the concentrating step. In particular, data herein (FIG. 13) demonstrate that inclusion of the concentrating step during VLP increased the VLP yield from chimeric BV transduced mammalian cells by 2.2 fold.

In a further embodiment, the method further comprises, prior to the concentrating step, infecting an insect cell with the vector to produce the recombinant BV stocks. In a particular embodiment, the VLPs produced by infecting the mammalian or avian cells are immunogenic (FIG. 11). In another embodiment, infecting of the mammalian or avian cells produces the VLPs at substantially the same efficiency as transiently transfecting one or more of avian cells or mammalian cells (FIG. 10). In a further embodiment, infecting is in the presence of sodium butyrate.

The invention further provides a recombinant virus-like particle (VLP) produced by any one or more of the methods described herein.

EXPERIMENTAL

The following examples serve to illustrate certain preferred embodiments and aspects of the present invention and are not to be construed as limiting the scope thereof.

Example 1

Materials and Methods

Cells, Plasmids, Viruses

ELL-O, Vero cells, and Hep2 cells were obtained from the American Type Culture Collection and grown in DMEM (Invitrogen) supplemented with penicillin, streptomycin (Invitrogen), and 5% (Vero cells) or 10% fetal bovine serum (ELL-O, Hep2 cells) (Invitrogen). Expi293F cells, obtained from ThermoFisher/Invitrogen, were grown in Expi293 media (ThermoFisher/Gibco/Invitrogen). RSV, A2 strain, was obtained from Dr. Robert Finberg. Virus stocks were prepared from infected Hep2 cells as previously described [20].

VLPs containing the RSV F and G protein ectodomains (from RSV stain A2) are assembled, as chimera proteins, with the Newcastle disease virus (NDV) core proteins NP and M as previously described [20, 24]. The construction, expression, and incorporation of the chimera protein NDVHN/RSVG (H/G) into VLPs have been previously described [21]. The construction, expression, and incorporation into VLPs of the stabilized pre-fusion DS-Cav1 F/F protein to generate VLP-H/G+DS-Cav1 F/F (abbreviated DS-Cav1 VLPs), and the stabilized post-fusion F protein to create VLP-H/G+post-F/F (abbreviated post-F VLPs) have been previously described [24]. Chimera proteins containing alternative versions of pre-fusion F protein were constructed by introducing mutations into the wild type F/F chimera. PR-DM F/F and PR-TM F/F contained mutations N67I, S215P, or N67I, S215P, and D486N, respectively. SC-DM F/F and SC-TM F/F both had deletions of p27 sequence including the two cleavage sites combined with insertion of a linker sequence GSGSGRS as diagramed in FIG. 1. In addition, SC-DM F/F and SC-TM F/F had two (N67I, S215P) or three (N67I, S215P, D486N) amino acid substitutions, respectively.

The constructions of genes encoding the soluble pre-F protein and the soluble post-F protein, have been previously described [24, 26].

Antibodies

RSV F monoclonal antibody clone 131-2A (Millipore MAB8599) was used in RSV plaque assays. Murine monoclonal antibodies mAb1112 and mAb1243 (generous gifts of Dr. J. Beeler), and human mAb D25, mAb AM14, and mAb motavizumab, (generous gifts of Dr. J. McLellan) were used to verify F protein conformation in ELISA analysis of VLPs and soluble F proteins, and for antibody blocking experiments. Palivizumab used for antibody blocking experiments was the generous gift of Dr. Jorge Blanco. Anti-RSV F protein HR2 antibody and anti-NDV F-tail antibody used for Western Blots are polyclonal antibodies specific to the HR2 domain of the RSV F protein or the cytoplasmic tail of NDV F protein [20]. Anti-RSV G protein antibody is a polyclonal antibody raised against a peptide containing G protein amino acids 180-198 (ThermoFisher). Secondary antibodies against goat, mouse, and rabbit IgG were purchased from Sigma. Secondary antibody against human IgG was purchased from Southern Biotech.

VLP preparation, purification, and characterization The conformation of F protein in the VLP preparations was verified by reactivity to mAbs. The characterization of purified preparations of Pre-F/F VLPs and Post-F/F VLPs has been previously published [24, 26]. For preparations of VLPs to be used as immunogens (abbreviated as DS-Cav1 VLPs, post-F VLPs, PR-DM VLPs, PR-TM VLPs, SC-DM VLPs, SC-TM VLPs), ELL-0 cells growing in T-150 flasks were transfected with cDNAs encoding the NDV M protein, the NDV NP, the chimera protein H/G, and one of the five Pre-F/F proteins or the Post-F/F protein as previously described [20]. At 24 hours post-transfection, heparin (Sigma) was added to the cells at a final concentration of 10 □g/ml to inhibit rebinding of released VLPs to cells. At 72, 96, and 120 hours post-transfection, cell supernatants were collected and VLPs purified by sequential pelleting and sucrose gradient fractionation as previously described [30]. Briefly, cell debris from the supernatant was removed by centrifugation at 5000 rpm (Sorvall GSA SLA-1500 rotor), VLPs in the supernatant pelleted by centrifugation in a Type 19 Rotor (Beckman) at 18,000 rpm for 12 hours. The resulting pellet was resuspended in TNE buffer (25 mM Tris-HCl, pH 7.4, 150 mM NaCl, and 5 mM EDTA), dounce homogenized, and layered on top of a discontinuous sucrose gradient (2 ml 65% sucrose and 4 ml 20% sucrose). The gradients were centrifuged in an SW 28 rotor (Beckman) at 24,000 rpm for 6 hours and the fluffy layer at the 20-65% sucrose interface, containing the VLPs, was collected, mixed with two volumes of 80% sucrose, placed in top of a 1 ml layer of 80% sucrose in a SW41 Beckman centrifuge tube, and then over layered with 3.5 ml of 50% sucrose and 2 ml of 10% sucrose. The gradients were centrifuged to equilibrium for 18 hours at 38,000 rpm. The VLPs, all of which floated up into the sucrose to the same density, were collected and concentrated by centrifugation in an SW50.1 rotor for 16 hours at 38,000 rpm. All sucrose solutions were w/v and dissolved in TNE buffer and all centrifugations were done at 4° C.

The characterization of purified preparations of all VLPs were as previously described for Pre-F VLPs and Post-F VLPs [24, 26]. The conformation of F protein in the VLP preparations was verified by reactivity to mAbs mAbs (as in FIG. 3A-F and previously described [24, 26]). Protein concentrations of VLP associated F proteins were calculated from a standard curve generated with a parallel western blot of purified soluble F protein of known concentration.

Preparation of Soluble F Proteins

Expi293F cells were transfected with cDNAs encoding the soluble DS-Cav1 pre-F protein, the soluble SC-TM pre-F protein, and the soluble post-F protein. At six days post transfection, total cell supernatants were collected and cell debris removed by centrifugation. Soluble polypeptides were then purified on columns using the His tag and then the strep tag as previously described [24, 26]. Our soluble DS-Cav1 pre-F protein and soluble SC-TM pre-F protein efficiently bind to pre-fusion specific mAbs AM14 and D25. The soluble post-F does not bind AM14 or D25 but does bind motavizumab, a site II antibody. The validation of these soluble proteins is described in Blanco, et al[26].

Detection of Cell Surface Protein by Surface Biotinylation

ELL-0 monolayers were grown in 35 mm plates and transfected with cDNAs encoding the F/F proteins or F/F and H/G proteins. After 48 hours, the monolayers were washed three times with PBS-CM (PBS with 0.1 mM CaCl2 and 1 mM MgCl2). PBS-CM containing 0.5 mg/ml sulfo-NHS-SS-biotin (Pierce) was added and cells were incubated for 40 minutes at 4° C. Unbound biotin was absorbed with 2 ml DMEM containing fetal calf serum (10%) and cells were washed three times with PBS and lysed with RSB lysis buffer (0.01M Tris-HCl [pH 7.4], 0.01M NaCl, 1.5 mM MgCl2) containing 1% Triton X-100, 0.5% sodium deoxycholate, 2.5 mg of N-ethyl maleimide per ml, and 0.2 mg of DNase per ml. Lysates were incubated for 1 h at room temperature or overnight at 4 C with neutravidin-agarose (Pierce), containing 0.3% SDS, that had been washed with PBS containing 0.5% tween-20, and 5 mg/ml BSA and then with PBS containing 0.5% Tween-20 and 1 mg/ml BSA. Precipitates containing biotinylated proteins were recovered by centrifugation, washed three times with PBS containing 0.5% Tween-20 and 0.4% SDS, resuspended in gel sample buffer (125 mM Tris-HCl, pH 6.8, 2% SDS and 10% glycerol) with 0.7M β-mercaptoethanol and resolved by polyacrylamide gel electrophoresis. F proteins in the precipitate were detected by Western analysis using anti-NDV F tail antibody.

Measures of Relative Binding of mAb to Purified VLPs.

VLPs containing equivalent amounts of F protein (determined by Western blots) were added to microtiter wells and incubated 2-4 hours at room temperature. Different dilutions of different mAb were added to the wells, incubated for 2 hrs, removed, and the wells were washed with PBS. The mAbs were then removed, the plate washed in PBS, and incubated with goat anti-human IgG coupled to HRP for 2 hours at room temperature. Bound HRP was detected using TMB (3,3'5,5'-tetramethylbenzidin, ThermoFisher34028)

and the reaction was stopped with 2N sulfuric acid. Color was read in SpectraMax Plus Plate Reader (Molecular Devices) using SoftMax Pro software. Results are expressed as optical density (OD).

Determination of Stability of Pre-Fusion F Conformation

For determination of the stability of pre-fusion F conformation in VLPs, VLPs with equivalent amounts of F protein were incubated at different temperatures, different pHs, or different salt concentrations for 1 hour. The VLPs were then bound to microtiter wells overnight at 4° C. The wells were incubated with PBS-2% BSA, then incubated with mAb D25 for 1 hour and the binding of mAb was detected using anti-human IgG coupled to HRP. Bound HRP was detected as described above.

Determination of Total Anti-F Protein IgG in Sera.

For determination of anti-pre-F protein or post-F protein IgG antibody levels, wells of microtiter plates (ThermoFisher/Costar) were coated with either purified soluble DS-Cav1 F protein or soluble post-fusion F protein (30 ng/well) and incubated overnight at 4° C., then blocked with 2% BSA for 16 hours. Different dilutions of sera, in PBS-2% BSA and 0.05% Tween, were added to each well and incubated for 2 hours at room temperature. Wells were then washed with PBS, incubated with sheep anti-mouse antibody coupled to HRP (Sigma A5906), and incubated for 1.5 hours at room temperature. Bound HRP was detected using TMB (3,3'5,5'-tetramethylbenzidin, ThermoFisher34028) and the reaction was stopped with 2N sulfuric acid. Color was read in SpectraMax Plus Plate Reader (Molecular Devices) using SoftMax Pro software. Amounts of anti-pre-F or anti-post-F IgG (ng/ml) in each dilution were calculated using a standard curve generated in parallel using defined amounts of purified murine IgG.

RSV Plaque Assays, Antibody Neutralization, Antibody Blocking

RSV was grown in Hep2 cells, and RSV plaque assays were accomplished on Vero cells as previously described [24, 26]. Antibody neutralization assays in a plaque reduction assay have been previously described [24]. Neutralization titer was defined as the reciprocal of the dilution of serum that reduced virus titer by 50%.

To measure ability of polyclonal sera to block binding of mAbs, different dilutions of sera were diluted in PBS-1% BSA, and then incubated for 1 hour at room temperature in wells of Ni coated microtiter plates (Pierce/ThermoFisher) containing pre-bound 50 ng soluble DS-Cav1 pre-F protein or soluble SC-TM pre-F protein. Ni coated plates were used in order to bind the soluble pre-F proteins via the histidine tag at the carboxyl terminus of the protein and thus orienting the protein in the well with the apex of the molecule projecting upwards as in virus particles. After removal of the serum, the wells were incubated with 200 ng/ml of purified mAb diluted in PBS-1% BSA for 10 minutes at room temperature. The mAb was then removed, the plate washed in PBS, and incubated with goat anti-human IgG coupled to HRP. After incubation for 1 hour at room temperature, the bound HRP was detected as in ELISA assays. The total anti-pre-F IgG in the different serum dilutions used for mAb blocking, was determined using a standard curve of purified murine IgG (Southern Biotech) in order to measure the ng of serum anti-pre-F antibody that blocked binding of the mAb.

Animals, Animal Immunization, and RSV Challenge

Mice, 4-week-old BALB/c, from Taconic laboratories, were housed (groups of 5) under pathogen-free conditions in micro isolator cages at the University of Massachusetts Medical Center animal quarters. Protocols requiring open cages were accomplished in biosafety cabinets. BALB/c mice, in groups of 5 animals, were immunized by intramuscular (IM) inoculation of VLPs containing 7 □g F protein in 0.05 ml of THE (50 mM Tris-HCl, pH 7.4, 150 mM NaCl, 5 mM EDTA) containing 10% sucrose. Boosts contained 3 g of VLP F protein. For infections with RSV, the animals were lightly anesthetized with isoflurane and then infected by intranasal (IN) inoculation of 50 ul of virus ($1\times10^6$ pfu). All animal procedures and infections were performed in accordance with the University of Massachusetts Medical School IACUC approved protocols; approved Sep. 13, 2017 to Sep. 12, 2020.

Statistical Analysis

Statistical analyses (student T test) of data were accomplished using Graph Pad Prism 7 software.

Example 2

Alternative Pre-Fusion F Proteins

To prepare ND VLPs containing alternative pre-fusion F proteins, we constructed four different versions of mutation stabilized pre-fusion F proteins, described by Krarup, et al (3). Two of these mutants contained the wild type cleavage sites and either two (N67I, S215 P) or three point (N67I, S215P, D486N) mutations to generate processed F protein PR-DM and PR-TM, respectively (FIGS. 1, 16A-B, and 17A-B). The other two mutants had the cleavage site sequences and the intervening p27 sequence replaced with a seven-amino acid GS rich linker sequence (FIGS. 1, 18A-B and 19A-B). In addition, two (N67I, S215P) or three (N67I, S215P, D486N) amino acid changes were introduced into the ectodomain sequences to generate SC-DM and SC-TM F proteins, respectively (FIGS. 1, 18A-B and 19A-B). For assembly into ND VLPs, the sequences encoding the ectodomains of these F proteins were fused to the sequences encoding the transmembrane (TM) and cytoplasmic (CT) domains of the NDV F proteins to generate RSVF/NDVF chimera proteins, PR-DM F/F, PR-TM F/F, SC-DM F/F, and SC-TM F/F, (FIGS. 1 and 16A-B-19A-B).

Example 3

Expression of Alternative Pre-Fusion F Proteins

The expression levels and cell surface expression levels vary with the version of pre-F protein FIG. 2A-B). The PR mutants and the SC mutants were expressed, in cell extracts and on cell surfaces, at significantly higher levels than the DS-Cav1 F mutant and the post-F mutant. This finding suggested that the synthesis, folding, or intracellular transport of the PR and SC mutant proteins are more efficient than that of DS-Cav1 F protein. This surprising property greatly facilitated the preparation of PR and SC VLPs, requiring many fewer cells for their generation compared to DS-Cav1 VLPs.

Purified VLPs containing the F proteins were prepared and purified as previously described. All VLPs contained the same H/G chimera and one of the mutant F/F chimera proteins.

Purified VLPs containing the F proteins were prepared and purified as previously described [30]. All VLPs contained the same H/G chimera and one of the F/F chimera proteins. VLPs containing PR-DM F/F, PR-TM F/F, SC-DM F/F, or SC-TM F/F will be referred to as PR-DM, PR-TM, SC-DM, or SC-TM VLPs. The protein content of purified VLPs was initially assessed by Western blots shown in FIG. 27A-C and stocks adjusted for equivalent F protein content. FIG. 3A-F, panels FIGS. 3C, D, and E, show the protein content of these adjusted VLP stocks. Quantitation of the content of the F/Fs, H/G, and NP relative to that in DS-Cav1 VLPs is shown in Table 2.

TABLE 2

Relative concentrations of VLP proteins in different VLP stocks
Table 1: Quantification of Proteins in VLPs

| VLP | F/F protein anti-NDV F tail | F/F protein anti-RSV HR2 | H/G Protein anti-RSV | NP anti-NDV |
|---|---|---|---|---|
| DS-Cav1 | 1.0 | 1.0 | 1.0 | 1.0 |
| PR-DM | 1.11 | 1.0 | 0.6 | 0.44 |
| PR-TM | 1.30 | 1.10 | 0.71 | 0.43 |
| SC-DM | 1.21 | 1.13 | 0.77 | 0.60 |
| SC-TM | 0.92 | 0.83 | 0.5 | 0.45 |
| Post-F | 1.02 | 0.52 | 0.58 | 0.42 |

Legend to Table 2: Concentrations of VLP proteins. The concentration of F/F, H/G, and NP proteins in VLPs adjusted for equivalent F protein content are shown relative to the concentration in DS-Cav1 VLPs. Values for each protein were obtained by determining density of the signal on Western Blots (FIG. 2A-B) (exposed in the linear range of detection), using Photoshop. The values for DS-Cav1 VLP proteins were set at 1.0 and values for proteins in the other VLPs are shown relative to DS-Cav1 values.

The DS-Cav1 VLPs consistently contained higher amounts of NP and H/G relative to the other VLPs suggesting some differences in the efficiency of incorporation of the DS-Cav1 F into VLPs compared to the other VLPs. This difference may relate to the lower efficiency of expression of the DS-Cav1 F protein shown in panel FIGS. 2A and B. F protein in Post-F/F VLPs is consistently not detected as well with anti-RSV HR2 antibody compared to anti-NDV F tail antibody.

Example 4

Binding of Monoclonal Antibodies to VLPs

To verify the pre-fusion conformation of the F proteins in VLPs, the binding of representative anti-F protein monoclonal antibodies to the VLPs was measured by ELISA (FIG. 4A-E). For this experiment, equivalent micrograms of VLPs associated F proteins were bound to microtiter plates and then incubated with increasing dilutions of each mAb. FIG. 4A-E, panels FIGS. 4A, B, and C show the relative binding of monoclonal antibodies specific to sites common to both pre-fusion and post-fusion forms of the F protein, motvizumab (site II), mAb 1112 (site 1), and mAb 1243 (site IV). The site II and I mAb binding to all VLPs was similar although binding to DS-Cav1 VLPs was reproducibly slightly increased over the other VLPs. Interestingly, the antibody to site IV showed more variation in binding suggesting some differences in the conformation of the different pre-fusion F proteins. Two pre-fusion F specific mAbs, D25 (2)(site 0) and AM14, a trimer specific, pre-fusion specific antibody ((6)), were used to verify that the F proteins retained their reported pre-fusion conformation after purification of the VLPs (panels FIGS. 4D and E). All VLPs, except post-F VLPs, bound both AM14 and D25 indicating that the F proteins in these VLPs retained some F protein in the pre-fusion conformation. However, D25 antibody binding showed surprising differences. While DS-Cav1 VLPs and SC-DM VLPs bound mAb D25 similarly (panel FIG. 4D), PR-TM and SC-TM VLPs bound this antibody at higher levels and PR-DM VLPs bound this antibody at much lower levels than DS-Cav1 VLPs. The binding of AM14 also showed interesting differences (panel FIG. 4E). The PR-TM and SC-TM VLPs bound this antibody at much higher levels than the DS-Cav1 VLPs. However, the PR-DM and the SC-DM VLPs bound this antibody poorly. That SC-DM very poorly bound mAb AM14 but bound D25 at levels similar to DS-Cav1 VLPs suggests that the conformation of this F protein may be different from DS-Cav1. The poor binding of both mAbs D25 or AM14 to PR-DM VLPs suggests that the majority of this F protein may not be in a pre-fusion conformation.

Thus, the differences in mAb binding to the different VLPs suggest that the VLP associated SC and PR pre-fusion F proteins have conformational differences from DS-Cav1. This was a surprising finding because it would have been assumed that all stabilized pre-fusion F proteins would be substantially the same. However, without intending to limit the invention to any particular mechanism, the results suggest major conformational differences between different versions of the pre-fusion F proteins that contain different mutations.

Example 5

Stability of the Pre-Fusion F Proteins in the VLPs

Because of reports of the instability of soluble DS-Cav-1 pre-fusion F protein (3-5), we characterized the stability of the pre-fusion conformation of all these chimera proteins in VLPs under different pH conditions, temperatures, and salt concentrations. The degree of retention of the pre-fusion conformation was determined as the percent of mAb D25 (site 0) binding relative to binding to untreated controls. FIG. 5 shows that none of the VLPs lost statistically significant reactivity to mAb D25 after incubation in different conditions. Indeed, some treatments somewhat increased the mAb D25 binding. VLPs were also subjected to three freeze-thaw cycles and none demonstrated a drop in mAb D25 binding (not shown). Without intending to limit the invention to any particular mechanism, the results suggest that insertion of the chimera F proteins into a VLP membrane insures the stability of the conformation of the pre-fusion F proteins. This was a surprising finding.

Example 6

Induction of Neutralizing Antibodies in Mice

Figure 1:
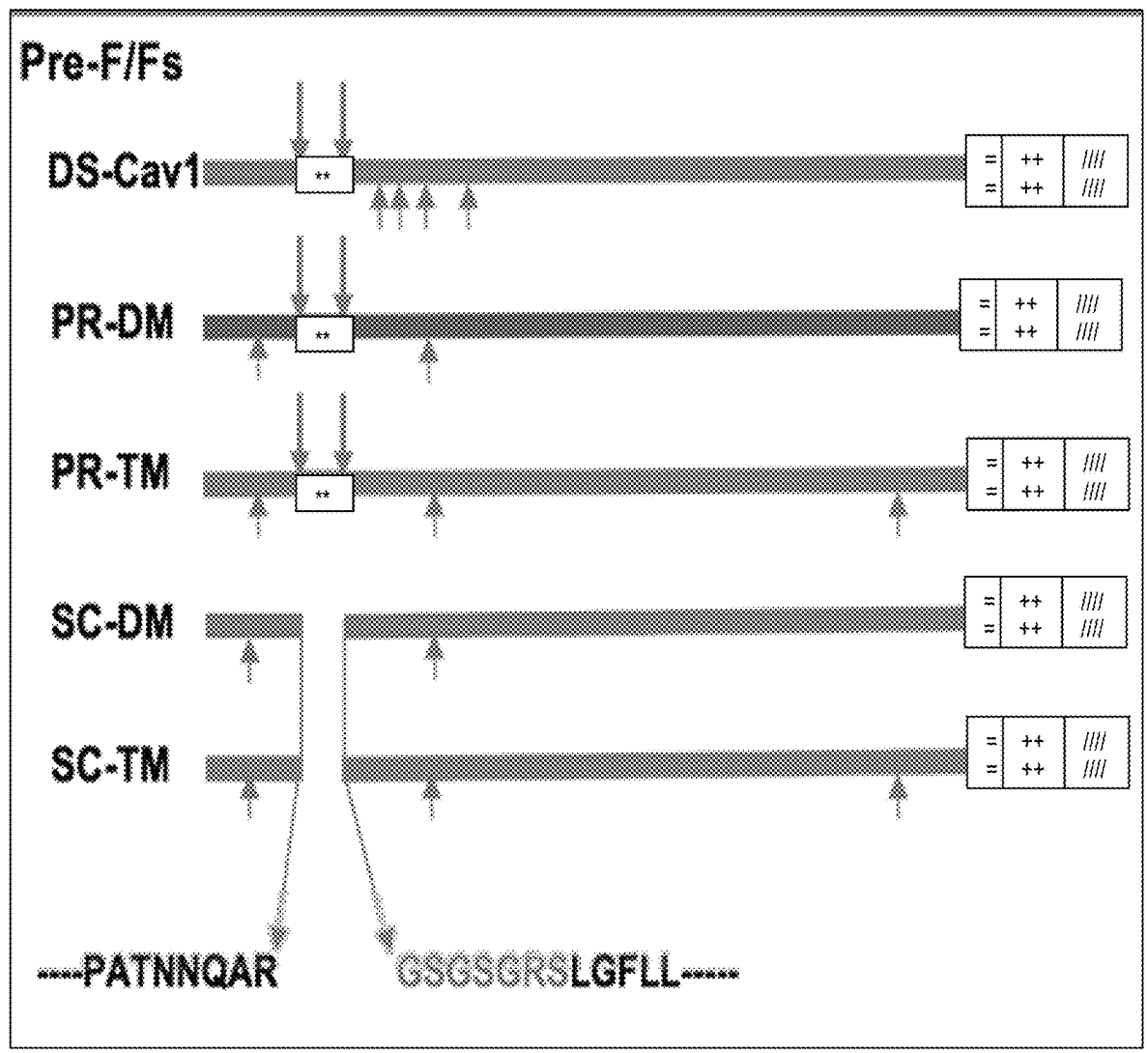
FIG. 1: Fusion Protein Chimeras: Shown is a diagram of five different chimeras, each containing one version of mutation-stabilized RSV pre-fusion F proteins. DS-Cav1 protein containing four mutations (short arrows) was previously described (McLellan et al. 2013). PR-DM and PR-TM are processed (cleaved) F proteins with two or three mutations, respectively, indicated by short arrows. SC-DM and SC-TM are uncleaved with the p27 sequence and cleavage sites deleted and a linker sequence, in **, inserted. SC-DM and SC-TM also contained two or three mutations, respectively, indicated by short arrows. All proteins contained the ectodomain of the mutant RSV fusion (F) protein fused to the foldon sequence (==), the NDV transmembrane domain (++), and NDV cytoplasmic domain (/////). See sequences of FIGS. 14-19, which were codon-optimized for humans.
Figure 6:
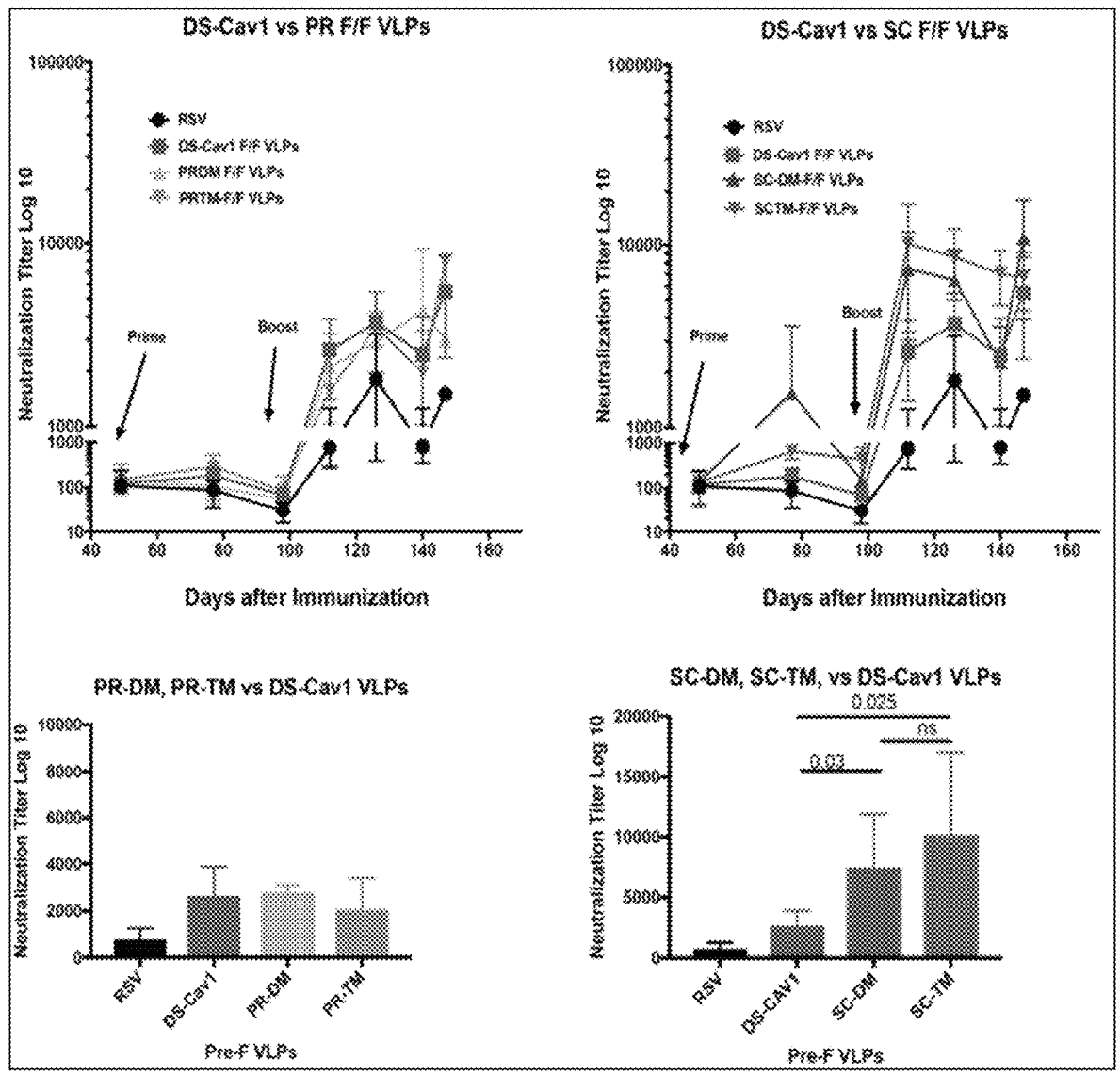
FIG. 6: Neutralization Titers in Sera from animals after VLP Immunization: Sera obtained at each time point after the VLP prime immunization was pooled and NA titers determined in a classical plaque reduction assay. Top left panel compares titers obtained with DS-Cav1 VLP sera with titers obtained with PR-DM VLP and PR-TM VLP sera. Top right panel compares titers using sera from SC-DM and SC-TM VLP sera with DS-Cav1 VLP sera. Bottom left panel compares titers obtained at 2 weeks post boost with the DS-Cav1 and PR VLP sera. Bottom right panel compares titers at 2 weeks post boost with DS-Cav1 and SC VLP sera. There were no statistical differences between results with DS-Cav1 VLP and the PR VLP sera. Statistically significant results between DS-Cav1 and SC VLP results are indicated. Results are the average with standard deviation of 3 to 6 separate determinations.

We determined if the VLPs containing different versions of stabilized pre-fusion F protein induced similar levels of neutralizing antibodies in mice. Groups of mice were primed with intramuscular injection (IM) of 40 micrograms/total VLP protein (8 micrograms/F/F protein) and then boosted at day 100 with 30 micrograms total VLP protein. Serum samples were acquired at times after the prime immunization. FIG. 6 shows the neutralizing antibody (NA) titers of pooled sera with time after the prime immunization. The top left panel compared the titers obtained after immunization with the PR VLPs with those obtained with DS Cav-1 VLPs and top right panel compares the titers after immunization with SC VLPs and DS Cav-1 VLPs. There were no statistically significant differences between titers obtained by immunization with the PR VLPs and those obtained with DS Cav-1 VLPs.

In contrast, both the SC VLPs induced two to five fold higher NA titers than the DS-Cav1 VLPs both after the prime and after the boost. The titers 2 weeks after the boost are shown in FIG. 6 bottom right panel, with statistical significance of differences between groups indicated. The titers obtained with SC VLPs immunization were statistically significantly higher than titers obtained with the DS-Cav1 VLPs. Thus, the SC-DM and SC-TM1 pre-fusion F proteins assembled in VLPs show significant improvement in induction of protective immune responses compared to DS-Cav1 VLPs. This finding also was surprising. However, without intending to limit the invention to any particular mechanism, the results suggest that the conformation of different pre-fusion F proteins is different.

Example 7

Induction of Neutralizing Antibodies in Pregnant Cotton Rats

Figure 7:
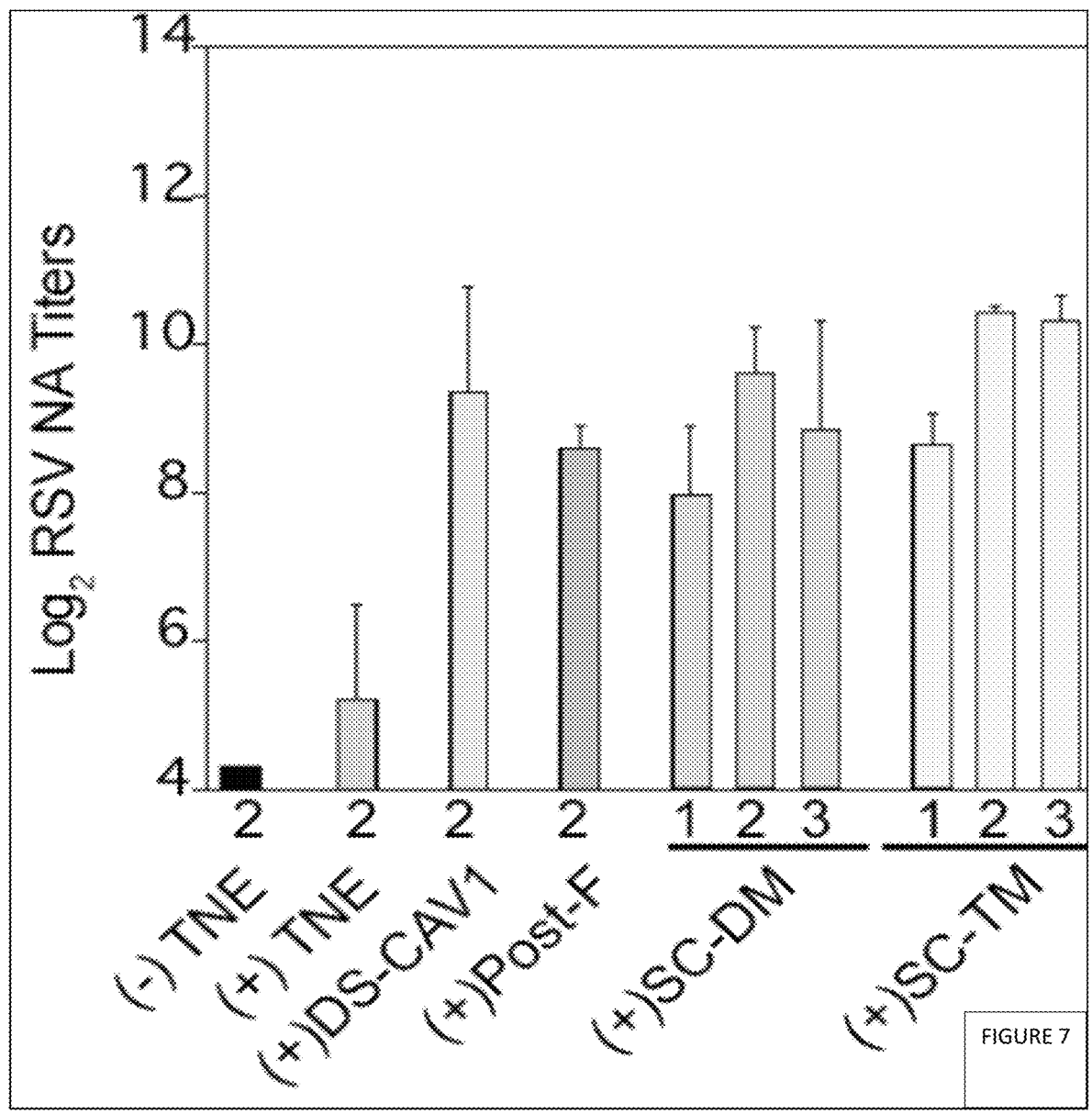
FIG. 7: Neutralizing Antibody Titers in Immunized Dams: Shown are the neutralizing antibody titers in pooled sera obtained from dams just before delivery. Numbers refer to weeks into gestation when dams were immunized. Symbol+ means RSV primed.

Because of the superior results using SC-DM and SC-TM VLPs in mice, these VLPs were used in cotton rats to compare the efficacy of SC-DM and SC-TM VLPs in these animals (FIG. 7) as well efficacy as maternal vaccines for protection of neonates from RSV infection (FIGS. 8 and 9). First, we determined the neutralizing antibody titers induced in pregnant cotton rats with SC-DM and SC-TM VLPs. Similar to results in mice, these two VLPs induced higher neutralizing antibody titers than DS-Cav1 VLPs (FIG. 7).

Example 8

Protection of Offspring of Immunized Dams (Moms)

These immunized cotton rat dams from Example 7 above were RSV infected. The animals were bred and then vaccinated at 1, 2, and 3 weeks of gestation. FIG. 8 shows the serum antibody titers in pups 4 weeks after birth. The results show that SC-TM VLP immunization of dams resulted in the highest levels of neutralizing antibodies in the pups, levels much higher than in pups delivered from dams immunized with DS-Cav1 or SC-DM VLPs.

At 4 weeks after the birth, the pups were challenged with RSV. Four days later the pups were sacrificed and the RSV titer in their lungs was measured to determine the extent of protection afforded by the maternal antibodies transferred to the pups. One group of pups were delivered from dams immunized with DS-Cav1 VLPs at 2 weeks of gestation for comparison.

FIG. 9 shows that SC-TM immunization of dams at 2 weeks of gestation resulted in a significant reduction of the RSV lung titers in RSV challenged pups compared titers in pup lungs from dams immunized with DS-Cav1 VLPs. Immunization of dams with SC-TM VLPs at 3 weeks of gestation very dramatically reduced pup lung RSV titers further.

Example 9

Methods for Production of VLPs

We constructed four chimeric BV vectors (one for each VLP protein gene encoding VLP proteins SC-TM F/F, H/G, NP, and M; FIG. 21A-D), in which the VLP protein genes were inserted in the polyhedron gene of the Baculovirus genome (exemplified by GenBank Accession numbers NC001623, NC004323, NC008349) downstream (i.e., at the C-terminal end) of a hybrid beta globin-CMV promoter (SEQ ID NO:14, FIG. 20A).

We used these four chimeric BVs to infect 293F cells (Lee & Yu. Expression in mammalian cells using BacMam viruses. In Expression Systems: (M. R. Dyson and Y. Durocher, eds) Chapter 15, page 261. © Scion Publishing Limited, 2007. Methods Express; and Fornwaldet al. 2006. Methods in Molecular Biology 338: 95) and recovered VLPs from cell supernatants with efficiencies very similar to that after transient transfection (Pantua et al. J Virol. 2006 November; 80(22):11062-73; McGinnes et al. J Virol. 2010 May; 84(9):4513-23; Murawski et al. 2010 J. Virol. 84: 1110-1123) (using polyethyleneimine (PEI) as a transfection reagent) of either avian cells or 293 cells with plasmids encoding the VLP protein genes (shown in FIG. 10). The release of VLPs was the same using transfection of cells vs chimeric BV infection of cells.

To determine if the immunogenicity of VLPs prepared with chimeric BV was the same as that of VLPs released from transfected avian cells, we immunized mice with purified VLPs from avian cells (30 micrograms total VLP protein/animal) or VLPs from chimeric BV-infected 293F cells (30 micrograms/animal). FIG. 11 shows that both VLPs induced similar amounts of serum neutralizing antibody titers (right panel) and anti-IgG F antibodies (left panel). Thus, VLPs produced by chimeric BV-infected 293 cells were as effective in stimulating immune responses as VLPs produced by transient transfection of avian cells. This demonstrates that chimeric BVs can produce clinical-grade VLPs in a cost-effective manner.

To increase the yields of VLPs from chimeric BV transduced cells, we tested two modifications of our protocols:

The first modification was the addition of sodium-butyrate to cells (Galasinski 2000 Molecular and Cellular Biology 20:1923-1930; Grunstein 1997, Nature 389:349; Neumann et al. 2007, Journal of Virology 81:6106-6110; Barbara et al. 2009, Biochemical, Molecular and Epigenetic Mechanisms of Valproic Acid Neuroprotection. Current Molecular Pharmacology; Lee & Yu. Expression in mammalian cells using BacMam viruses, in Expression Systems: (M. R. Dyson and Y. Durocher, eds) Chapter 15, page 261. © Scion Publishing Limited, 2007. Methods Express).

The second modification was to increase the multiplicity of infection (moi) of the chimeric BV. To control the moi in cells, chimeric BV stocks were concentrated by centrifugation and the concentrated stock was titrated by a plaque assay on sf9 insect cells to determine the number of viruses per milliliter. Using this information, the volume of the stock containing a given number of infectious viruses was calculated. To infect cells with a given moi, the volume of virus stock containing the required number of viruses/cell was multiplied by the number of cells to be infected.

FIG. 12 demonstrates that inclusion of 5 mM Na-butyrate during VLP release from PEI-transfected 293F cells increased the yield of VLPs (compare lanes 1, 2 with 3 and 4 and lanes 8 and 9 with lanes 10 and 11). Importantly, Na butyrate significantly increased the yield from chimeric BV transduced 293F cells by 6 fold (compare lanes 4 with 5 and lanes 11 with 12).

FIG. 13 demonstrates that the yield of VLPs can be significantly increased by increasing the moi of the chimeric BV (From a moi of 12.5 to a moi of 50 there was a 2.2 fold increase) and by combining the effect with the use of Na-butyrate.

Example 10

Total Anti-F Antibody Titers

To determine if the differences in NAbs titers could be due to differences in total anti-F antibodies induced by the different VLPs, the total anti-pre-F or anti-post-F IgG induced was measured by ELISA. Titers of antibodies (ng/ml) that bound soluble pre-fusion F protein (FIG. 23A-D, panels FIG. 23A, B) or soluble post-fusion F protein (Panels FIG. 23C, D) were measured. FIG. 23A-D, panels FIGS. 23A and C, show anti-F IgG titers with times after the prime and boost comparing sera from PR VLPs with DS-Cav1 VLP immunizations. Panel FIGS. 23B and D shows titers in sera from both SC VLPs compared to DS-Cav1 VLPs. There were no statistically significant differences in anti-F protein antibody titers that bound either the soluble pre-F or post-F targets in sera induced by any of the pre-fusion F/F VLPs.

Example 11

Relative Concentration of D25 and AM14 Blocking Antibodies in Sera

That both the SC VLPs induce higher neutralization antibody titers than DS-Cav1 VLPs but total anti-F IgG antibodies are similar suggests that antibodies induced by the SC VLPs differ in epitope specificities from those induced by DS-Cav1 VLPs. To test this hypothesis, the concentration of anti-pre-F binding IgG antibodies in the different sera that block binding of representative pre-fusion specific mAb to soluble pre-fusion F protein was measured. For these experiments, the approach was first validated using sera from Post-F and DS-Cav1 VLP immunized mice as shown in FIG. 24A-C, panels FIG. 24A-C. Soluble pre-F protein target (soluble DS-Cav1) was bound to Ni coated microtiter plates to ensure that the target F protein bound preferentially through the polyhistidine tag at its carboxyl terminus in order to mimic presentation of the protein as in virus or VLPs. The binding of pre-fusion, trimer specific mAb AM14 (panel FIG. 24A), pre-fusion specific site 0 mAb D25 (panel FIG. 24B), and site II specific mAb motavizumab (panel FIG. 24C) to soluble DS-Cav1 F protein target in the presence of increasing concentrations of DS-Cav1 VLP induced anti-pre-F IgG or Post-F VLP induced anti-pre-F IgG in sera was measured. The figure shows that approximately 95 ng/ml of total anti-pre-F protein IgG in the DS-Cav1 VLP sera blocked 50% of AM14 binding while 675 ng/ml of total anti-pre-F IgG in the post-F VLP sera were required to block 50% of the AM14 binding. Thus, Post-F VLP sera contained a much lower concentration of antibodies that will block mAb AM14 binding than sera induced by DS-Cav1 VLPs. Panel FIG. 24B shows that approximately 425 ng/ml of anti-pre-F IgG in DS-Cav1 VLP sera were required to block 50% of binding of mAb D25 while an estimated 2333 ng/ml of anti-F IgG in Post-F VLP sera were required to block 50% of mAb D25 binding. Again DS-Cav1 VLP sera had much higher concentrations of anti-pre-F antibodies that blocked D25 binding than sera from Post-F VLP immunization. Panel FIG. 24C shows that similar amounts of anti-pre-F binding IgG in DS-Cav1 VLP sera and in Post-F VLP sera were required to block 50% of motavizumab binding.

This experiment has been repeated in two other completely different experiments with separate groups of 5 mice immunized with different preparations of the DS-Cav1 and Post-F VLPs and the results from all three experiments are shown in Table 1.

TABLE 1

Concentration (ng/ml) of Anti-Pre-F IgG Binding Antibodies that Block 50% of Binding of Monoclonal Antibodies to Soluble DS-Cav1 Protein

| Monoclonal Antibody | VLP Immunogen | |
|---|---|---|
| | Post-F/F | DS-Cav1 F/F |
| AM14 | | |
| Exp 1 | 950 +/− 70 | 65 +/− 5 |
| Exp 2 | 675 +/− 170 | 95 +/− 7 |
| Exp 3 | 1600 +/− 100 | 136 +/− 56 |
| D25 | | |
| Exp 1 | 7500 +/− 4000 | 550 +/− 50 |
| Exp 2 | 2333 +/− 577 | 425 +/− 50 |
| Exp 3 | 8333 +/− 2100 | 505 +/− 130 |
| Motavizumab | | |
| Exp 1 | 2000 +/− 100 | 825 +/− 25 |
| Exp 2 | 1000 +/− 50 | 1000 +/− 100 |

Legend to Table 1: Shown are concentrations (ng/ml) of anti-pre-F binding IgG in pooled sera obtained at 4 weeks after boost immunizations with DS-Cav1 F VLPs or Post-F VLPs that blocked binding of mAb AM14, D25, or Motavizumab to soluble pre-F protein target (DS-Cav1). Results are the mean of at least three separate determinations with standard deviations indicated. Each group in each experiment (Exp) contained five mice. Values at or somewhat above 2000 ng/ml indicated sera that only very weakly blocked binding. Values at or above 2000 ng/ml were quite variable from experiment to experiment as indicated by the large standard deviation.

In these experiments, using sera from 4 weeks post-boost, 65-138 ng/ml of anti-pre-F IgG in the DS-Cav1 VLP sera were required to block 50% binding of mAb AM14 while 675-1500 ng/ml of anti-pre-F IgG in post-F VLP sera were required. Using mAb D25, 425-550 ng/ml of anti-pre-F IgG in DS-Cav1 VLP sera were required to bock 50% of the binding of D25 while post-F VLP sera required 2333-8333 ng/ml to block 50% of the binding of mAb D25. Again, the concentration of antibodies in DS-Cav1 VLP sera that blocked binding of mAb D25 was much higher than in post-F VLP sera.

In parallel with experiment three shown in Table 1, the concentrations of anti-pre-F IgG in sera from the PR and SC VLP immunizations required to block 50% of the binding of AM14 and D25 were determined. Values obtained with pooled sera obtained at 4 weeks post boost are shown in FIG. 25A-F, panels FIG. 25A-C while the values obtained from sera obtained at 2, 4, and 7 weeks post boost are shown in FIG. 29A-D.

The sera that blocked mAb AM 14 binding at concentrations comparable to DS-Cav1 VLP sera were that from SC-DM VLP and SC-TM VLP immunizations (73+/−12 ng/ml and 150+/−40 ng/ml respectively) (FIG. 25A). Sera from the PR VLP immunizations required 650+/−100 ng/ml (PR-DM) and 420+/−100 ng/ml (PR-TM) anti-pre-F IgG to block 50% of the binding of mAb AM14. None of the VLPs induced sera that blocked D25 binding at levels comparable to DS-Cav1 VLP sera. Again, SC-DM sera contained the highest concentration of mAb D25 blocking antibodies (FIG. 25B).

The sera from Post-F VLP immunizations (FIGS. 29 A and B) or from RSV immunized animals (FIGS. 25 A and B) were either not able to block or very weakly blocked the binding of mAb D25 and AM14.

Competition of polyclonal sera with binding of palivizumab has been commonly used to assess the effectiveness of responses to RSV vaccine candidates [33]. It has, however, become clear that results are not necessarily predictive of the success of the vaccine candidate in animals or humans [18, 19]. However, because of its common use in vaccine candidate assessment, we included quantification of the concentration of anti-pre-F antibodies in all sera that blocked palivizumab binding. The results are shown in FIG. 25A-F, panel FIG. 25C. The sera from animals immunized with all five pre-fusion F containing VLPs blocked palivizumab binding to varying degrees with DS-Cav1 and the SC VLPs inducing the highest concentration of blocking antibodies. Thus, the relative concentrations of antibodies induced by the five-different pre-fusion F containing VLPs that will block binding of three different monoclonal antibodies varies significantly, indicating that the pool of antibodies induced by the different VLPs are not the same.

The target for the serum antibody blocking of mAb binding described above was soluble DS-Cav1 F protein. The mutations in the PR and SC mutant F proteins contained single amino acid changes in regions of the F protein previously identified as forming or near the site 0 epitope (amino acids 61-76 and 195-214) [16]. Although D25, a site 0 specific mAb, bound to the PR-TM, SC-DM, and SC-TM VLPs as well as or better than the DS-Cav1 VLPs (FIG. 3A), we considered the possibility that the results of sera blocking of mAb D25 binding to soluble F protein might be different using a soluble pre-fusion target that contained the SC and PR mutations. FIG. 25A-F, panel FIG. 25E, shows the results of serum antibody blocking of mAb D25 using soluble SC-TM as target. The results were quite different from those obtained with soluble DS-Cav1 target (panel FIG. 25B) indicating that the sera induced by the PR-TM and SC mutant F proteins contained a high concentration of antibodies that would block binding of mAb D25 to a target containing the point mutations in site 0 and a lower concentration of antibodies that block binding to DS-Cav1 target. By contrast, sera induced by DS-Cav1 VLPs could not block binding of mAb D25 to SC-TM target (FIG. 25E).

As controls, we tested the ability of sera from the five VLP immunizations to block binding of mAb AM14 and palivizumab to soluble SC-TM, although the five F proteins did not contain mutations at or near the sites recognized by these mAbs. Surprisingly, however, the results using soluble SC-TM as target were quite different than results using the DS-Cav1 as target. FIG. 25A-F, panels FIGS. 25D and F, show results of serum antibody blocking of mAb AM14 and palivizumab binding, respectively, using purified soluble SC-TM F protein as target. Sera induced by DS-Cav1 VLPs and PR-DM VLPs did not block or only weakly blocked binding of either mAb AM14, or palivizumab to soluble SC-TM F protein target. The only sera that could effectively block the binding of mAb AM14 to soluble SC-TM F protein target were induced by PR-TM, SC-DM and SC-TM VLPs. Sera from all VLP immunizations could block the binding of palivizumab to SC-TM target, to various degrees. These results suggest differences in conformation of soluble DS-Cav1 and SC-TM or differences in the populations of antibodies induced by VLPs containing different pre-F proteins.

Interestingly, two sequential RSV infections yielded antibodies that would block mAb AM14 to DS-Cav1 target moderately well but did not block binding using SC-TM target. This serum would not block D25 or palivizumab binding to either target. Thus, RSV infections yield populations of antibodies quite different from all the pre-F VLPs.

We considered the possibility that the failure of some sera to compete with mAb binding to soluble SC-TM F protein was due to failure of that sera to bind to this target adhered to Ni plates. A direct comparison of total binding of each serum to the soluble SC-TM and soluble DS-Cav1 target showed binding to soluble SC-TM of sera from DS-Cav1 and PR-DM VLP sera was slightly less than binding to soluble DS-Cav1 protein while binding of sera from SC-DM and SC-TM to the two targets was the same (FIG. 30). However, the decrease in binding of some sera to soluble SC-TM seems unlikely to completely account for the lower levels or total absence of blocking mAb binding by some of the sera. Thus, the results of blocking of binding to the soluble SC-TM F protein versus soluble DS-Cav1 are consistent with the idea that the populations of antibodies induced by PR-TM or the SC VLPs are different than that induced DS-Cav1 VLPs.

Example 12

Protection from RSV Challenge

We next determined if there were differences in protection of animals from RSV challenge after the different VLP immunizations. At 7 weeks post boost, immunized mice were RSV challenged and then sacrificed four days later. Lung titers were determined to assess any RSV replication after challenge. FIG. 26 shows that there was no detectable virus in the lungs of any of the animals in any of the groups except in sham vaccinated animals, a result that was expected since even a single RSV infection results in protection from RSV replication in mice [20, 21]. Assessment of protection afforded by immunization with an RSV vaccine candidate is better done in cotton rats, which are more permissive to RSV infection.

REFERENCES CITED IN THE ABOVE "BACKGROUND OF THE INVENTION" AND EXAMPLES 2-9

1. Ngwuta et al., Science Transl Med 7:309ra162.
2. McLellan et al., Science 342:592-598.
3. Krarup et al., Nat Commun 6:8143-8155.
4. Flynn et al., PLOS ONE 11:e0164789.
5. Russell et al., Viral Immunology 31:133-141.
6. Gilman et al., PLoS Pathog 11:e1005035.

REFERENCES CITED IN THE ABOVE EXAMPLES 1, AND 10-12, AND "DESCRIPTION OF THE INVENTION"

1. Shi et al., *The Lancet* 390, no. 10098 (2017): 946-58.
2. Karron et al., In *Vaccines*, edited by S A Plotkin, W A Orenstein and PA Offit 1146: Saunders-Elsevier, 2008.
3. Falsey et al., *N. Engl. J. Med* 352 (2005): 1749-59.
4. Falsey et al., *Clin Microbiol Rev* 13 (2000): 371-84.
5. Han et al., *J Infect Dis* 179 (1999): 25-30.
6. Raboni et al., *Transplant.* 76 (2003): 142-46.
7. Thompson et al., *JAMA* 289, no. 2 (2003): 179-86.
8. Ison et al., *Current Opinion in Oncology* 21, no. 2 (2009): 171-76.
9. Shah et al., *Blood* 117, no. 10 (2011): 2755-63.
10. Hall et al., *N Engl J Med* 344 (2001): 1917-28.
11. Jardetsky et al., *Nature.* 427 (2004): 307-08.
12. Lamb et al. In *Fields Virology*, edited by D. M. Knipe, P. M. Howley, D. E. Griffin, R. A. Lamb, M. A. Martin, B. Roizman and S. E. Strauss, 1450-96. Philadelphia: LippincottWilliams &Wilkins, 2007.
13. Swanson et al., *Proc. Natl. Acad. Sci USA.* 108, no. 23 (2011): 9619-24.
14. McLellan et al., *Nat Struct Mol Biol* 17, no. 2 (2011): 248-50.
15. McLellan et al., *Science* 340, no. 6136 (2013): 1113-17.
16. McLellan et al., *Science* 342 (2013): 592-98.
17. Graham et al., *Current Opinion in Immunology* 35 (2015): 30-38.
18. Neuzil et al., *Clinical and Vaccine Immunology* 23, no. 3 (2016): 186-88.
19. Falloon et al., *J. of Inf. Diseases* 216, no. 11 (2017): 1362-70.

20. McGinnes et al., *J Virol* 85 (2011): 366-77.
21. Murawski et al., *J Virol* 84 (2010): 1110-23.
22. Cullen et al., *J. Transl. Med.* 13, no. 1 (2015): 1-13.
23. McGinnes et al., *J of Virol.* 89 (2015): 6835-47.
24. Cullen et al., *Human Vaccines & Immunotherapeutics* (2017): 1-10.
25. Bachmann et al., *Nat Rev Immunol* 10, no. 11 (2010): 787-96.
26. Blanco et al., *Nature Comm.* 9, no. 1 (2018): 1904-14.
27. Krarup et al., *Nat Commun.* 6 (2015): 8143-55.
28. Flynn et al., *PLoS ONE* 11, no. 10 (2016): e0164789.
29. Russell et al., *Viral Immunology* 31, no. 2 (2018): 133-41.
30. McGinnes et al. In *Current Protocols in Microbiology*: John Wiley & Sons, Inc., 2013.
31. Frank et al., *J Mol Biol* 308 (2001): 1081-89.
32. Gilman et al., *PLoS Pathog* 11, no. 7 (2015): e1005035.
33. Smith et al., *PLoS ONE* 7, no. 11 (2012): e50852.
34. Magro et al., *Proc. Natl. Acad. Sci.* 109, no. 8 (2012): 3089-94.
35. Blais et al., *J. Virol.* 91, no. 13 (2017).
36. Cimica et al., *Clinical and Vaccine Immunology* 23, no. 6 (2016): 451.
37. Liang et al., *J. Virol.* 91, no. 15 (2017): e00189-17.
38. Palomo et al., *J. of Virol.* 90, no. 11 (2016): e00338-18.
39. Swanson et al., *J. of Virol.* 88, no. 20 (2014): e01225-14.
40. Wu et al., *J Mol. Biol.* 350, no. 1 (2005): 126-44.
41. Mousa et al., *Proc Natl Acad of Sci USA* 113, no. 44 (2016): E6849-E58.

Each and every publication and patent mentioned in the above specification is herein incorporated by reference in its entirety for all purposes. Various modifications and variations of the described methods and system of the invention will be apparent to those skilled in the art without departing from the scope and spirit of the invention. Although the invention has been described in connection with specific embodiments, the invention as claimed should not be unduly limited to such specific embodiments. Indeed, various modifications of the described modes for carrying out the invention which are obvious to those skilled in the art and in fields related thereto are intended to be within the scope of the following claims.

I claim:

1. A vaccine comprising
   a) a recombinant Newcastle disease virus-like particle (ND VLP), said ND VLP comprises one or more recombinant chimeric mutation-stabilized pre-fusion F proteins that comprise a) SEQ ID NO:12, b) SEQ ID NO:10, or c) a combination of both SEQ ID NO:12 and SEQ ID NO:10, and
   b) a physiologically acceptable carrier.

2. A method for immunizing a first mammalian subject against respiratory syncytial virus (RSV), comprising administering an immunologically effective amount of the vaccine of claim 1 to a mammalian subject to produce a treated subject, wherein said administering is under conditions to produce an immune response to said one or more recombinant chimeric mutation-stabilized pre-fusion F proteins and an immunogenic portion thereof.

3. The method of claim 2, wherein said recombinant VLP comprises SEQ ID NO:12.

4. The method of claim 2, wherein said immune response comprises an increased level of antibody in serum of said treated subject, wherein said antibody specifically binds with said one or more recombinant chimeric mutation-stabilized pre-fusion F proteins and said immunogenic portion thereof.

5. The method of claim 2, wherein said mammalian subject is female.

6. The method of claim 5, wherein said immunizing is before birth of an offspring of said female subject.

7. A method for immunizing a mammalian subject against respiratory syncytial virus (RSV), said subject having a gestational parent, comprising administering, prior to birth of said mammalian subject by said gestational parent, an immunologically effective amount of the vaccine of claim 1 to said gestational parent to produce a treated gestational parent, wherein said administering is under conditions to produce an immune response to said one or more recombinant chimeric mutation-stabilized pre-fusion F proteins and an immunogenic portion thereof in said treated gestational parent.

8. The method of claim 7, wherein said administering is during gestation of said mammalian subject by said gestational parent.

9. The method of claim 7, wherein said immune response comprises an increased level of antibody in serum of said treated gestational parent, wherein said antibody specifically binds with said one or more recombinant chimeric mutation-stabilized pre-fusion F proteins and said immunogenic portion thereof.

10. The method of claim 7, wherein said immune response comprises an increased level of antibody in serum of said mammalian subject, wherein said antibody specifically binds with said one or more recombinant chimeric mutation-stabilized pre-fusion F proteins and said immunogenic portion thereof.

11. The method of claim 7, wherein said immune response comprises an increased level of protection of said mammalian subject against RSV infection compared to in the absence of said administering.

12. The vaccine of claim 1, said mutation-stabilized pre-fusion F proteins comprise SEQ ID NO:12.

13. The vaccine of claim 1, said mutation-stabilized pre-fusion F proteins comprise SEQ ID NO:10.

14. The vaccine of claim 1, said mutation-stabilized pre-fusion F proteins comprise SEQ ID NO:12 and SEQ ID NO:10.

15. The method of claim 2, said mutation-stabilized pre-fusion F proteins comprise SEQ ID NO:10.

16. The method of claim 2, said mutation-stabilized pre-fusion F proteins comprise SEQ ID NO:12 and SEQ ID NO:10.

17. The method of claim 7, said mutation-stabilized pre-fusion F proteins comprise SEQ ID NO:12.

18. The method of claim 7, said mutation-stabilized pre-fusion F proteins comprise SEQ ID NO:10.

19. The method of claim 7, said mutation-stabilized pre-fusion F proteins comprise SEQ II) NO:12 and SEQ ID NO:10.

* * * * *